(12) United States Patent
Kmiec et al.

(10) Patent No.: US 7,566,535 B2
(45) Date of Patent: *Jul. 28, 2009

(54) ENHANCED OLIGONUCLEOTIDE-MEDIATED NUCLEIC ACID SEQUENCE ALTERATION

(75) Inventors: Eric B. Kmiec, Landenberg, PA (US); Hetal Parekh-Olmedo, Mantua, NJ (US); Erin E. Brachman, Newark, DE (US)

(73) Assignee: University of Delaware, Newark, DE (US)

( * ) Notice: Subject to any disclaimer, the term of this patent is extended or adjusted under 35 U.S.C. 154(b) by 1088 days.

This patent is subject to a terminal disclaimer.

(21) Appl. No.: 10/384,918

(22) Filed: Mar. 7, 2003

(65) Prior Publication Data

US 2003/0207451 A1 Nov. 6, 2003

Related U.S. Application Data

(60) Provisional application No. 60/363,341, filed on Mar. 7, 2002, provisional application No. 60/363,053, filed on Mar. 7, 2002, provisional application No. 60/363,054, filed on Mar. 7, 2002, provisional application No. 60/416,983, filed on Oct. 7, 2002.

(51) Int. Cl.
*C12Q 1/68* (2006.01)
*C07H 21/00* (2006.01)
*C07K 14/00* (2006.01)

(52) U.S. Cl. .......................... 435/6; 536/22.1; 530/350

(58) Field of Classification Search .................. 435/6; 530/350; 536/22.1

See application file for complete search history.

(56) References Cited

U.S. PATENT DOCUMENTS

| | | | |
|---|---|---|---|
| 5,139,941 A | 8/1992 | Muzyczka et al. | |
| 5,432,272 A | 7/1995 | Benner | |
| 5,565,350 A | 10/1996 | Kmiec | |
| 5,700,470 A | 12/1997 | Saito et al. | |
| 5,731,181 A | 3/1998 | Kmiec | |
| 5,756,325 A | 5/1998 | Kmiec | |
| 5,760,012 A | 6/1998 | Kmiec et al. | |
| 5,776,744 A | 7/1998 | Glazer et al. | |
| 5,780,296 A | 7/1998 | Holloman et al. | |
| 5,795,972 A | 8/1998 | Kmiec | |
| 5,801,154 A | 9/1998 | Baracchini | 435/6 |
| 5,834,182 A | 11/1998 | Alexander et al. | |
| 5,871,984 A | 2/1999 | Kmiec | |
| 5,888,983 A | 3/1999 | Kmiec et al. | |
| 5,912,340 A | 6/1999 | Kutyavin | 435/6 |
| 5,928,638 A | 7/1999 | Uchida et al. | |
| 5,945,339 A * | 8/1999 | Holloman et al. | 435/477 |
| 5,955,363 A | 9/1999 | Lewis | 435/6 |
| 5,962,426 A | 10/1999 | Glazer | |
| 6,004,804 A | 12/1999 | Kumar | 435/6 |
| 6,043,060 A | 3/2000 | Imanishi | |
| 6,057,102 A | 5/2000 | Landau et al. | |
| 6,130,089 A | 10/2000 | Lisziewicz | |
| 6,136,601 A | 10/2000 | Meyer | 435/6 |
| 6,239,176 B1 | 5/2001 | Nudelman et al. | |
| 6,261,841 B1 | 7/2001 | Cohen et al. | |
| 6,268,490 B1 | 7/2001 | Imanishi et al. | |
| 6,271,360 B1 | 8/2001 | Metz et al. | |
| 6,303,376 B1 | 10/2001 | Glazer | |
| 6,821,759 B1 * | 11/2004 | Heintz et al. | 435/91.4 |
| 6,936,467 B2 * | 8/2005 | Kmiec et al. | 435/455 |
| 7,226,785 B2 * | 6/2007 | Kmiec et al. | 435/440 |
| 2002/0119570 A1 | 8/2002 | Yoon | 435/6 |
| 2002/0143052 A1 | 10/2002 | Lan-Hargest et al. | |
| 2003/0051270 A1 | 3/2003 | Kmiec et al. | 435/6 |
| 2003/0217377 A1 | 11/2003 | Kmiec et al. | 435/6 |

FOREIGN PATENT DOCUMENTS

| | | |
|---|---|---|
| EP | 1170008 | 1/2002 |
| WO | WO 97/35990 | 10/1997 |
| WO | WO 97/40183 | 10/1997 |
| WO | WO 97/47307 | 12/1997 |
| WO | WO 98/39352 | 9/1998 |
| WO | WO 98/48825 | 11/1998 |
| WO | WO 98/55449 | 12/1998 |
| WO | WO 99/14226 | 3/1999 |
| WO | WO 99/37150 | 7/1999 |
| WO | WO 99/58702 | 11/1999 |
| WO | WO 00/21979 | 4/2000 |
| WO | WO 00/23567 | 4/2000 |
| WO | WO 00/24917 | 5/2000 |
| WO | WO 00/50748 | 8/2000 |
| WO | WO 00/51424 | 9/2000 |
| WO | WO 00/51565 | 9/2000 |
| WO | WO 00/52033 | 9/2000 |
| WO | WO 00/56748 | 9/2000 |
| WO | WO 00/66604 | 11/2000 |
| WO | WO 00/71703 | 11/2000 |
| WO | WO 01/12193 | 2/2001 |
| WO | WO 01/15740 | 3/2001 |
| WO | WO 01/16106 | 3/2001 |
| WO | WO 01/18045 | 3/2001 |

(Continued)

OTHER PUBLICATIONS

Marks et al. Histone deacetylase inhibitors: inducers of differntiation or apoptosis of transformed cells. J Natl Cancer Inst., vol. 92, No. 15, pp. 1210-1216, Aug. 2000.*

(Continued)

Primary Examiner—Suryaprabha Chunduru
(74) Attorney, Agent, or Firm—McCarter & English

(57) ABSTRACT

The invention is directed to oligonucleotide-mediated repair or alteration of genetic information, such as nucleic acid sequence alteration, and methods, compositions and kits for enhancing the efficiency of such alteration. Specifically, the invention incorporates the use of factors such as Histone Deacetylase Inhibitor (HDAC), Lambda phage beta protein, or hydroxyurea to achieve such enhanced efficiency.

16 Claims, 12 Drawing Sheets

FOREIGN PATENT DOCUMENTS

| | | |
|---|---|---|
| WO | WO 01/18171 | 3/2001 |
| WO | WO 01/24615 | 4/2001 |
| WO | WO 01/34843 | 5/2001 |
| WO | WO 01/38322 | 5/2001 |
| WO | WO 01/49240 | 7/2001 |
| WO | WO 01/70675 | 9/2001 |
| WO | WO 01/73002 | 10/2001 |
| WO | WO 01/92512 | 12/2001 |
| WO | WO 02/06307 | 1/2002 |
| WO | WO 02/10364 | 2/2002 |
| WO | WO 02/14495 | 2/2002 |
| WO | WO 02/26967 | 4/2002 |

OTHER PUBLICATIONS

Synder RD. et al. The role of deoxynucleoside triphosphate pools in the inhibition of DNA-excision repair and replication in huma cells by hydroxyurea. Mutation Research, vol. 131, pp. 163-172, 1984.*

Li et al. Progressive formation of DNA lesions in cultured Ehrlich ascites tumor cells treated with hydroxyurea. Cancer Research, vol. 47, pp. 2755-2758, 1987.*

Marks et al. Histone deacetylase inhibitors: inducers of differentiation or apoptosis of transformed cells. J Natl Cancer Inst., vol. 92, No. 15, pp. 1210-1216, Aug. 2000.*

Cole-Strauss et al. targeted gene repair directed by the chimeric RNA/DNA oligonucleotide in a mammalian cell-free extract. Nucleic Acids Res., vol. 27, No. 5, pp. 1323-1330, 1999.*

Kaji et al. Gene and stem cell therapies. JAMA, vol. 285(5), pp. 545-550, 2001.*

Burke et al. Cloning of large segments of exogenous DNA into yeast by means of artificial chromosome vectors. Science, vol. 236, pp. 806-812, 1987.*

Alber et al., "Nucleotide Sequence of the Triose Phosphate Isomerase Gene of *Saccharomyces cerevisiae*," *J. Mol. Appl. Genet.* 1: 419-34 (1982).

Arbiser et al., "Regulation of Gene Expression in Choriocarcinoma by Methotrexate and Hydroxyurea," *Endocrinology* 128(2): 972-978 (1991).

Beaucage et al., "The Synthesis of Modified Oligonucleotides by the Phosphoramidite Approach and Their Application," *Tetrahedron* 49(28): 6123-6194 (1993).

Beaucage et al., "Advances in the Synthesis of Oligonucleotides by the Phosphoramidite Approach," *Tetrahedron* 48(12): 2223-2311 (1992).

Becker et al., "High-Efficiency Transformation of Yeast by Electroporation," *Methods in Enzymology* 194: 182-187 (1991).

Blau, "Current Status of Stem Cell Therapy and Prospects for Gene Therapy for the Disorders of Globin Synthesis," *Baillieres Clin. Haematol* 11:257-275 (1998).

Blouin et al., "Red Cells: Altered Hematopoiesis in Murine Sickle Cell Disease," *Blood* 94:1451-1459 (1999).

Burke et al., "Cloning of Large Segments of Exogenous DNA into Yeast by Means of Artificial Chromosome Vectors," *Science* 236: 806-812 (1987).

Chang et al, "Transgenic Knockout Mice Exclusively Expressing Human Hemoglobin S after Transfer of a 240-kb Betas-globin Yeast Artificial Chromosome: a Mouse Model of Sickle Cell Anemia," *Proc. Natl. Acad. Sci. USA* 95: 14886-14890 (1998).

Cheng et al., "In Vivo Promoter Activity and Transgene Expression in Mammalian Somatic Tissues Evaluated by Using Particle Bombardment,"*Proc. Natl. Acad. Sci. USA* 90(10): 4455-4459 (1993).

Chu et al., "Postsynthesis Functionalization of Oligonucleotides," Chapter 5 from *Methods in Molecular Biology* vol. 26: *Protocols for Oligonucleotide Conjugates*: pp. 145-165 (1994).

Chu et al., "Derivitization of Unprotected Polynucleotides," *Nucleic Acids Res.* 11(18): 6513-6529 (1983).

Compton et al., "An Improved Method for Routine Preparation of Intact Artificial Chromosome DNA (340-1000 Kb) for Transfection into Human Cells," *Nucleic Acids Res.* 27: 1762-1765 (1999).

Copeland et al., "Recombineering: A Powerful New Tool for Mouse Functional Genomics," *Nat. Rev. Genet.* 2: 769-779 (2001).

Culver et al., "Correction of Chromosomal Point Mutations in Human Cells with Bifunctional Oligonucleotides," *Nature Biotechnology* 17: 989-993 (1999).

Eckhardt-Schupp et al., "Radiation Inducible DNA Repair Processes in Eukaryotes," *Biochimie* 81: 161-171 (1999).

Ellis et al., "High Efficiency Mutagenesis, Repair, and Engineering of Chromosomal DNA Using Single-stranded Oligonucleotides," *Proc. Natl. Acad. Sci. USA* 98(12): 6742-6746 (2001).

Fabry et al., "Second Generation Knockout Sickle Mice: The Effect of HbF," *Blood* 97: 410-418 (2001).

Gamper et al., "The DNA Strand of Chimeric RNA/DNA Oligonucleotides Can Direct Gene Repair/Conversion Activity in Mammalian and Plant Cell-Free Extracts," *Nucleic Acids Res.* 28(21): 4332-4339 (2000).

Gamper et al., "A Plausible Mechanism for Gene Correction by Chimeric Oligonucleotides," *Biochem.* 39: 5808-5816 (2000).

Giraldo et al., "Size Matters: Use of YACs, BACs and PACs in Transgenic Animals," *Transgenic Res.* 10: 83-103 (2001).

Gnirke et al., "Microinjection of Intact 200- to 500-kb Fragments of YAC DNA into Mammalian Cells," *Genomics* 15: 659-667 (1993).

Gore et al., "Modifying Histones to Tame Cancer: Clinical Development of Sodium Phenylbutyrate and Other Histone Deacetylase Inhibitors," *Expert Opin Investig Drugs* 9(12): 2923-2934 (2000).

Hampsey, "A Tester System for Detecting Each of the Six Base-pair Substitutions in *Saccharomyces Cerevisiae* by Selecting for an Essential Cysteine in Iso-1-cytochrome C," *Genetics* 128: 59-67 (1991).

Hanft et al., "Acquired DNA Mutation Associated with In Vivo Hydroxyurea Exposure," *Blood* 95: 3589-3593 (2000).

Harrington et al., "Formation of de novo Centromeres and Construction of First-Generation Human Artificial Microchromosomes," *Nature Genetics* 15(4): 345-355 (1997).

Hassig et al., "Histone Deacetylase Activity Is Required for Full Transcriptional Repression by mSin3A," *Cell* 89(3): 341-347 (1997).

Heard et al., "Human XIST Yeast Artificial Chromosome Transgenes Show Partial X Inactivation Center Function in Mouse Embryonic Stem Cells," *Proc. Natl. Acad. Sci. USA* 96: 6841-6846 (1999).

Henning et al., "Human Artificial Chromosomes Generated by Modification of a Yeast Artificial Chromosome Containing Both Human Alpha Satellite and Single-Copy DNA Sequences," *Proc. Natl. Acad. Sci. USA* 96(2): 592-597 (1999).

Heyer, "The Search for the Right Partner: Homologous Pairing and DNA Strand Exchange Proteins in Eukaryotes," *Experientia* 50(3): 223-233 (1994).

Huxley,C., "Exploring Gene Function: Use of Yeast Artificial Chromosome Transgenesis," *Methods* 14: 199-210 (1998).

Hwang et al., "Dynamic Copy Choice: Steady State Between Murine Leukemia Virus Polymerase and Polymerase-dependent RNase H Activity Determines Frequency of In Vivo Template Switching," *Proc. Natl. Acad. Sci. USA* 98(21): 12209-12214 (2001).

Knauert et al., "Triplex Forming Oligonucleotides: Sequence-Specific Tools for Gene Targeting," *Hum Mol Genet.* 10(20): 2243-2251 (2001).

Kotin et al., "Site-Specific Integration by Adeno-Associated Virus," Proc. Natl. Acad. Sci. USA 87: 2211-2215 (1990).

Kren et al., "Gene Repair Using Chimeric RNA/DNA Oligonucleotides," *Seminars in Liver Disease* 19(1): 93-104 (1999).

Kuroiwa et al., "Manipulation of Human Minichromosomes to Carry Greater than Megabase-Sized Chromosome Inserts," *Nature Biotechnology* 18(10): 1086-1090 (2000).

Kuzminov, A., "DNA Replication Meets Genetic Exchange: Chromosomal Damage and Its Repair by Homologous Recombination," *Proc. Natl. Acad. Sci. USA* 98 (15): 8461-8468 (2001).

Lanzov, "Minireview: Gene Targeting for Gene Therapy: Prospects," *Molecular Genetics and Metabolism* 68: 276-282 (1999).

Li et al., "Progressive Formation of DNA Lesions in Cultured Ehrlich Ascites Tumor Cells Treated with Hydroxyurea," *Cancer Res.* 47(11): 2755-2758 (1987).

Lien et al., "Regulation of the Myeloid-cell-expressed Human GP91-PHOX Gene as Studied by Transfer of Yeast Artificial Chromosome Clones into Embryonic Stem Cells: Suppression of a Variegated Cellular Pattern of Expression Requires a Full Complement of Distant CIS Elements," *Mol. Cell Biol.* 17:2279-2290 (1997).
Liu et al., "Rad51p and Rad54p, but not Rad52p, Elevate Gene Repair in *Saccharomyces cerevisiae* Directed by Modified Single-stranded Oligonucleotide Vectors," *Nucleic Acids Res.* 31: 2742-2750 (2002).
Liu et al., "Strand Bias in Targeted Gene Repair Is Influenced by Transcriptional Activity," *Mol. Cell Biol.* 22: 3852-3863 (2002).
Malik et al., "Rapid Communication: An In Vitro Model of Human Red Blood Cell Production From Hematopoietic Progenitor Cells," *Blood* 91:2664-71 (1998).
Marks et al., "Histone Deacetylase Inhibitors: Inducers of Differentiation or Apoptosis of Transformed Cells," *J. Natl. Cancer Inst.* 92(15): 1210-1216 (2000).
Martus et al., "Quantitative Correlation Between Radiation-induced Mutagenesis in Endogenous Genes and Transgenes of Mouse Spermatogonical Stem Cells," *Environ Mol Mutagen.* 34(2-3): 216-220 (1999).
Merrill et al., "A Requirement for Recombinational Repair in *Saccharomyces cerevisiae* is Caused by DNA Replication Defects of mec1 Mutants," *Genetics* 153(2): 595-605 (1999).
Murphy, "Use of bacteriophage λ recombination functions to promote gene replacement in *Escherichia coli*," *J. Bacteriol.* 180(8): 2063-2071 (Apr. 1998).
Muyrers et al., "Point Mutation of Bacterial Artificial Chromosomes by ET Recombination," *EMBO Rep.* 1: 239-243 (2000).
Muyrers et al., "Rapid Modification of Bacterial Artificial Chromosomes by ET-recombination," *Nucleic Acids Res.* 27: 1555-1557 (1999).
Paques et al., "Multiple Pathways of Recombination Induced by Double-Strand Breaks in *Saccharonyces cerevisiae*," *Microbiol. and Molec. Biol. Rev.* 63(2): 349-404 (1999).
Parekh-Olmedo et al., "Targeted Gene Repair and its Application to Neurodegenerative Disorders," *Neuron* 33: 495-498 (2002).
Parekh-Olmedo et al., "Targeted Nucleotide Exchange in *Saccharomyces cerevisiae* Directed by Short Oligonucleotides Containing Locked Nucleic Acids," *Chem. Biol.* 9: 1073-1084 (2002).
Pierce et al., "A Positive Selection Vector for Cloning High Molecular Weight DNA by the Bacteriophage P1 System: Improved Cloning Efficacy," *Proc. Natl Acad. Sci. USA* 89(6): 2056-60 (1992).
Pierce et al., "Oligonucleotide-Directed Single-Base DNA Alterations in Mouse Embryonic Stem Cells," *Gene Ther.* 10(1): 24-33 (2003).
Politou et al., "Valproic Acid, Trichostatin and Their Combination with Hemin Preferentially Enhance Gamma-globin Gene Expression in Human Erythroid Liquid Cultures," *Haematologica* 86(7): 700-705 (2001).
Richardson et al., "Targeted Gene Correction Strategies," *Curr. Opin Mol Ther.* 3(4): 327-337 (2001).
Richon et al., "A Class of Hybrid Polar Inducers of Transformed Cell Differentiation Inhibits Histone Deacetylases," *Proc. Natl Acad. Sci. USA* 95(6): 3003-3007 (1998).
Riggs et al., "N-Butyrate Causes Histone Modification HeLa and Friend Erythroleukaemia Cells," *Nature* 268: 462-464 (1977).
Robbins et al., "Viral Vectors for Gene Therapy," *Pharmacol. Ther.* 80(1): 35-47 (1998).
Saito et al., "A Synthetic Inhibitor of Histone Deacetylase, MS-27-275, with Marked In Vivo Antitumor Activity Against Human Tumors," *Proc. Natl. Acad. Sci. USA* 96: 4592-4597 (1999).
Sambrook, J. and Russell, D.W. (2001), "Protocol 14: Phosphorylation of DNA Molecules with Protruding 5'-Hydroxyl Termini," *Molecular Cloning: A Laboratory Manual* 3rd Edition, Cold Spring Harbor Laboratory Press, Cold Spring Harbor, NY, pp. 9.66-9.69.
Sambrook, J. and Russell, D.W. (2001), "Protocol 12: End Labeling Protruding 3' Termini of Double-stranded DNA with [α-32P]Cordycepin 5'-Triphosphate or [α-32P]dideoxyATP," *Molecular Cloning: A Laboratory Manual* 3rd Edition, Cold Spring Harbor Laboratory Press, Cold Spring Harbor, NY, pp. 9.60-9.61.
Santocanale et al., "A Mec1- and Rad53-dependent Checkpoint Controls Late-firing Origins of DNA Replication," *Nature* 395: 615-618 (1998).
Schiestl et al., "High Efficiency Transformation of Intact Yeast Cells Using Single Stranded Nucleic Acids as a Carrier," *Current Genetics* 16(5&6): 339-346 (1989).

Schoner et al., "Translation of a Synthetic Two-Cistron mRNA in *Escherichia coli*," *Proc. Natl. Acad. Sci. USA* 83: 8506-8510 (1986).
Shizuya et al., "The Development and Applications of the Bacterial Artificial Chromosome Cloning System," *Keio J. Med.* 50(1): 26-30 (2000).
Shizuya et al., "Cloning and Stable Maintenance of 300-Kilobase-Pair Fragments of Human DNA in *Escherichia coli* Using an F-Factor-Based Vector," *Proc. Natl. Acad. Sci. USA* 89: 8794-8797 (1992).
Snyder, R.D., "The Role of Deoxynucleoside Triphosphate Pools in the Inhibition of DNA-excision Repair and Replication in Human Cells by Hydroxyurea," *Mutation Res.* 131(3-4): 163-172 (1984).
Spangrude et al., "Purification and Characterization of Mouse Hematopoietic Stem Cells," *Science* 214: 58-62 (1988).
Steinberg et al., "Review: Pharmacologic Modulation of Fetal Hemoglobin," *Medicine (Baltimore)* 80(5): 328-344 (Sep. 2001).
Sternberg et al., "Bacteriophage P1 Cloning System for the Isolation, Amplification, and Recovery of DNA Fragments as Large as 100 Kilobase Pairs," *Proc. Natl. Acad. Sci. USA* 87: 103-107 (1990).
Sternberg et al., "Generation of a 50,000-Member Human DNA Library with an Average DNA Insert Size of 75-100 kbp in a Bacteriophage P1 Cloning Vector," *New Biol.* 2(2):151-62 (1990).
Su et al., "A Novel Histone Deacetylase Inhibitor Identified by High-throughput Transcriptional Screening of a Compound Library," *Cancer Res.* 60: 3137 (2000).
Swaminathan et al., "Rapid Engineering of Bacterial Artificial Chromosomes Using Oligonucleotides," *Genesis* 29: 14-21 (2001).
Syvanen, A.C., "Accessing Genetic Variation: Genotyping Single Nucleotide Polymorphisms," *Nat. Rev. Genet.* 2: 930-942 (2001).
Tal, J., "Adeno-Associated Virus-Based Vectors in Gene Therapy," *J. Biomed. Sci.* 7: 279-291 (2000).
Tamura et al., "Upregulation of Interferon-alpha Receptor Expression in Hyrdroxyurea-treated Leukemia Cell Lines," *J. Investig. Med.* 45(4): 160-167 (1997).
Taricani et al., "Expression of hsp 16 in Response to Nucleotide Depletion is Regulated via the spc1 MAPK Pathway in Schizosaccharomyces Pombe," *Nucleic Acids Res.* 29(14): 3030-3040 (2001).
Taylor et al., "Review: Conservation of Eurkayotic DNA Repair Mechanisms," *Int. J. Radiat. Biol.* 74(3): 277-286 (1998).
Thacker, "A Surfeit of RAD51-like Genes?" *Trends in Genetics* 15(5): 166-168 (1999).
Thompson et al., "Homologous Recombinatorial Repair of DNA Ensures Mammalian Chromosome Stability," *Mutation Res.* 477: 131-153 (2001).
Uhlmann et al., "Antisense Oligonucleotides: A New Therapeutic Principle," *Chem. Rev.* 90(4): 543-584 (1990).
Yang et al., "In Vivo and In Vitro Gene Transfer to Mammalian Somatic Cells by Particle Bombardment," *Proc. Natl. Acad. Sci. USA* 87(24): 9568-72 (1990).
Ye et al., "Targeted Gene Correction: A New Strategy for Molecular Medicine," *Mol Med Today* 4(10): 431-437 (1998).
Yoshida et al., "Potent and Specific Inhibition of Mammalian Histone Deacetylase Both In Vivo and In Vitro by Trichostatin A*," *J. Biol. Chem.* 265: 17174-17179 (1990).
Yoshida et al., "Trichostatin A and Trapoxin: Novel Chemical Probes for the Role of Histone Acetylation in Chromatin Structure and Function," *BioEssays* 17(5): 423-430 (1995).
Yu et al., "An Efficient Recombination System for Chromosome Engineering in *Escherichia coli*," *Proc. Natl. Acad. Sci. USA* 97(11): 5978-5983 (2000).
Zhou et al., "Overexpression of Ribonucleotide Reductase in Transfected Human KB Cells Increases Their Resistance to Hydroxyurea: M2 but not M1 is Sufficient to Increase Resistance to Hydroxyurea in Transfected Cells," *Cancer Res.* 55(6):1328-1333 (1995).
Alexeev et al., "Stable and inheritable changes in genotype and phenotype of albino melanocytes induced by an RNA-DNA oligonucleotide," *Nature Biotech.* 16:1343-1346 (1998).
Campbell et al., "Homologous recombination involving small single-stranded oligonucleotides in human cells," *New Biologist* 1:223-227 (1989).
Chan et al., "Targeted correction of an episomal gene in mammalian cells by a short DNA fragment tethered to a triplex-forming oligonucleotide," *J. Biol. Chem.* 274:11541-11548 (1999).

Chan et al., "Triplex DNA: fundamentals, advances, and potential applications for gene therapy," *J. Mol. Med.* 75:267-282 (1997).

Cole-Strauss et al., "Correction of the mutation responsible for sickle cell anemia by an RNA-DNA oligonucleotide," *Science* 273:1386-1389 (1996).

Crystal, Ronald G., "Transfer of Genes to Humans: Early Lessons and Obstacles to Success," *Science* 270: 404-410 (1995).

Igoucheva et al., "Targeted gene correction by small single-stranded oligonucleotides in mammalian cells," *Gene Therapy* 8:391-399 (2001).

Kaji et al., "Gene and Stem Cell Therapies," *JAMA* 285(5): 545-550 (2001).

Kmiec et al., "Targeted gene repair in mammalian cells using chimeric RNA/DNA oligonucleotides," *Cold Spring Harbor Monograph Series* 36: 643-670 (1999).

Kren et al., "Correction of the UDP-glucuronosyltransferase gene defect in the Gunn rat model of Crigler-Najjar syndrome type I with a chimeric oligonucleotide," *Proc. Natl. Acad. Sci. USA* 96:10349-10354 (1999).

Kunzelmann et al., "Gene targeting of CFTR DNA in CF epithelial cells," *Gene Ther.* 3:859-867 (1996).

Liu et al., "In vivo gene repair of point and frameshift mutations directed by chimeric RNA/DNA oligonucleotides and modified single-stranded oligonucleotides," *Nucl. Acids Res.* 29(20): 4238-50 (2001).

Moerschell et al., "Transformation of yeast with synthetic oligonucleotides," *Proc. Natl. Acad. Sci. USA* 85:524-528 (1988).

Ørum et al., "Detection of the factor V Leiden mutation by direct allele-specific hybridization of PCR amplicons to photoimmobilized locked nucleic acids," *Clinical Chemistry* 45(11): 1898-1905 (1999).

Rando et al., "Rescue of dystrophin expression in *mdx* mouse muscle by RNA/DNA oligonucleotides," *Proc. Natl. Acad. Sci. USA* 97:5363-5368 (2000).

Rice et al., "The potential of nucleic acid repair in functional genomics," *Nature Biotech.* 19(4): 321-26 (2001).

Santisteban et al., "Three new adenosine deaminase mutations that define a splicing enhancer and cause severe and partial phenotypes: Implications for evolution of a CpG hotspot and expression of a transduced ADA cDNA," *Human Molec. Genetics* 4(11): 2081-87 (1995).

Sayers et al., "5'-3' Exonucleases in Phosphorothioate-based Oligonucleotide-directed Mutagenesis," *Nucleic Acids Research* 16(3): 791-801 (1988).

Vasquez et al., "Chromosomal mutations induced by triplex-forming oligonucleotides in mammalian cells," *Nucl. Acids Res.* 27:1176-1181 (1999).

Vasquez et al., "Specific mutations induced by triplex-forming oligonucleotides in mice," *Science* 290:530-532 (2000).

Verma et al., "Gene Therapy—Promises, Problems, and Prospects," *Nature* 389: 239-242 (1997).

Woolf et al., "Toward the therapeutic editing of mutated RNA sequences," *Proc. Natl. Acad. Sci. USA* 92: 8298-8302 (1995).

Xu et al., "Activation of human γ-globin gene expression via triplex-forming oligonucleotide (TFO)-directed mutations in the γ-globin gene 5' flanking region," *Gene* 242:219-228 (2000).

Yamamoto et al., "Strand-specificity in the transformation of yeast with synthetic oligonucleotides," *Genetics* 131:811-819 (1992).

Yanez et al., "Therapeutic gene targeting," *Gene Therapy* 5:149-159 (1998).

\* cited by examiner

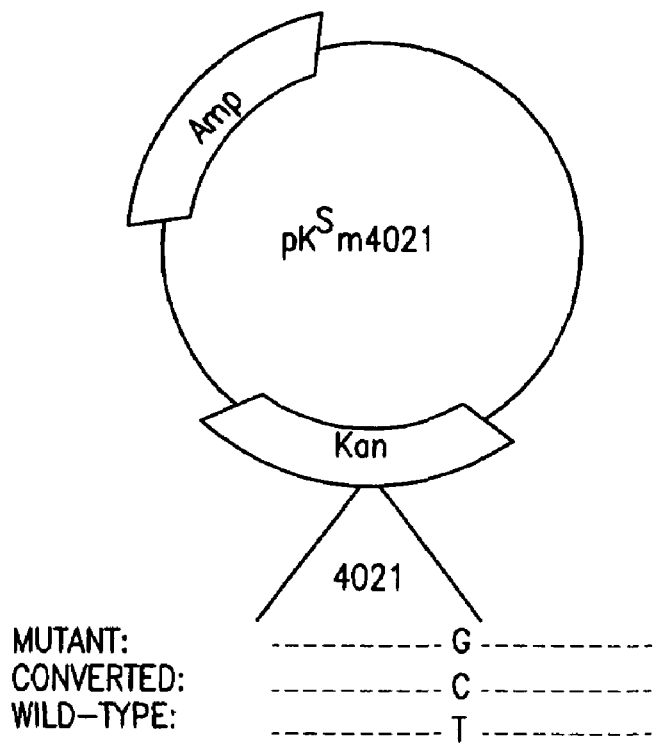
KanGG
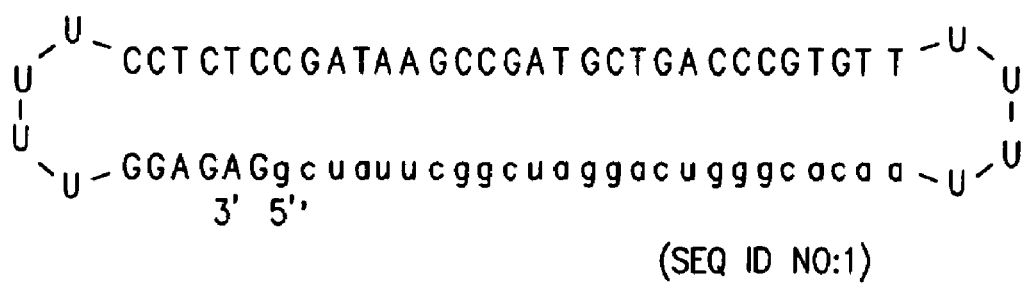
(SEQ ID NO:1)
*FIG. 1*

HygE3T/25:    5'-AGG GCG TGG ATA CGT CCT GCG GGT A-3'
              (SEQ ID NO: 7)

HygE3T/74:    5'-CTC GTG CTT TCA GCT TCG ATG TAG GAG GGC
              GTG GAT ACG TCC TGC GGG TAA ATA GCT GCG
              CCG ATG GTT TCT AC-3'    (SEQ ID NO: 8)

HygE3T/74α:   5'-GTA GAA ACC ATC GGC GCA GCT ATT TAC CCG
              CAG GAC GTA TCC ACG CCC TCC TAC ATC GAA
              GCT GAA AGC ACG AG-3'    (SEQ ID NO: 9)

HygGG/Rev:

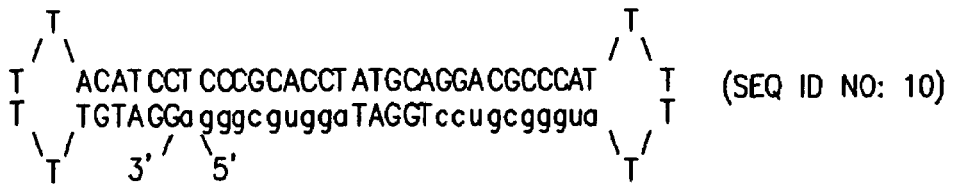

(SEQ ID NO: 10)

Kan70T:       5'-CAT CAG AGC AGC CAA TTG TCT GTT GTG CCC AGT
              CGT AGC CGA ATA GCC TCT CCA CCC AAG CGG CCG GAG
              A-3'                     (SEQ ID NO: 11)

Hyg10:    5'-ACC CGC AGG ACG TAT CCA CGC CCT-3' (SEQ ID NO: 20)
          (BOTH TERMINAL NUCLEOTIDES IN Hyg10 ARE LNA)

FIG. 3

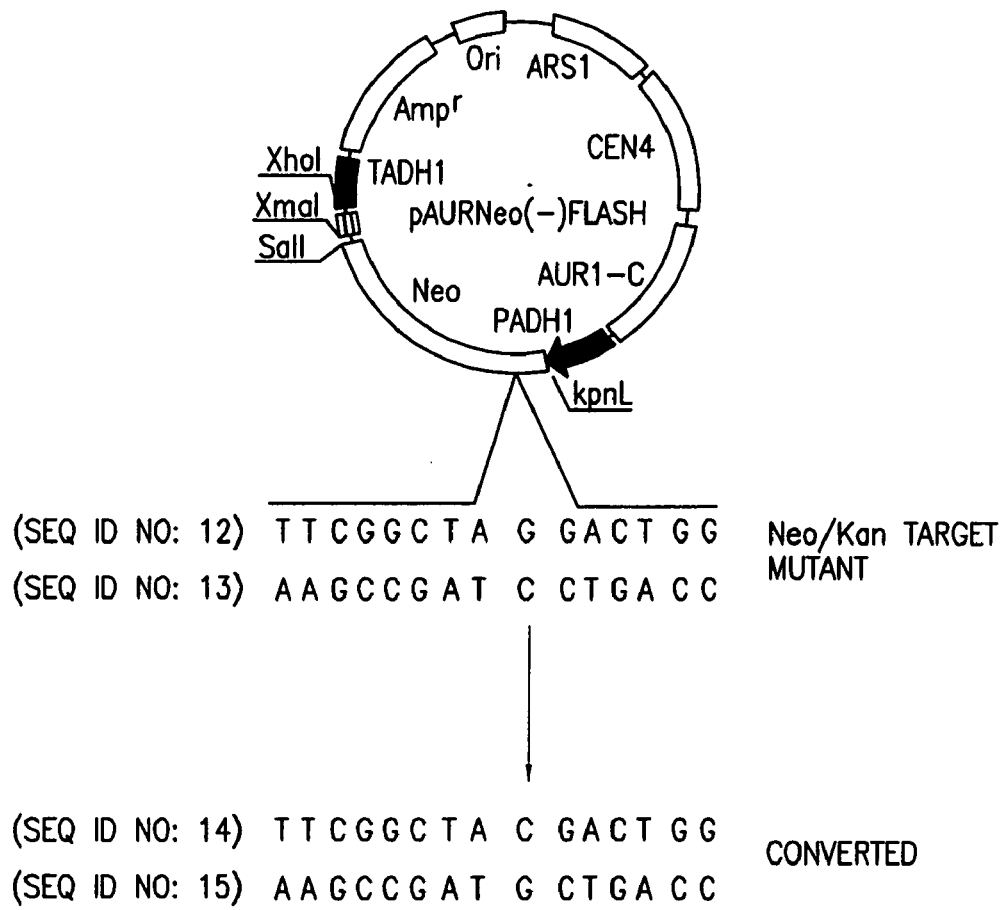
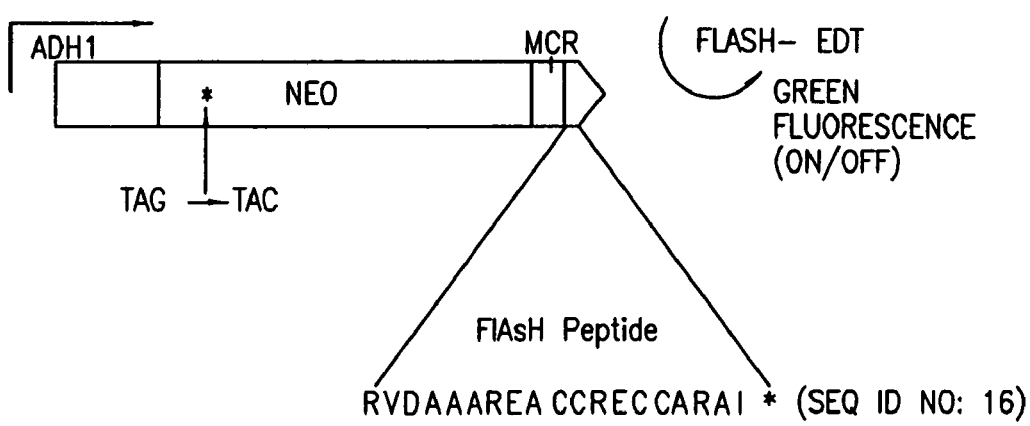
FIG. 4

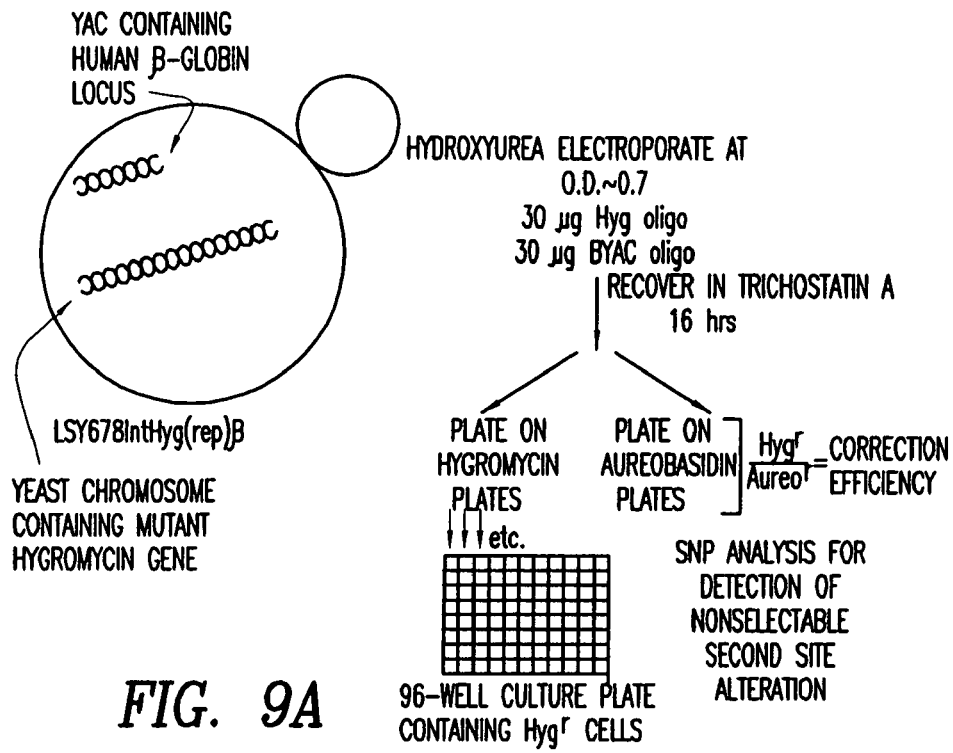
FIG. 9A
HYGROMYCIN SEQUENCE
```
wt        5'...GATGTAGGAGGGCGTGGATAIGTCCTGCGGGTAAATAGCTGC...3' (SEQ ID NO: 23)
MUTANT    5'...GATGTAGGAGGGCGTGGATAGGTCCTGCGGGTAAATAGCTGC...3' (SEQ ID NO: 24)
CONVERTED 5'...GATGTAGGAGGGCGTGGATACGTCCTGCGGGTAAATAGCTGC...3' (SEQ ID NO: 25)
Hyg3S/74NT 5' G*T*A*GAAACCATCGGCGCAGCTATTTACCCGCAGGACGT    (SEQ ID NO: 9)
           ATCCACGCCCTCCTACATCGAAGCTGAAAGCAC*G*A*G 3'
```
FIG. 9B
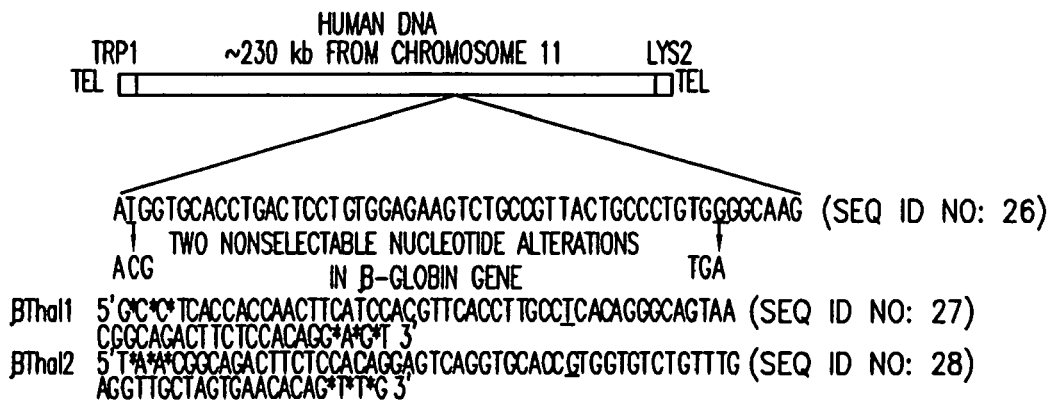
FIG. 9C

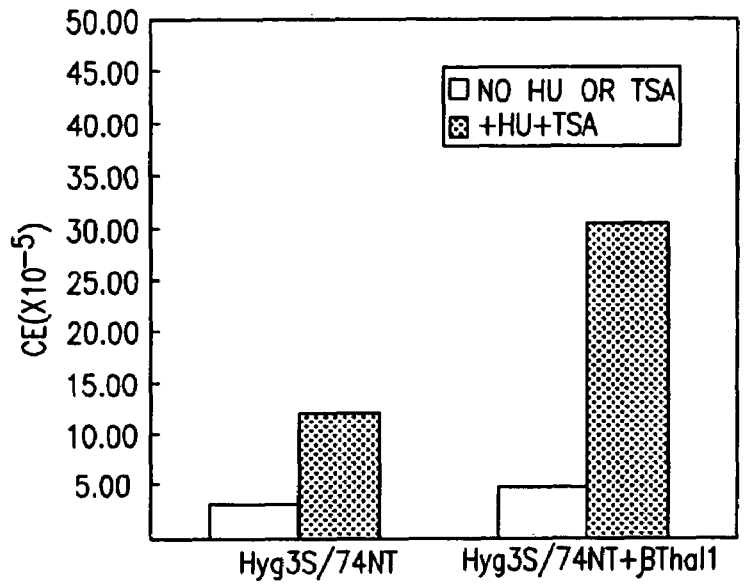
FIG. 10A
...AGTCTGCCGTTACTGCCCTGTGGGGCAA... (SEQ ID NO: 29)
...AGTCTGCCGTTACTGCCCTGTGAGGCAA... (SEQ ID NO: 30)
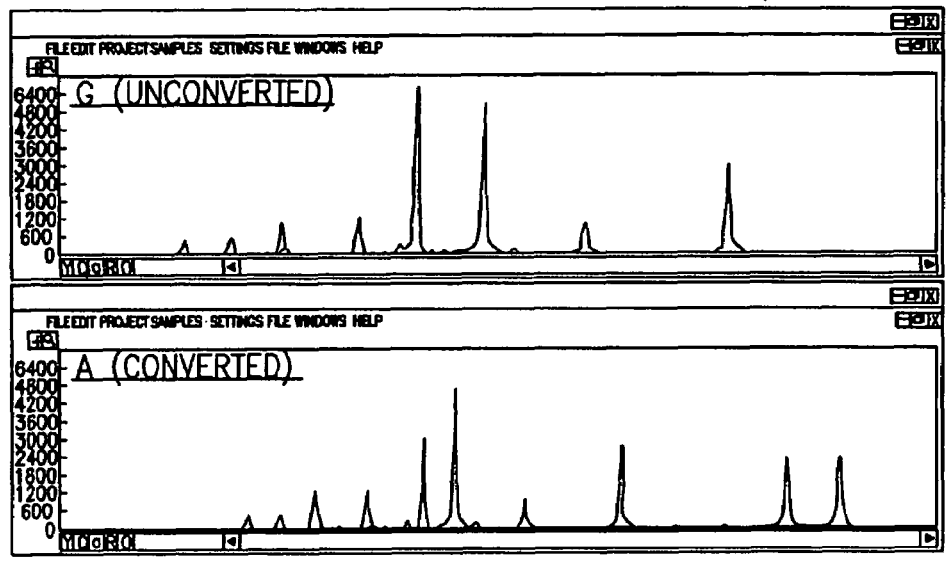
FIG. 10B

...ATGGTGCACCTGACTCCTGTGGAGAAGTCTGCC... (SEQ ID NO: 31)

...ACGGTGCACCTGACTCCTGTGGAGAAGTCTGCC... (SEQ ID NO: 32)

ENHANCED OLIGONUCLEOTIDE-MEDIATED NUCLEIC ACID SEQUENCE ALTERATION

CROSS-REFERENCE TO RELATED APPLICATIONS

This application claims benefit of priority from U.S. provisional patent application Ser. No. 60/363,341, filed Mar. 7, 2002; U.S. provisional patent application Ser. No. 60/363,053, filed Mar. 7, 2002; U.S. provisional patent application Ser. No. 60/363,054, filed Mar. 7, 2002; and U.S. provisional patent application Ser. No. 60/416,983, filed Oct. 7, 2002, the disclosures of which are incorporated herein by reference in their entireties.

FIELD OF THE INVENTION

This invention relates to oligonucleotide-directed repair or alteration of genetic information and methods, compositions, and kits for enhancing the efficiency of such alteration.

BACKGROUND OF THE INVENTION

A number of different types of oligonucleotides (and reasonably short polynucleotides) have been described for use in the targeted sequence alteration of DNA, including (i) internally duplexed chimeric RNA-DNA oligonucleotides that fold into a double-stranded, double hairpin conformation, (ii) bifunctional oligonucleotides that include a triplexing domain tethered to a repair domain, and (iii) chemically modified, single-stranded oligonucleotides that have an internally unduplexed DNA correction domain and lack both hairpins and triplexing domains. Various of these oligonucleotides have been shown to effect targeted alteration of single base pairs as well as to introduce frameshift alterations in cells and cell-free extracts from a variety of host organisms, including bacteria, fungi, plants, and animals.

The influence of factors such as growth phase, developmental state, cell cycle position, and the contribution of particular cellular proteins to the efficiency of oligonucleotide-mediated nucleic acid sequence alteration, in either cells or cell-free extracts, is not well understood. Although several cellular pathways and gene groups are known to be involved in mediating in vivo repair of DNA lesions resulting from radiation or chemical mutagenesis (including the RAD52 epistasis group of proteins, the mismatch repair group of proteins, and the nucleotide excision repair group of proteins), and although the role of these proteins in homologous recombination and maintaining genome integrity has been extensively studied (reviewed, for example, in Heyer, *Experientia* 50(3), 223-233 (1994); Thacker, *Trends in Genetics* 15(5), 166-168 (1999); Paques & Haber, *Microbiol. and Molec. Biol. Rev.* 63(2), 349-404 (1999); and Thompson & Schild, *Mutation Res.* 477, 131-153 (2001)), the specific function of these and related proteins in oligonucleotide-directed nucleic acid sequence alteration is not well understood.

Inhibitors of histone deacetylase (HDAC) induce cultured tumor cells to undergo growth arrest, differentiation, and/or apoptosis. Marks et al., *J. Natl. Canc. Inst.* 92(15), 1210-1216 (2000). For example, treatment with trichostatin A (TSA), an antibiotic from Streptomyces, results in inhibition of enzymatic activity of partially purified HDAC and accumulation of acetylated histones in various cell types, and can cause induction of Friend cell differentiation and specific inhibition of the cell cycle of normal rat fibroblasts in the G1 and G2 phases at very low concentrations. Yoshida et al., *J. Biol. Chem.* 265, 17174-17179 (1990).

HDAC inhibitors have also been suggested to affect gene therapy agents. WO 00/23567 discloses methods of promoting stem cell self-renewal that include exposure of a population of stem cells, particularly hematopoietic stem cells, to an effective dose of an HDAC inhibitor, particularly trichostatin A, trapoxin, or chlamydocin. In one embodiment, at least one transgene, either homologous or heterologous to the origin of the recipient DNA, is introduced using retroviral mediated transfer into cells treated with an HDAC inhibitor. In another embodiment, stem cells are genetically modified using a polynucleotide and treatment with an HDAC inhibitor.

WO 00/51424 discloses methods of homologous recombination in cultured non-embryonic stem cells for use as nuclear donors to produce genetically modified animals. The technique was used to insert genes, e.g., a marker gene and a transgene, at different loci using 5' and 3' regions that contain between 1.8 and 12 kb of homology at the flanking regions of an insert locus in the chromosome. Agents inhibiting histone deacetylation or factors otherwise stimulating transcription at the target locus are suggested to enhance this homologous recombination process.

WO 00/24917 discloses modification of cellular DNA in vertebrate cells by homologous pairing at preselected locations using parvoviral vectors, including vectors based on adeno-associated virus (AAV). The vectors of this technique, all of which are at least 2.7 kb in length, include a DNA sequence that is substantially identical to a target locus and all or part of at least one parvoviral inverted terminal repeated (ITR) sequence or equivalent. Among the agents disclosed to treat target cells are histone deacetylase inhibitors, such as sodium butyrate and trichostatin A.

HDAC inhibitors have not, however, been suggested or disclosed to increase the efficiency of oligonucleotide-mediated nucleic acid sequence alteration.

Recombination by bacteriophage lambda in *E. coli* bacteria during lambda's lytic cycle is mediated by the so-called "Red" recombination pathway which comprises two genes. Redα encodes an exonuclease (exo) that binds to the broken ends of double-stranded DNA and degrades one of the strands in the 5' to 3' direction, leaving a 3' single-stranded overhang. Redβ encodes a single-stranded DNA binding protein (bet) that, in combination with the bacterial RecA protein, melts duplex DNA at a site containing sequence complementary to the exposed 3' end and promotes strand invasion and annealing of the single-strand overhang into the complementary duplex. Red recombination is facilitated by the lambda protein called "Gam" which inhibits the bacterial RecBCD exonuclease, an enzyme that degrades duplex DNA with exposed ends.

Various references describe the use of the Red recombination system to mediate or facilitate homologous recombination in *E. coli* of linear double stranded DNA of non-lambda phage origin. K. C. Murphy, "Use of bacteriophage λ recombination functions to promote gene replacement in *Escherichia coli*," J. Bacteriol., 180(8):2063-2071 (Apr. 1998); Yu et al., "An efficient recombination system for chromosome engineering in *Escherichia coli*," Proc. Natl. Acad. Sci. USA, 97(11):5978-5983 (2000); Ellis et al., "High efficiency mutagenesis, repair, and engineering of chromosomal DNA using single-stranded oligonucleotides," Proc. Natl. Acad. Sci. USA, 98(12):6742-6746 (2001).

WO 02/14495 discloses methods for cloning DNA molecules and altering eukaryotic genes in cells having DNA encoding beta protein under the control of a derepressible promoter. The induced beta protein promotes homologous recombination between nucleic acids in the cell, which nucleic acids may be intrachromosomal or extrachromosomal. This publication also discloses methods for inducing homologous recombination using single-stranded DNA molecules by introducing into a cell DNA capable of undergoing homologous recombination and beta protein. The application further discloses bacterial cells that promote efficient homologous recombination, which bacteria contain one or more genes from a defective lambda prophage. However, the this publication states that at least one of the experiments used to describe the invention did not work.

Collectively, the references and international patent publication demonstrate that lambda Red gene products, and in particular beta protein, can be used in bacteria to efficiently alter DNA sequences by homologous recombination using double-stranded and single-stranded oligonucleotides. However, the references neither demonstrate nor suggest that DNA can be altered efficiently using single- or double-stranded oligonucleotides by mechanisms other than homologous recombination, and do not suggest that lambda phage proteins can be used to increase the efficiency of nucleic acid sequence alteration in non-bacterial cells by any mechanism.

Hydroxyurea (HU) is known to inhibit the M2 subunit of ribonucleotide reductase, depleting dNTP pools and impairing DNA replication, Zhou et al., Cancer Res. 55:1328-1333 (1995), which causes cells to arrest at the G1/S border of the cell cycle. HU's ability to inhibit DNA replication has lead to its use as an antiretroviral and as an antineoplastic agent. Hanft et al., Blood 95:3589-3593 (2000); Arbiser et al., Endocrinology 128:972-978 (1991); Tamura et al., J. Investig. Med. 45:160-167 (1997); Lisziewicz, U.S. Pat. No. 6,130,089. HU's ability to arrest the cell cycle at the G1/S checkpoint has been exploited to synchronize cultures of cells prior to genetic manipulations. Hadlaczky et al., WO 97/40183. HU has been shown to stimulate the expression of fetal hemoglobin and has been used to treat sickle cell disease. Steinberg & Rodgers, Medicine (Baltimore) 80:328-344 (2001).

HU has been used to increase the efficiency of retroviral-mediated gene transfer into hematopoietic stem cells. Retroviral integration is most efficient in actively cycling cells. The efficiency of this retroviral transduction is enhanced by the presence of HU in the growth medium used to prepare the target cells. See, e.g., Uchida et al., U.S. Pat. No. 5,928,638. It is believed that the effect of HU is due to its ability to switch quiescent, G0 phase, cells into the more active G1/S/G2 and M phases, giving a population enriched in actively cycling cells.

HU also has been used with adeno-associated virus (AAV) vectors. Alexander et al., U.S. Pat. No. 5,834,182. Like retroviral vectors, AAV vectors act by stably integrating into target cell's chromosome. Tal, J., J. Biomed. Sci. 7:279-291 (2000). As with retroviral transduction, AAV transduction is reported to be more efficient when target cells are pre-treated with HU.

HU has been used to increase the efficiency of nuclear transfer in transgenesis approaches in which cultured cells are first targeted by homologous recombination, and the altered nucleus than transferred. HU is used to synchronize cells prior to donor nucleus isolation, increasing the efficiency of the nuclear transfer process. Colman et al., WO 00/51424.

HU has not, however, been suggested or disclosed to be useful in increasing the efficiency of oligonucleotide-mediated nucleic acid sequence alteration.

A need exists in the art for methods, compositions, and kits to enhance the efficiency of oligonucleotide-mediated nucleic acid sequence alteration, particularly nucleic acid sequence alteration effected by other than homologous recombination. There particularly exists a need in the art for methods, compositions, and kits that can be used to increase the efficiency of oligonucleotide-mediated nucleic acid sequence alteration in eukaryotic cells, such as yeast and mammalian cells, and particularly human cells.

SUMMARY OF THE INVENTION

The present invention solves these and other needs in the art by providing, in a first aspect, improved methods of oligonucleotide-mediated targeted nucleic acid sequence alteration. The methods, which increase the efficiency of oligonucleotide-mediated nucleic acid sequence alteration, comprise combining a target nucleic acid in the presence of cellular repair proteins with a sequence-altering targeting oligonucleotide, and either adding lambda beta protein additionally to said combination or first contacting the cells having said cellular repair proteins with an HDAC inhibitor or hydroxyurea.

The target nucleic acid and sequence-altering oligonucleotide may be combined ex vivo or in vivo.

In some ex vivo embodiments, one or more of the cellular repair proteins is a purified protein, wherein purified intends that the protein is at a higher concentration relative to nonrepair proteins than is found naturally in the cell from which it is drawn. Such purified cellular repair proteins may be separately purified, or purified collectively. In other ex vivo embodiments, the cellular repair proteins are present in a cell-free protein extract.

In other embodiments, the cellular repair proteins are present within an intact cell, either cultured ex vivo or within a living organism.

The cellular repair proteins may be from a prokaryotic or eukaryotic cell, including *E. coli* cell, yeast cell, such as *Saccharomyces cerevisiae*, *Ustilago maydis*, or *Candida albicans*, a plant cell, or an animal cell, such as a mammalian cell, including mouse, hamster, rat, and monkey cell, and further including human cells. The human cell may be selected, for example, from the group consisting of liver cell, lung cell, colon cell, cervical cell, kidney cell, epithelial cell, cancer cell, stem cell, hematopoietic stem cell, hematopoietic committed progenitor cell, and embryonic stem cell, but is not so limited.

In one series of embodiments, the sequence altering oligonucleotide is a chemically modified, nonhairpin, internally unduplexed oligonucleotide.

The oligonucleotide may, for example, be fully complementary in sequence to the sequence of a first strand of the nucleic acid target, but for one or more mismatches as between the sequences of the oligonucleotide and its complement on the target nucleic acid first strand, and possess at least one terminal modification. In particularly useful embodiments, the oligonucleotide has an internally unduplexed domain of at least 8 contiguous deoxyribonucleotides, and the one or more mismatches are positioned exclusively in the oligonucleotide DNA domain and at least 8 nucleotides from the oligonucleotide's 5' and 3' termini.

Usefully, the terminal modification is selected from the group consisting of at least one terminal locked nucleic acid (LNA), at least one terminal 2'-O-Me base analog, and at least one, two, three or more terminal phosphorothioate linkages, and the oligonucleotide is 17-121 nucleotides in length, often no more than 74 nucleotides in length.

The target may be double-stranded DNA, such as genomic DNA, including genomic DNA in a chromosome. The chromosome may be a natural or artificial chromosome. In other embodiments, the DNA target is episomal.

In some embodiments of the methods of the present invention, the target nucleic acid is the nontranscribed strand of a double-stranded genomic DNA. In others, the target nucleic acid is the transcribed strand.

In a second aspect, the invention provides compositions for oligonucleotide-mediated targeted nucleic acid sequence alteration.

The compositions comprise a sequence altering oligonucleotide which is capable, when combined in the presence of cellular repair proteins with a substantially complementary target nucleic acid, of effecting targeted sequence alteration therein; and either (i) cellular repair proteins, the cellular proteins derived from a cell prior-contacted with an HDAC inhibitor or hydroxyurea, or (ii) lambda beta protein.

As in the methods above-described, the cellular repair proteins of the composition may be purified, present in a cell-free protein extract, or present within an intact cell, either cells present in culture or within an intact animal.

In other embodiments, the composition may additionally, or in the alternative, comprise trichostatin A, cellular repair proteins, or hydroxyurea.

In another aspect, the invention provides a kit.

The kit may comprise an oligonucleotide, particularly a sequence-altering oligonucleotide, such as a chemically modified, internally unduplexed, nonhairpin oligonucleotide, and one or more of trichostatin A, lambda beta protein, or hydroxyurea, separately packaged therefrom.

The kit may comprise an oligonucleotide, particularly a sequence-altering oligonucleotide, such as a chemically modified, internally unduplexed, nonhairpin oligonucleotide, and cellular repair proteins, the cellular proteins derived from a cell prior-contacted with an HDAC inhibitor or hydroxyurea and packaged separately therefrom. Such kits may further comprise lambda beta protein.

Kits may comprise at least one protein from the RAD52 epistasis group, the mismatch repair group, or the nucleotide excision repair group and may additionally comprise trichostatin A, lambda beta protein, or hydroxyurea, optionally with an oligonucleotide having sequence alteration activity.

In yet other embodiments, particularly suited to preparing sequence altering oligonucleotides having one or more locked nucleic acid (LNA) residues, the kits of the present invention may comprise a template-independent single-strand polymerase, such as calf thymus terminal deoxynucleotidyl transferase; LNA monomers having 5'-triphosphates; and trichostatin A, lambda beta protein, or hydroxyurea. In other embodiments, the kits may comprise a water soluble carbodiimide composition; an imidazole composition; LNA monomers having a nucleophilic group; and Trichostatin A, lambda beta protein, or hydroxyurea.

Further aspects and embodiments of the instant invention are summarized in the following numbered items:

1. A method of oligonucleotide-mediated targeted nucleic acid sequence alteration, the method comprising:
   combining a target nucleic acid in the presence of cellular repair proteins with a sequence-altering targeting oligonucleotide; and
   either adding lambda beta protein additionally to said combination or first contacting the cells having said cellular repair proteins with an HDAC inhibitor or hydroxyurea.
2. The method of item 1, wherein said cellular repair proteins are purified.
3. The method of item 1, wherein said cellular repair proteins are present in a cell-free protein extract.
4. The method of item 1, wherein said cellular repair proteins are present within an intact cell.
5. The method of item 4, wherein said cell is cultured ex vivo.
6. The method of item 4, wherein said cell is within a living organism.
7. The method of item 1, wherein said cellular repair proteins are of a cell selected from the group consisting of: prokaryotic cells and eukaryotic cells.
8. The method of item 7, wherein said cell is a prokaryotic cell.
9. The method of item 8, wherein said prokaryotic cell is a bacterial cell.
10. The method of item 9, wherein said bacterial cell is an *E. coli* cell.
11. The method of item 7, wherein said cell is a eukaryotic cell.
12. The method of item 11, wherein said eukaryotic cell is a yeast cell, plant cell, mammalian cell, or human cell.
13. The method of item 12, wherein said eukaryotic cell is a yeast cell.
14. The method of item 13, wherein said yeast is *Saccharomyces cerevisiae, Ustilago maydis*, or *Candida albicans*.
15. The method of item 12, wherein said eukaryotic cell is a plant cell.
16. The method of item 12, wherein said eukaryotic cell is a human cell.
17. The method of item 16, wherein said human cell is selected from the group consisting of liver cell, lung cell, colon cell, cervical cell, kidney cell, epithelial cell, cancer cell, stem cell, hematopoietic stem cell, hematopoietic committed progenitor cell, and embryonic stem cell.
18. The method of item 12, wherein said eukaryotic cell is a mammalian cell.
19. The method of item 18, wherein said mammal is selected from the group consisting of: mouse, hamster, rat, and monkey.
20. The method of any one of items 1-19, wherein said oligonucleotide is fully complementary in sequence to the sequence of a first strand of the nucleic acid target, but for one or more mismatches as between the sequences of said oligonucleotide and its complement on said target nucleic acid first strand, and wherein said oligonucleotide has at least one terminal modification.
21. The method of item 20, wherein said at least one terminal modification is selected from the group consisting of: at least one terminal locked nucleic acid (LNA), at least one terminal 2'-O-Me base analog, and at least one terminal phosphorothioate linkage.
22. The method of item 21, wherein said oligonucleotide is a single-stranded oligonucleotide 17-121 nucleotides in length, has an internally unduplexed domain of at least 8 contiguous deoxyribonucleotides, and wherein said one or more mismatches are positioned exclusively in said oligonucleotide DNA domain and at least 8 nucleotides from said oligonucleotide's 5' and 3' termini.
23. The method of item 21, wherein said oligonucleotide has at least one terminal locked nucleic acid (LNA).
24. The method of item 1, wherein said oligonucleotide is at least 25 nucleotides in length.
25. The method of item 1, wherein said oligonucleotide is no more than 74 nucleotides in length.
26. The method of item 1, wherein said oligonucleotide is no more than 121 nucleotides in length.
27. The method of item 1, wherein said target nucleic acid is DNA.

28. The method of item 27, wherein said DNA is double-stranded DNA.
29. The method of item 28, wherein said double-stranded DNA is genomic DNA.
30. The method of item 29, wherein said genomic DNA is in a chromosome.
31. The method of item 30, wherein said chromosome is an artificial chromosome.
32. The method of item 29, wherein said genomic DNA is episomal.
33. The method of item 1, wherein said target nucleic acid is the nontranscribed strand of a double-stranded genomic DNA.
34. A composition for enhanced oligonucleotide-mediated targeted nucleic acid sequence alteration, comprising:
an oligonucleotide, said oligonucleotide capable, when combined in the presence of cellular repair proteins with a substantially complementary target nucleic acid, of effecting targeted sequence alteration therein; and
either cellular repair proteins, said cellular proteins derived from a cell prior-contacted with an HDAC inhibitor or hydroxyurea, or lambda beta protein.
35. The composition of item 34, wherein said cellular repair proteins are purified.
36. The composition of item 34, wherein said cellular repair proteins are present in a cell-free protein extract.
37. The composition of item 34, wherein said cellular repair proteins are present within an intact cell.
38. The composition of any one of items 34-37, wherein said cell is selected from the group consisting of: prokaryotic cells and eukaryotic cells.
39. The composition of item 38, wherein said cell is a prokaryotic cell.
40. The composition of item 39, wherein said prokaryotic cell is a bacterial cell.
41. The composition of item 40, wherein said bacterial cell is an *E. coli* cell.
42. The composition of item 38, wherein said cell is a eukaryotic cell.
43. The composition of item 42, wherein said eukaryotic cell is a yeast cell, plant cell, human cell, or a mammalian cell.
44. The composition of item 43, wherein said eukaryotic cell is a yeast cell.
45. The composition of item 44, wherein said yeast is *Saccharomyces cerevisiae, ustilago maydis*, or *Candida albicans*.
46. The composition of item 43, wherein said eukaryotic cell is a plant cell.
47. The composition of item 43, wherein said eukaryotic cell is a human cell.
48. The composition of item 47, wherein said human cell is selected from the group consisting of liver cell, lung cell, colon cell, cervical cell, kidney cell, epithelial cell, cancer cell, stem cell, hematopoietic stem cell, hematopoietic committed progenitor cell, and embryonic stem cell.
49. The composition of item 43, wherein said eukaryotic cell is a mammalian cell.
50. The composition of item 49, wherein said mammal is selected from the group consisting of: mouse, hamster, rat, and monkey.
51. The composition of any one of items 34-50, wherein said oligonucleotide has at least one terminal modification.
52. The composition of item 51, wherein said at least one terminal modification is selected from the group consisting of: at least one terminal locked nucleic acid (LNA), at least one terminal 2'-O-Me base analog, and at least one terminal phosphorothioate linkage.
53. The composition of item 52, wherein said oligonucleotide has at least one terminal locked nucleic acid (LNA).
54. The composition of any one of items 34-53, wherein said oligonucleotide is a single-stranded oligonucleotide 17-121 nucleotides in length, and has an internally unduplexed domain of at least 8 contiguous deoxyribonucleotides.
55. The composition of any one of items 34-54, wherein said oligonucleotide is at least 25 nucleotides in length.
56. The composition of any one of items 34-55, wherein said oligonucleotide is no more than 121 nucleotides in length.
57. The composition of any one of items 34-56, wherein said oligonucleotide is no more than 74 nucleotides in length.
58. The composition of any one of items 34-57, further comprising: trichostatin A, protein extract, or hydroxyurea.
59. A kit, comprising:
an oligonucleotide; and
trichostatin A, lambda beta protein, or hydroxyurea.
60. A kit, comprising:
an oligonucleotide; and
cellular repair proteins, said cellular proteins derived from a cell prior-contacted with an HDAC inhibitor or hydroxyurea.
61. A kit, comprising:
an oligonucleotide;
cellular repair proteins; and
lambda beta protein.
62. A kit, comprising:
at least one protein from the RAD52 epistasis group, the mismatch repair group, or the nucleotide excision repair group; and
trichostatin A, lambda beta protein, or hydroxyurea.
63. The kit according to item 62, further comprising:
an oligonucleotide having nucleic sequence alteration activity.
64. A kit, comprising:
a template-independent single-strand polymerase;
LNA monomers having 5'-triphosphates; and
trichostatin A, lambda beta protein, or hydroxyurea.
65. The kit according to item 64, wherein said polymerase is calf thymus terminal deoxynucleotidyl transferase.
66. A kit, comprising:
a water soluble carbodiimide composition;
an imidazole composition;
LNA monomers having a nucleophilic group; and
Trichostatin A, lambda beta protein, or hydroxyurea.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout.

FIG. 1. Genetic readout system for correction of a point mutation in plasmid pK$^S$m4021. A mutant kanamycin gene harbored in plasmid pK$^S$m4021 is the target for correction by oligonucleotides. The mutant G is converted to a C by the action of the oligonucleotide. Corrected plasmids confer resistance to kanamycin in *E. coli* (DH10B) after electroporation leading to the genetic readout and colony counts. The sequence of chimeric, RNA-DNA double-hairpin oligonucleotide KanGG is shown (SEQ ID NO: 1).

FIG. 3. Oligonucleotides for correction of hygromycin resistance gene. The sequence of the oligonucleotides used in experiments to assay correction of a hygromycin resistance gene are shown. DNA residues are shown in capital letters, RNA residues are shown in lowercase and nucleotides with a phosphorothioate backbone are capitalized and underlined. In FIG. 3, the sequence of HygE3T/25 corresponds to SEQ ID NO: 7, the sequence of HygE3T/74T (also known as HygE3T/74 and Hyg3S/74T) corresponds to SEQ ID NO:8, the sequence of HygE3T/74NT (also known as HygE3T/74a and Hyg3S/74NT) corresponds to SEQ ID NO: 9, the sequence of HygGG/Rev corresponds to SEQ ID NO: 10 and the sequence of Kan70T corresponds to SEQ ID NO: 11; the sequence of Hyg10 corresponds to SEQ ID NO:20.

FIG. 4. pAURNeo(-)FlAsH™ plasmid. This figure describes the plasmid structure, target sequence, oligonucleotides, and the basis for detection of the nucleic acid sequence alteration event by fluorescence. The sequences of the Neo/ Kan target mutant and its complement correspond to SEQ ID NO: 12 and SEQ ID NO: 13, the converted sequence and its complement correspond to SEQ ID NO: 14 and SEQ ID NO: 15 and the FlAsH™ peptide sequence corresponds to SEQ ID NO: 16.

FIGS. 8A and 8B illustrate the construction scheme for the pAUR101-HYG(x)eGFP integrational plasmid.

FIG. 9. Dual targeting protocol. (A) Schematic diagram of the generalized strategy for dual targeting. (B) Sequences of the hygromycin-resistance gene and its mutation. The wild-type ("wt") (SEQ ID NO: 23), mutant (SEQ ID NO: 24), and converted (SEQ ID NO: 25) sequences are shown, together with the sequence-altering oligonucleotide used to generate the conversion ("Hyg3S/74NT") (SEQ ID NO: 9) (C) Schematic of the YAC containing the human β-globin locus, the segment of the β-globin gene in which the alterations are made (SEQ ID NO: 26) and the oligonucleotides used to generate the nonselectable alterations: "Thal1" (SEQ ID NO: 27) and "βThal2" (SEQ ID NO: 28).

FIG. 10. Dual targeting results. (A) Efficiency of gene editing of hygromycin mutation using the dual targeting protocol. For these experiments, YAC-containing LSY678IntHyg(rep)β cells are grown in the presence of HU, electroporated with the selectable and nonselectable oligonucleotides, and allowed to recover in the presence of TSA. (B) Gene editing of the human β-globin gene directed by the βThal1 oligonucleotide, including the sequence of the altered segment before (SEQ ID NO: 29) and after (SEQ ID NO: 30) the conversion.

DETAILED DESCRIPTION OF THE INVENTION

Figure 2:
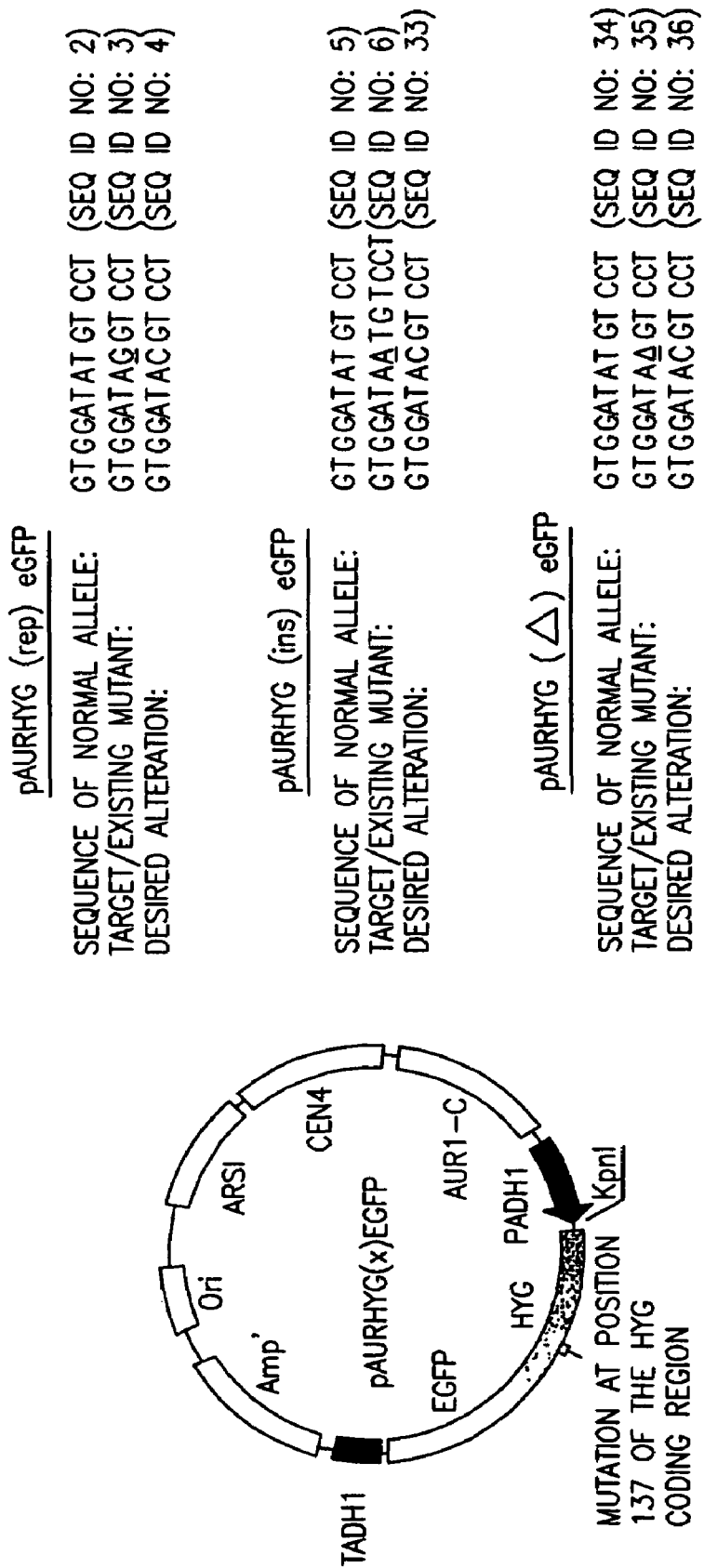
FIG. 2. Hygromycin-eGFP target plasmids. Diagram of plasmid pAURHYG(x)eGFP. Plasmid pAURHYG(rep) eGFP contains a base substitution mutation introducing a G at nucleotide 137, at codon 46, of the Hygromycin B coding sequence (cds). Plasmid pAURHYG(ins)eGFP contains a single base insertion mutation between nucleotides 136 and 137, at codon 46, of the Hygromycin B coding sequence (cds) which is transcribed from the constitutive ADH1 promoter. Plasmid pAURHYG(Δ)eGFP contains a deletion mutation removing a single nucleotide at codon 46, of the Hygromycin B coding sequence (cds). The sequence of the normal allele, the target (existing mutant), and desired alteration is shown for each o the three plasmids.

The present invention provides methods, compositions, and kits for increasing the efficiency of oligonucleotide-mediated nucleic acid sequence alteration.

The methods comprise administering to a cell or tissue from a bacterium, a fungus, a plant, or an animal, including mammals, an agent or agents such as an HDAC inhibitor, a composition comprising beta protein, or hydroxyurea, and concurrently, or at some time thereafter, administering to the treated cell or tissue an oligonucleotide having nucleic acid sequence alteration activity.

Although HDAC inhibitors have been used to facilitate homologous recombination and viral-mediated gene transfer, and although lambda beta protein has been shown to facilitate homologous recombination between nucleic acids in E. coli cells, which nucleic acids may be intrachromosomal or extrachromosomal, and although HU has been used to enhance the efficiency of gene targeting by viral transduction and nuclear transfer, prior to the invention described herein it was unknown and could not be predicted whether these agents could be used to enhance the efficiency of oligonucleotide-mediated nucleic acid sequence alteration.

Oligonucleotide-mediated nucleic acid sequence alteration is mediated by cellular proteins different from those that mediate homologous recombination. The oligonucleotides used for oligonucleotide-mediated gene alteration typically lack structures, such as long stretches of sequence complementarity to the target, that are required for homologous recombination. And oligonucleotide-mediated nucleic acid sequence alteration does not involve the intermediation of viral proteins.

The genetic products resulting from oligonucleotide-mediated sequence alteration, on the one hand, differ from those resulting from either homologous recombination or virally-mediated transduction, on the other.

Homologous recombination results in the replacement of large stretches of the chromosomal DNA of the target cell with sequences from a transgene supplied on an episomal DNA construct, utilizing the target cell's homologous recombination machinery to effect the required double strand breakage and rejoining. Flanking sequence on the 3' and 5' regions of the transgene, designed to match sequences flanking the target insertion site, are usually extensive, e.g., between about 1.5 to 15 kb.

Retroviral and adeno-associated virus transduction involve infection of target cells with recombinant viral vectors, often relying on virally encoded proteins to effect integration of the virus into the host's chromosome. Robbins & Ghivizzani, Pharmacol. Ther. 80:35-47 (1998). Moreover, the chromosome of the target cell after such viral transduction contains an insertion of the entire, or substantial portions of the, recombinant virus, including viral vector sequences. Viral integration may be multiplicative with tandem or multiple copies of integrated virus. Integration occurs at a random spot in the host chromosome, or at a known and predetermined viral integration site. The variation in insertion site and number results in variation in transgene expression. The viral remnants inserted in the chromosome potentially can lead to adverse immune responses to expressed viral proteins and may also, depending on their site of alteration, cause neoplastic changes.

In contrast, oligonucleotide-mediated nucleic acid sequence alteration uses different reagents and produces results different from those used in homologous recombination and viral transduction. Oligonucleotide-mediated nucleic acid sequence alteration involves the use of relatively short oligonucleotides, rather than exogenously supplied genes or viral vectors, to modify genes within the target cell. The host chromosomal DNA sequence is altered at only one or a few bases, at precisely defined locations within the target gene. No viral sequences or episomal remnants are introduced into the host chromosome, and no virally encoded proteins are required. Thus, there is no need to introduce episomal vectors containing entire genes (or at least long portion of genes), as is required for gene targeting by homologous recombination.

Oligonucleotide-mediated gene alteration is mechanistically distinct from homologous recombination and viral transduction as well. Oligonucleotide-mediated gene alteration is dependent on the cellular DNA mismatch repair mechanism, a cellular pathway distinct from homologous recombination and viral transduction, involving separate genes and gene products. Lanzov, Molecular Genetics and Metabolism 68:276-282 (1999). For example, while homologous recombination requires the RAD52 gene product (Kuzminov, Proc. Natl. Acad. Sci. USA 98 (15): 8461-8468 (2001)), oligonucleotide-mediated gene alteration is more efficient in the absence of RAD52.

It was further unknown and could not be predicted whether lambda beta protein could be used to enhance the efficiency of oligonucleotide-mediated nucleic acid sequence alteration in cells other than the natural host of the lambda phage.

We have now discovered, surprisingly, that despite the difference in mechanisms as between oligonucleotide-mediated sequence alteration, on the one hand, and homologous recombination and viral transduction on the other, that prior or contemporaneous treatment of cells with the HDAC inhibitor trichostatin A or with hydroxyurea increases the efficiency of oligonucleotide-mediated sequence alteration. We have further discovered that despite the difference in mechanisms as between oligonucleotide-mediated sequence alteration, on the one hand, and homologous recombination on the other, and despite the difference in proteins and intracellular milieu as between E coli, on the one hand, and eukaryotic cells, on the other, that lambda beta protein surprisingly increases the efficiency of oligonucleotide-mediated sequence alteration in all cells tested.

Accordingly, the invention provides methods, compositions, and kits for increasing the efficiency of oligonucleotide-mediated nucleic acid sequence alteration. The methods comprise treating a cell or tissue from a bacterium, a fungus, a plant, or an animal with an HDAC inhibitor or hydroxyurea, and then administering to the treated cell or tissue an oligonucleotide having nucleic acid sequence alteration activity, or treating a cell or tissue from a bacterium, a fungus, a plant, or an animal simultaneously with lambda beta protein and an oligonucleotide having nucleic acid sequence alteration activity.

The methods, compositions, and kits of the present invention can be used with any oligonucleotide having nucleic acid sequence alteration activity. All such oligonucleotides comprise at least a portion that is fully complementary in sequence to the sequence of a portion of a nucleic acid target, except for noncomplementary bases designed to direct nucleic acid sequence alteration. Thus, the oligonucleotides used in the methods of the invention have at least one base pair different from the sequence of a target gene, or have at least one base pair different from the complement of the DNA sequence of a target gene.

For example, the methods, compositions, and kits of the present invention can be used with bifunctional oligonucleotides having both a triplex forming domain and repair domain, as described in Culver et al., Nat. Biotechnol. 1999 October;17(10):989-93, and other types of sequence-altering triplexing oligonucleotides such as those described in U.S. Pat. Nos. 6,303,376, 5,962,426, and 5,776,744, the disclosures of which are incorporated herein by reference in their entireties. See also Knauert et al., Hum Mol Genet. 2001 October 1;10(20):2243-51, the disclosure of which is incorporated herein by reference in its entirety.

Because triplexing oligonucleotides bind to DNA using Hoogstein or reverse Hoogstein base-pairing rules, rather than Watson-Crick base-pairing rules, triplexing oligonucleotides used for oligonucleotide-mediated sequence alteration typically include one or more Watson-Crick mismatches, as compared to the target desired to be altered, within 8 nucleotides, often within 7, 6, 5, 4, 3, 2 or even 1 nucleotides of one or both of the oligonucleotide's termini.

The methods, compositions, and kits of the present invention can also be used with chimeric RNA-DNA double hairpin oligonucleotides, as are described, inter alia, in U.S. Pat. Nos. 5,945,339, 5,888,983, 5,871,984, 5,795,972, 5,780,296, 5,760,012, 5,756,325, 5,731,181, and 5,565,350, the disclosures of which are incorporated herein by reference in their entireties. See also Ye et al., Mol Med Today 1998 October; 4(10):431-7 and Richardson et al., Curr. Opin Mol Ther. 2001 August;3(4):327-37 for review.

Internal sequence complementarity within the sequence-altering chimeric oligonucleotide leads to folding of the single-stranded oligonucleotide into an internally self-duplexed form that includes two hairpins. Mismatches as compared to target are within a duplexed region. The sequence-altering chimeric oligonucleotides comprise both deoxyribose and ribose containing bases, and thus contain regions of both DNA and RNA; the 2'-hydroxyl of the ribonucleotides of the oligonucleotide may be methylated.

Nonnatural nucleobases can be present within such chimeric oligonucleotides (and in the single-stranded, chemically modified, internally unduplexed oligonucleotides further described herein below). In the present context, the term "nucleobase" covers naturally occurring nucleobases as well as non-naturally occurring nucleobases. As would be apparent, various nucleobases which previously have been considered "nonnaturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosine, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-S-methyl-4-triazolopyridine, isocytosine, isoguanine, inosine and the "non-naturally occurring" nucleobases described in U.S. Pat. No. 5,432,272. The term "nucleobase" is intended to cover each of these examples as well as analogues and tautomers thereof.

The methods, compositions and kits of the present invention can also be used to increase the frequency and efficiency of oligonucleotide-mediated nucleic acid sequence alteration using chemically-modified, single-stranded, internally unduplexed oligonucleotides, as are described, inter alia, in U.S. Pat. No. 6,271,360; international patent publications nos. WO 01/73002, WO 01/92512, and WO 02/10364; Pierce et al., Gene Ther. 10(1):24-33 (2003); Parekh-Olmedo et al., Chem Biol. 9(10):1073-84 (2002); Liu et al., Nucleic Acids Res. 30(13):2742-50 (2002); and Gamper et al., Nucleic Acids Res. 28(21):4332-9 (2000), the disclosures of which are incorporated herein by reference in their entireties.

Particularly useful single-stranded chemically modified oligonucleotides are those that are 17 - 121 nucleotides in length and that have an internally unduplexed deoxyribonucleotide "alteration" domain, which domain is typically, but not invariably, at least 8 nucleotides in length. Mismatches as between the sequence of the oligonucleotide and its target are positioned within the internally unduplexed DNA domain, and are typically, although not invariably, at least 8 nucleotides from the oligonucleotide's 5' and 3' termini. The oligonucleotide is fully complementary in sequence to the sequence of a first strand of the nucleic acid target, but for one or more mismatches as between the sequences of the deoxyribonucleotide alteration domain and its complement on the target nucleic acid first strand. Additionally, the oligonucleotide has at least one terminal modification selected from the group consisting of: at least one terminal locked nucleic acid (LNA), at least one terminal 2'-O-Me base analog, and at least one terminal phosphorothioate linkages. Typically, at least one of the at least one modification is located at a terminus of the oligonucleotide. Often, a plurality of such modifications are present, such as 2, 3, 4 or more phosphorothioate linkages at one or both termini.

Although 2'-O-methyl residues are ribonucleic acids, the single-stranded chemically modified oligonucleotides differ from the "chimeric" oligonucleotides above-described by positioning the mismatch, as compared to target, within an internally unduplexed DNA domain. Furthermore, the single-stranded chemically modified oligonucleotides lack the hairpin structures found in the sequence altering chimeric oligonucleotides above-described (i.e., they are "nonhairpin" molecules).

A particularly useful chemical modification to be included when the methods, compositions, and kits of the present invention are used to enhance or increase the frequency of sequence alteration by single-stranded chemically modified oligonucleotides, is the inclusion of one or more monomers from the class of synthetic molecules known as locked nucleic acids (LNAs). LNAs are bicyclic and tricyclic nucleoside and nucleotide analogues and the oligonucleotides that contain such analogues. The basic structural and functional characteristics of LNAs and related analogues are disclosed in various publications and patents, including WO 99/14226, WO 00/56748, WO 00/66604, WO 98/39352, U.S. Pat. No. 6,043,060, and U.S. Pat. No. 6,268,490, all of which are incorporated herein by reference in their entirety.

The general LNA structure may be described by the following formula:

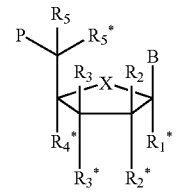

wherein X is selected from —O—, —S—, —N($R^{N*}$)—, —C($R^6R^{6*}$)—, —O—C($R^7R^{7*}$)—, —C($R^6R^{6*}$)—O—, —S— C($R^7R^{7*}$)—, —C($R^6R^{6*}$)—S—, —N($R^{N*}$)—C($R^7R^{7*}$)—, —C($R^6R^{6*}$)—N($R^{N*}$)—, and —C($R^6R^{6*}$)—C($R^7R^{7*}$)—; B is selected from hydrogen, hydroxy, optionally substituted $C_{1-4}$-alkoxy, optionally substituted $C_{1-4}$-alkyl, optionally substituted C1-4-acyloxy, and the nucleobases; P designates an internucleoside linkage to an adjacent monomer, or a 5'-terminal group, such internucleoside linkage or 5'-terminal group optionally including the substituent $R^5$; one of the substituents $R^2$, $R^{2*}$, $R^3$, and $R^{3*}$ is a group P* which designates an internucleoside linkage to an adjacent monomer, or a 3'-terminal group; one or two pairs of non-geminal substituents selected from the present substituents of $R^{1*}$, $R^{4*}$, $R^5$, $R^{5*}$, $R^6$, $R^{6*}$, $R^7$, $R^{7*}$, $R^{N*}$, and the ones of $R^2$, $R^{2*}$, $R^3$, and $R^{3*}$ not designating P* each designates a covalent bridging moiety consisting of one or more of the following substituents: —C($R^aR^b$)—, —C($R^a$)=C($R^b$)—, —C($R^a$)=N—, —O—, —Si($R^aR^b$)—, —S—, —$SO_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di-($C_{1-6}$-alkyl)amino, carbamoyl, mono- and di-($C_{1-6}$-alkyl)aminocarbonyl, amino-$C_{1-6}$-alkylaminocarbonyl, mono- and di-($C_{1-6}$-alkyl)amino-$C_{1-6}$-alkylaminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, and the halogens, where aryl and heteroaryl may be optionally substituted, and where two geminal substituents $R^a$ and $R^b$ together may designate optionally substituted methylene (=CH2), and wherein two non-geminal or geminal substitutents selected from $R^a$, $R^b$, and any of the substituents $R^{1*}$, $R^2$, $R^{2*}$, $R^3$, $R^{3*}$, $R^{4*}$, $R^5$, $R^{5*}$, $R^6$ and $R^{6*}$, $R^7$, and $R^{7*}$ which are present and not involved in P, P*, or the covalent bridging moiety or moieties together may form an associated bridging moiety selected from substituents of the same kind as defined before;

the pair(s) of non-geminal substituents thereby forming a mono- or bicyclic entity together with (i) the atoms to which the non-geminal substituents are bound and (ii) any intervening atoms; and each of the substituents $R^{1*}$, $R^2$, $R^{2*}$, $R^3$, $R^{4*}$, $R^5$, $R^{5*}$, $R^6$ and $R^{6*}$, $R^7$, and $R^{7*}$ which are present and not involved in P, P*, or the covalent bridging moiety or moieties is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkylaminocarbonyl, mono- and di($C_{1-6}$-alkyl)amino-$C_{1-6}$-alkylaminocarbonyl, $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, and halogens, where aryl and heteroaryl may be optionally substituted, and where two geminal substituents together may designate oxo, thioxo, imino, or optionally substituted methylene, or together may form a spiro bridging moiety consisting of a 1-5 carbon atom(s) alkylene chain which is optionally interrupted and/or terminated by one or more substituents selected from —O—, —S—, and —($N^{RN}$)— where $R^N$ is selected from hydrogen and $C_{1-4}$-alkyl, and where two adjacent (non-geminal) substituents may designate an additional bond resulting in a double bond;
and $R^{N*}$, when present and not involved in a covalent bridging moiety, is selected from hydrogen and $C_{1-4}$-alkyl; and basic salts and acid addition salts thereof.

As is evident from the general formula above, and the definitions associated therewith, there may be one or several asymmetric carbon atoms present in the oligomers, depending on the nature of the substituents and possible covalent bridging moieties. The oligomers used in the present invention are intended to include all stereoisomers arising from the presence of any and all isomers of the individual monomer fragments as well as mixtures thereof, including racemic mixtures. Also included within the scope of the invention are variants of the general formula where B is in the α-configuration.

When considering the definitions and the known nucleosides (naturally occurring and non-naturally occurring) and nucleoside analogues (including known bi- and tricyclic analogues), it is clear that an oligomer may comprise one or more LNA(s) (which may be identical or different from one another, both with respect to selection of substituent and with respect to selection of covalent bridging moiety) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above. Preferably the oligonucleotide contains at least one LNA analog at the 3' hydroxy terminus of the oligonucleotide.

As described above, the monomeric nucleosides and nucleoside analogues of an oligomer are connected with other monomers via an internucleoside linkage. In the present context, the term "internucleoside linkage" means a linkage consisting of 2 to 4, preferably 3, substituents selected from —$CH_2$—, —O—, —S—, —$NR^H$—, >C=0, >C=$NR^H$, >C=S, —Si(R")$_2$—, —SO—, —S(O)$_2$—, —P(O)$_2$— —PO(BH$_3$)—, —P(O,S)—, —P(S)$_2$—, —PO(R")—, —PO(OCH3)—, and —PO(NHR$^H$)—, where $R^H$ is selected from hydrogen and $C_{1-4}$alkyl, and R" is selected from $C_{1-6}$-alkyl and phenyl. In some cases, the internucleoside linkage may be chiral. The oligomers used in the present invention are intended to include all stereoisomers arising from the presence of any and all isomers of the individual internucleoside linkages as well as mixtures thereof, including racemic mixtures.

In one series of useful embodiments, as disclosed in WO 99/14226 and U.S. Pat. No. 6,268,490, LNAs contain a methylene bridge connecting the 2'-oxygen of the ribose with the 4'-carbon according to the following formula:

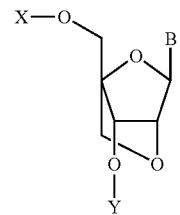

where B is a nucleobase, and X and Y are internucleoside linkages. Without intending to be bound by theory, the covalent bridging moiety of these analogues is believed to reduce the conformational flexibility of the ribose ring by locking it in a 3'-endo conformation and to thereby increase the local organization of the phosphate backbone.

In other useful embodiments of this structure, the 2'-oxygen position is substituted with nitrogen or sulfur as shown in the following structures:

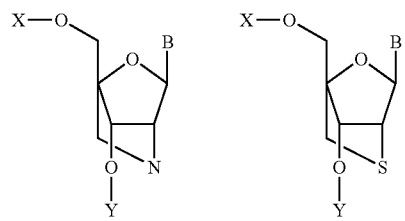

where B is a nucleobase, and X and Y are internucleoside linkages.

In other useful embodiments of the basic LNA structure, as disclosed in WO 99/14226, the covalent bridging moiety may include more than one carbon atom and may span other positions within the ribose ring according to the following structures:

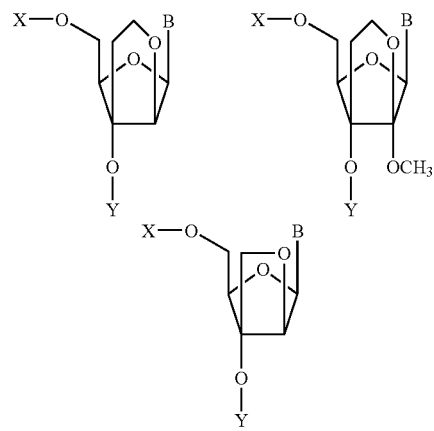

where B is a nucleobase, and X and Y are internucleoside linkages.

Alternatively, oligonucleotides used for sequence alteration in the methods, compositions, and kits of the present invention may include oligomers comprising at least one nucleoside having a xylo-LNA structure as disclosed in WO 00/56748 and having the general formula:

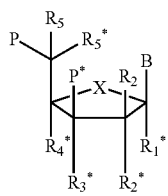

where the internucleoside linkages are designated by P and P*, and the other groups may be the substituents disclosed in WO 00/56748. Specific examples of this analogue are disclosed in WO 00/50748 with the following structural framework:

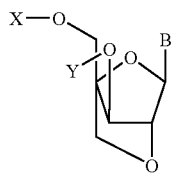

where B is a nucleobase, and X and Y are internucleoside linkages. Also disclosed in WO 00/56748 and considered within the scope of the current invention are nucleoside analogues that contain linkages between the 2' and 5' carbons of the ribose ring:

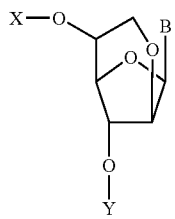

where B is a nucleobase, and X and Y are internucleoside linkages.

Other embodiments of the invention may include oligomers comprising at least one nucleoside having an L-Ribo-LNA structure as disclosed in WO 00/66604 and having the general formula:

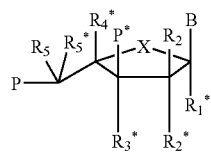

where the internucleoside linkages are designated by P and P*, and the other groups may be the substituents disclosed in WO 00/66604. Specific examples of this analogue are disclosed in WO 00/66604 with the following structural framework:

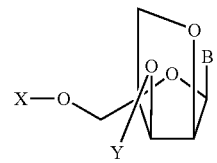

where B is a nucleobase, and X and Y are internucleoside linkages.

Other embodiments considered within the scope of the present invention include oligonucleotides that contain the nucleoside analogues disclosed in U.S. Pat. No. 6,043,060. These analogues are represented by monomer units of the general formula:

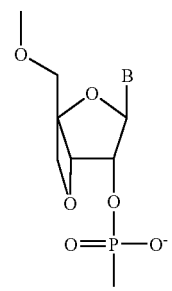

where B is a pyrimidine or purine nucleic acid base, or a derivative thereof, and where, within an oligomer, the plurality of B substituents may be identical to or different from one antoher.

Synthesis of the nucleosides and nucleoside analogues useful in the practice of the present invention, and the oligomers that contain them, can be performed as disclosed in WO 99/14226, WO 00/56748, WO 00/66604, WO 98/39352, US Pat. No. 6,043,060, and U.S. Pat. No. 6,268,490. Certain of the analogues, and synthesis services, are available commercially (Proligo, Boulder, Colo., USA).

In a first aspect, the invention provides an improved method for oligonucleotide-mediated nucleic acid sequence alteration, in which the sequence alteration is effected by combining the targeted nucleic acid in the presence of cellular repair proteins with a sequence-altering targeting oligonucleotide. The improvement comprises either adding lambda beta protein additionally to the combination or first contacting the cells having the cellular repair proteins with an HDAC inhibitor or hydroxyurea. The method thus comprises combining the targeted nucleic acid, in the presence of cellular repair proteins, with a sequence-altering targeting oligonucleotide, and either adding lambda beta protein additionally to the combination or first contacting the cells having the cellular proteins with an HDAC inhibitor or hydroxyurea.

The sequence-altering oligonucleotide and target may be combined ex vivo, with the cellular repair proteins present within selectively enriched cells, cells in culture, or cell-free extracts. Alternatively, the sequence-altering oligonucleotide and target may instead be combined in vivo, in which the cellular repair proteins are present within cells present within the body.

The methods, compositions, and kits of the invention can be used to enhance the alteration mediated by an oligonucleotide directing any kind of alteration, including, for example, deletion, insertion or replacement of 1, 2 or 3 nucleotides in the target sequence. These altered nucleotides may be contiguous or non-contiguous to each other. Further, nucleic acid sequence alteration by oligonucleotides targeting 1, 2, or 3 multiple sequence alterations is also enhanced using the kits and methods of the instant invention. Each of such multiple mutations can include, for example, deletion, insertion or replacement of 1, 2 or 3 nucleotides in the target sequence. These altered nucleotides may be contiguous or non-contiguous to each other. Where nucleic acid sequence alteration of multiple sequence targets is enhanced, the multiple alterations can be directed by a single oligonucleotide or by 1, 2 or 3 separate oligonucleotides. Usefully, the multiple alterations are directed by a single oligonucleotide, and the multiple alterations are within 1 to 10 nucleotides of each other.

The methods, compositions, and kits of the instant invention can be used to enhance the efficiency of nucleic acid sequence alteration directed by an oligonucleotide that targets either strand of a double-stranded target nucleic acid. In a particularly useful embodiment, these methods are used to enhance the efficiency of an oligonucleotide targeting actively transcribed sequences. In another useful embodiment, these methods are used to enhance the efficiency of an oligonucleotide targeting the non-transcribed strand of the target sequence.

The methods, compositions, and kits of the invention can be used to enhance the efficiency of nucleic acid sequence alteration directed by an oligonucleotide that targets genomic DNA, including nuclear and organelle chromosomal DNA, and artificial chromosomal DNA, such as yeast artificial chromosomes (YACs), bacterial artificial chromosomes (BACs), plant artificial chromosomes (PIACs), binary-bacterial artificial chromosomes (BiBACS), and human artificial chromosomes (HACs). The methods, compositions, and kits of the instant invention can be used to enhance the efficiency of oligo-directed sequence alteration of other types of targets, such as isolated episomal targets, including, for example, plasmids, cosmids, phagemids, and nonintegrated viruses.

The methods, compositions, and kits of the invention can be used to enhance the efficiency of oligonucleotide-directed targeted sequence alteration targeted to any part of a gene including, for example, an exon, an intron, a promoter, an enhancer or a 3'- or 5'-untranslated region. Further, the methods, compositions, and kits of the invention can be used to enhance the efficiency of an oligonucleotide mediated targeted sequence alteration of intragenic or intergenic sequences.

The methods, compositions, and kits of the present invention can be used to increase the efficiency of oligonucleotide-mediated nucleic acid sequence alteration in a wide variety of cell types, or within protein extracts derived from such cell types, drawn from a wide variety of species, including both prokaryotic and eukaryotic species.

Thus, the methods, compositions, and kits of the instant invention can be used to enhance the efficiency of nucleic acid sequence alteration in cells drawn from lower eukaryotes, such as fungal cells, including yeast cells, or within extracts from such cells, including *Saccharomyces cerevisiae, Schizosaccharomyces pombe*, Pichia species, such as methanolica, *Ustilago maydis*, and Candida species, including *Candida albicans*; within insect cells or extracts thereof, such as cells (or extracts) from *Drosophila melanogaster* and Anopheles species; and roundworms, such as *Caenorhabditis elegans*.

The methods, compositions, and kits of the instant invention can be used to enhance the efficiency of nucleic acid sequence alteration in cells (or extracts thereof) drawn from higher eukaryotes, including plants, such as cells (or extracts thereof) drawn from experimental model plants such as *Chlamydomonas reinhardtii, Physcomitrella patens*, and *Arabidopsis thaliana* in addition to crop plants such as cauliflower (*Brassica oleracea*), artichoke (*Cynara scolymus*), fruits such as apples (Malus, e.g. domesticus), mangoes (Mangifera, e.g. indica), banana (Musa, e.g. acuminata), berries (such as currant, Ribes, e.g. rubrum), kiwifruit (Actinidia, e.g. chinensis), grapes (Vitis, e.g. vinifera), bell peppers (Capsicum, e.g. annuum), cherries (such as the sweet cherry, Prunus, e.g. avium), cucumber (Cucumis, e.g. sativus), melons (Cucumis, e.g. melo), nuts (such as walnut, Juglans, e.g. regia; peanut, Arachis hypogeae), orange (Citrus, e.g. maxima), peach (Prunus, e.g. persica), pear (Pyra, e.g. communis), plum (Prunus, e.g. domestica), strawberry (Fragaria, e.g. moschata or vesca), tomato (Lycopersicon, e.g. esculentum); leaves and forage, such as alfalfa (Medicago, e.g. sativa or truncatula), cabbage (e.g. Brassica oleracea), endive (Cichoreum, e.g. endivia), leek (Allium, e.g. porrum), lettuce (Lactuca, e.g. sativa), spinach (Spinacia, e.g. oleraceae), tobacco (Nicotiana, e.g. tabacum); roots, such as arrowroot (Maranta, e.g. arundinacea), beet (Beta, e.g. vulgaris), carrot (Daucus, e.g. carota), cassava (Manihot, e.g. esculenta), turnip (Brassica, e.g. rapa), radish (Raphanus, e.g. sativus), yam (Dioscorea, e.g. esculenta), sweet potato (Ipomoea batatas); seeds, including oilseeds, such as beans (Phaseolus, e.g. vulgaris), pea (Pisum, e.g. sativum), soybean (Glycine, e.g. max), cowpea (Vigna unguiculata), mothbean (Vigna aconitifolia), wheat (Triticum, e.g. aestivum), sorghum (Sorghum e.g. bicolor), barley (Hordeum, e.g. vulgare), corn (Zea, e.g. mays), rice (Oryza, e.g. sativa), rapeseed (*Brassica napus*), millet (Panicum sp.), sunflower (Helianthus annuus), oats (Avena sativa), chickpea (Cicer, e.g. arietinum); tubers, such as kohlrabi (Brassica, e.g. oleraceae), potato (Solanum, e.g. tuberosum) and the like; fiber and wood plants, such as flax (Linum e.g. usitatissimum), cotton (Gossypium e.g. hirsutum), pine (Pinus sp.), oak (Quercus sp.), eucalyptus (Eucalyptus sp.), and the like and ornamental plants such as turfgrass (Lolium, e.g. rigidum), petunia (Petunia, e.g. x hybrida), hyacinth (Hyacinthus orientalis), carnation (Dianthus e.g. caryophyllus), delphinium (Delphinium, e.g. ajacis), Job's tears (Coix lacryma-jobi), snapdragon (Antirrhinum majus), poppy (Papaver, e.g. nudicaule), lilac (Syringa, e.g. vulgaris), hydrangea (Hydrangea e.g. macrophylla), roses (including Gallicas, Albas, Damasks, Damask Perpetuals, Centifolias, Chinas, Teas and Hybrid Teas) and ornamental goldenrods (e.g. Solidago spp.). Generally, isolated plant cells are treated with a composition of the invention and/or according to a method of the invention and then used to regenerate whole plants according to any method known in the art.

The methods, compositions, and kits of the instant invention can be used to enhance the efficiency of nucleic acid sequence alteration in cells (or extracts thereof) drawn from animals, including, for example, domestic and wild fowl, such as chickens, geese, ducks, turkeys, pheasant, ostrich and pigeon; mammals, including domestic livestock, such as horses, cattle, sheep, pigs, goats, bison; fish such as salmon, tilapia, catfish, trout and bass; mammals, including model experimental animals such as mice, rats, guinea pigs, and rabbits; domestic pets such as dogs and cats; and human beings.

The methods, compositions, and kits of the instant invention can be used to enhance the efficiency of nucleic acid sequence alteration in cells (or extracts thereof) drawn from a wide variety of tissues and cell types, including somatic cells such as cells of liver, lung, colon, cervix, kidney, and epithelia, germ cells, pluripotent stem or committed progenitor cells, such as $CD34^+$ hematopoietic stem cells (including $CD34^+CD38^-$ cells), and embryonic stem cells (ES cells).

Currently, some jurisdictions have prohibitions on the culture and/or genetic manipulation of human stem cells. Thus, although the methods, compositions, and kits of the present invention can be used to enhance the efficiency of nucleic acid sequence alteration within human ES cells (or extracts thereof), the invention may, in some instances, be practiced in all cell types except human embryonic stem cells. No such prohibitions exist at present for culture and/or genetic manipulation of murine embryonic stem cells or stem cells from other animals, and the present invention may thus be used without restriction to increase the efficiency of sequence alteration in embryonic stem cells from species other than human beings, including mice, rats, cows, sheep, goats, monkeys, apes, and cattle.

Each of the methods, compositions, and kits of the present invention can be combined with one or more of the other methods, compositions, and kits of the present invention, further to increase efficiency of sequence alteration.

Additionally, the methods, compositions, and kits of the present invention can be used in conjunction with other methods for increasing the efficiency of oligo-mediated nucleic acid sequence alteration.

For example, the methods, compositions, and kits of the present invention can be used to introduce sequence alterations into cells that have altered nucleic acid sequence alteration efficiency based upon increased or decreased levels or activity of at least one protein from the RAD52 epistasis group, the mismatch repair group or the nucleotide excision repair group. Members of these groups include: RAD50, RAD51, RAD52, RAD54, RAD55, RAD57, RAD59, MRE 1 and XRS1 in the RAD52 epistasis group; MSH2, MSH3, MSH6 and PMS1 in the mismatch repair group; and RAD1, RAD2, RAD10, RAD23 and EXO1 in the nucleotide excision repair group. The designation "RAD52 epistasis group" is taken from the yeast (Saccharomyces cerevisiae) designation, but it is understood that homologs, orthologs and paralogs from other organisms, including bacteria, plants, animals and other fungi can be used in the methods of the instant invention.

In particular, the methods, compositions, and kits of the present invention can be used to introduce sequence alterations into cells that have reduced levels or activity of at least one protein selected from the group consisting of a homolog, ortholog or paralog of RAD1, RAD51, RAD52, RAD57 and PMS1. See, for example, International Patent Application PCT/US01/23770, published as WO 02/10364, and commonly owned, copending, U.S. patent application no. 10/351,662, filed Jan. 24, 2003, the disclosures of which are incorporated herein by reference in their entireties.

Alternatively, or in addition, the methods, compositions, and kits of the present invention can be used to introduce sequence alterations into cells (or extracts thereof) that have altered nucleic acid sequence alteration efficiency based upon increased levels of at least one of the normal allelic RAD10, RAD51, RAD52, RAD54, RAD55, MRE11, PMS1or XRS2 proteins, or with increased activity of one of these proteins. See commonly owned and copending U.S. patent application serial number 10/260,375, filed Sep. 27, 2002, the disclosure of which is incorporated herein by reference in its entirety.

The methods, compositions, and kits of the present invention may also be used with methods that enhance oligonucleotide-directed nucleic acid sequence alteration by reducing the number of target nucleic acid molecules required to be screened during oligonucleotide-directed targeted nucleic acid sequence alteration.

As further described and illustrated in Examples herein below, such methods involve using at least a first and a second oligonucleotide, each of which is capable of directing alteration in at least a first and a second nucleic acid target, respectively. At least the second oligonucleotide directs an alteration that produces a selectable phenotype, which is thereafter selected. Although the first oligonucleotide may direct an alteration that produces a selectable phenotype, generally the first oligonucleotide directs an alteration that must be identified by screening, e.g., determining the corresponding nucleic acid sequence or assaying a non-selectable phenotype that is generated by the alteration event.

The dual targeting approach reduces the number of nucleic acid molecules required to be screened by at least about two-fold relative to the number that must be screened in a composition that has not previously been selected for an oligonucleotide-directed nucleic acid sequence alteration that confers a selectable phenotype. The reduction can be by at least about two, three, four, five, six, seven, eight, nine, ten, twelve, fifteen, twenty, thirty, and fifty or more fold.

Sequence alteration by the second oligonucleotide may confer any selectable phenotype known in the art, choice of which will depend, in part, upon the host cell chosen and whether the selection is to be effected in vitro or in vivo. Exemplary selectable phenotypes include, e.g., antibiotic or other chemical resistance, ability to use a nutrient source, expression of a fluorescent protein, presence of an epitope or resistance to an apoptotic signal.

In yet a further alternative, the methods, compositions and kits of the present invention may be used in dual targeting methods, as above-described, further comprising administration of at least one purified protein in the RAD52 epistasis group, the mismatch repair group, or the nucleotide excision repair group. In certain embodiments, the method comprises administering the two oligonucleotides to a cell in which two distinct proteins are manipulated—for example, by knockout of one chromosomal gene and complementation or supplementation of a second gene product to produce increased or altered levels of the second protein. In one such embodiment, the targeted cell has a knock-out mutation in the chromosomal RAD52 gene and the cell is complemented or supplemented with the RAD51 gene product expressed in trans under control of a promoter, e.g. a constitutive promoter.

In yet a further embodiment, the methods, compositions, and kits of the present invention are used in conjunction with a cell (or extract thereof) in a particular phase of the growth cycle, developmental state or cell cycle position that exhibits altered nucleic acid sequence alteration efficiency. A particular phase of growth that particularly favors nucleic acid sequence alteration may be easily determined by sampling cells at multiple points during the growth cycle, for example over the course of a growth curve, and monitoring sequence alteration in those cells using the assays described herein. Phases of the growth cycle that might particularly favor nucleic acid sequence alteration include, for example, lag phase, early log phase, log phase, late log phase, the transition between log and stationary phase, early stationary phase and late stationary phase. Alternatively, these may be the S phase, M phase, G1 phase or G2 phase of the cell cycle or transition points between the phases. Particular developmental phases can be similarly assayed with cells that have been induced to differentiate by, for example, hormone or other treatments, or differentiated cells isolated from a particular tissue.

The oligonucleotides, including oligonucleotide-containing compositions, used in the methods of the present invention can be introduced into cells or tissues by any technique known to one of skill in the art. Such techniques include, for example, electroporation, liposome transfer, naked nucleic acid insertion, particle bombardment and calcium phosphate precipitation. In one embodiment the transfection is performed with a liposomal transfer compound, for example, DOTAP (N-1-(2,3-Dioleoyloxy)propyl-N,N, N-trimethylammonium methylsulfate, Boehringer-Mannheim) or an equivalent, such as LIPOFECTIN®). In another embodiment, the transfection technique uses cationic lipids. In a preferred embodiment, transfection is performed with Lipofectamine™ 2000 (Invitrogen). The methods of the invention can be used with a wide range of concentration of oligonucleotides. For example, good results can be achieved with 10 nM/$10^5$ cells. A ratio of about 500 ng of oligonucleotide in 3 μg of DOTAP per $10^5$ cells can be used. The transfected cells may be cultured in different media, including, for example, in serum-free media, media supplemented with human serum albumin, or human serum.

The methods, compositions, and kits of the instant invention comprising either an HDAC inhibitor, such as trichostatin A, or HU typically increase nucleic acid sequence alteration efficiency by at least two fold relative to the same method respectively lacking the HDAC inhibitor or HU. The increase in nucleic acid sequence alteration efficiency can also be about three, four, five, six, seven, eight, nine, ten, twelve, fifteen, twenty, thirty, and fifty or more fold. The methods, compositions, and kits of the instant invention comprising beta protein increase the efficiency of altering a DNA sequence, as compared to the same method lacking beta protein, typically at least 2 fold, and can increase the efficiency 5 fold, 10 fold, 15 fold, 20 fold, 25 fold, 30 fold, 40 fold, 50 fold, 60 fold, 70 fold, 80 fold, 90 fold, 100 fold, 250 fold, 500 fold, 1000 fold, or more; in certain embodiments, the methods, compositions, and kits of the instant invention that comprise beta protein increase efficiency less than two-fold as compared to comparable methods lacking beta protein, such as 1.9 fold, 1.5 fold, or even by 10%, 20%, 30%, 40%.

In embodiments of the methods of the present invention that utilize an HDAC inhibitor or HU, cells may be first contacted with the HDAC inhibitor or hydroxyurea, then the oligonucleotide combined with the target in the presence of cellular repair proteins. Alternatively, the HDAC inhibitor or hydroxyurea may be contacted to the cells concurrently with combining of the oligonucleotide with the target. In yet other alternatives, the HDAC inhibitor or hydroxyurea may be contacted to the cells after the oligonucleotide is combined with the target.

The HDAC inhibitor can be trichostatin A. One of skill in the art will appreciate, however, that other HDAC inhibitors may be suitable for these purposes. For example, U.S. Patent Application No. 2002/0143052, which is hereby incorporated by reference in its entirety, discloses compounds having HDAC inhibitor activity due to the presence of a zinc-binding moiety. Other examples of HDAC inhibitors suitable for purposes of the invention include butyric acid, MS-27-275, suberoylanilide hydroxamic acid (SAHA), oxamflatin, trapoxin A, depudecin, FR901228 (also known as depsipeptide), apicidin, m-carboxy-cinnamic acid bishydroxamic acid (CBHA), suberic bishydroxamic acid (SBHA), and pyroxamide. See Marks et al., J. Natl. Canc. Inst. 92(15), 1210-1216 (2000), which is hereby incorporated by reference in its entirety. Yet other examples of suitable HDAC inhibitors are chlamydocin, HC-toxin, Cyl-2, WF-3161, and radicicol, as disclosed in WO 00/23567, which is hereby incorporated by reference in its entirety.

When administering an HDAC inhibitor or HU to cells or cell extracts, the dosage to be administered and the timing of administration will depend on various factors, including cell type.

In the case of TSA, the dosage may be 10 nM, 100 nM, 1 μM, 10 μM, 100 μM, 1 mM, 10 mM, or even higher, or as little as 1 mM, 100 μM, 10 μM, 1 μM, 100 nM, 10 nM, 1 nM, or even lower. In the case of HU, the dosage may be 100 nM, 1 μM, 10 μM, 100 μM, 1 mM, 10 mM, 100 mM, 1 M or even higher, or as little as 100 mM, 10 mM, 1 mM, 100 μM, 10 μM, 1 pM, 100 nM, 10 nM, or even lower.

In the case of HU, the dosage is preferably from about 0.05 mM to 3 mM for mammalian cells. The dosage may be at least 0.05 mM, 0.10 mM, 0.15 mM, 0.20 mM, 0.25 mM, 0.30 mM, 0.35 mM, 0.40 mM, 0.50 mM or more, including at least 0.55 mM, 0.60 mM, 0.65 mM, 0.70 mM, 0.75 mM, 0.80 mM, 0.85 mM, 0.90 mM, 0.95 mM or even 1 mM, 1.1 mM, 1.2 mM, 1.3 mM, 1.4 mM, 1.4 mM, 1.5 mM, 1.6 mM, 1.7 mM, 1.8 mM, 1.9 mM, 2.0 mM, 2.5 mM, 3 mM, or more. Typically, the dosage is less than about 3.0 mM, and can be less than 2.5 mM, 2.0 mM, 1.5 mM, 1.0 mM, even less than 0.90, 0.85, 0.80, 0.75, 0.70, 0.65, 0.60, 0.55, 0.50, 0.45, 0.40, and even less than about 0.35 or 0.30 mM.

Cells may be grown in the presence of an HDAC inhibitor or HU, and cell extracts may be treated with the HDAC inhibitor or HU, for various times prior to combination with a sequence-altering oligonucleotide. Growth or treatment may be as long as 1 h, 2 h, 3 h, 4 h, 6 h, 8 h, 12 h, 20 h, or even longer, including up to 28 days, 14 days, 7 days, or shorter, or as short as 12 h, 8 h, 6 h, 4 h, 3 h, 2 h, 1 h, or even shorter. Alternatively, treatment of cells or cell extracts with HDAC inhibitor or HU and the sequence-altering oligonucleotide may occur simultaneously, or HDAC inhibitor or HU, respectively, may be added after oligonucleotide addition.

Cells may further be allowed to recover from treatment with an HDAC inhibitor or HU by growth in the absence of the HDAC inhibitor or HU for various times prior to treatment with a sequence-altering oligonucleotide. Recovery may be as long as 10 min, 20 min, 40 min, 60 min, 90 min, 2 h, 4 h, or even longer, or as short as 90 min, 60 min, 40 min, 20 min, 10 min, or even shorter. Cells may also be allowed to recover following their treatment with a sequence-altering oligonucleotide. This recovery period may be as long as 1 h, 2 h, 4 h, 6 h, 8 h, 12 h, oreven longer, oras short as 8 h, 6 h,4 h, 2 h, 1 h, oreven shorter. The HDAC inhibitor or HU may either be present in or absent from the cell medium during the recovery period.

Optimum dosages and the timing and duration of administration of HDAC inhibitors and HU to cells or cell extracts can be determined by routine experimentation.

For example, optimized dosage and timing of treatment with an HDAC inhibitor, such as TSA, can be determined using the assay system set forth in Example 6 herein below. Cultured cells (such as yeast cells) are treated with varying concentrations of HDAC inhibitor for a varying number of hours prior to electroporation with the sequence altering oligonucleotide. After recovery for varying periods, the cells are plated and tested for efficiency of sequence alteration. Parameters are then selected that provide the highest efficiency of correction. The method may then be repeated, as necessary, further to optimize dosage, duration of pretreatment, duration of recovery period, if any, and the like.

A similar approach for HU can be determined using the assay system set forth in Example 8 below.

Such assays, or apparent variants thereof, may be performed to optimize conditions for any chosen cell type.

In embodiments of the first aspect of the present invention that use beta protein, lambda beta protein is added to the combination of sequence-altering oligonucleotide and target nucleic acid. As used herein, the term "beta protein" refers to a protein expressed from the bet gene of the Red recombination system from any strain of bacteriophage lambda. The term additionally encompasses an altered version of beta protein derived from the native, full length gene product that is nonetheless capable of increasing the efficiency of altering a DNA sequence by homologous recombination, gene repair mechanisms or oligonucleotide-mediated nucleic acid sequence alteration. Such altered versions of beta protein include but are not limited to fusions of beta protein with other proteins or peptides, or other macromolecules; fragments of beta protein; and beta protein containing changes in its primary amino acid sequence. As will be appreciated by the skilled artisan, because of the degeneracy of the genetic code, many different gene sequences can encode beta protein. Thus, according to the knowledge of the skilled artisan, one or more synthetic genes can be created that encode for beta protein but which contain codons preferred by the cell in which the gene is to be expressed, which codons are different from those found in the native beta gene.

According to an embodiment of the methods of the present invention, beta protein is introduced into cells containing a target DNA sequence, the sequence of which is desired to be altered, so as to increase the efficiency of targeted gene repair by targeted nucleic acid sequence altering oligonucleotides also present in cells. Although not wishing to be bound by theory, it is believed that beta protein increases the efficiency of altering the targeted DNA sequence in such cells by participating in a targeted gene repair mechanism, and not by a homologous recombination mechanism. The DNA sequence desirably altered using the methods of the present invention can be contained within a natural chromosome of a cell, or reside in an extrachromosomal element, including but not limited to a DNA fragment, a plasmid, a phagemid, a viral genome, a prokaryotic genome, a bacterial artificial chromosome, a yeast artificial chromosome, or a human artificial chromosome.

Beta protein can increase the efficiency of oligonucleotide-directed targeted sequence alteration of DNA as much as 2 fold, 5 fold, 10 fold, 15 fold, 20 fold, 25 fold, 30 fold, 40 fold, 50 fold, 60 fold, 70 fold, 80 fold, 90 fold, 100 fold, 250 fold, 500 fold, 1000 fold, or more, as compared to the same method lacking beta protein, or as little as 500 fold, 250 fold, 100 fold, 90 fold, 80 fold, 70 fold, 60 fold, 50 fold, 40 fold, 30 fold, 25 fold, 20 fold, 15 fold, 10 fold, 5 fold, 2 fold, 1.5 fold, or less.

Beta protein can be used to increase the efficiency of altering a DNA sequence using targeted nucleic acid sequence altering oligonucleotides in a variety of cell types, including, but not limited to prokaryotic cells, including bacterial cells; as well as eukaryotic cells, including yeast and other fungal cells; plant cells, including dicotyledonous and monocotyledonous plant cells; and animal cells, including invertebrate cells, including insect cells; and vertebrate cells, including mammalian cells, including human and non-human mammals.

A variety of methods known to the skilled artisan are available for introducing beta protein into cells such that the protein can effect an increase in efficiency of altering a DNA sequence by gene repair mechanisms. Beta protein can be introduced into cells directly as protein, or indirectly by introducing into cells a beta protein expression construct that encodes for beta protein when acted upon by the cell's transcriptional and translational machinery. Such a construct can be in the form of pretranscribed mRNA, or in the form of a DNA expression vector capable of being transcribed.

Protein specific techniques for introducing beta protein into cells include but are not limited to the ChariotTM protein transfection reagent available from Active Motif, Inc. (Carlsbad, Calif.); chemical coupling between beta protein and penetratin 1, a fragment of the Drosophila Antennapedia protein; protein fusion between beta protein and HIV-1 TAT protein or the herpes simplex virus-1 protein VP22.

Other methods are applicable both for introducing beta protein and nucleic acids encoding beta protein into cells. Such methods include but are not limited to microinjection; electroporation; transfection using chemical reagents, such as charged lipophilic molecules, e.g., lipofectin, lipofectamine; biolistic transfection; calcium phosphate coprecipitation; and fusion of liposomes, including cationic liposomes, with the cell membrane of cells Yet other methods are principally suited for introducing a nucleic acid encoding beta protein into cells, including use of viral vectors capable of infecting cells.

Typically, if a vector is to be used for expression of beta protein, coding sequence for beta protein is cloned, using techniques well known in the art, into an appropriate vector chosen by the skilled artisan. Cells containing a beta protein vector are known as a host cells. Host cells can either be used to produce beta protein for subsequent purification using techniques well known in the art, or alternatively, a host cell can be the cell in which beta protein is expressed for the purpose of increasing the efficiency of oligonucleotide mediated sequence alteration.

Although not wishing to be bound by theory, it is believed that varying the amount of beta protein introduced, directly or indirectly, into a cell will affect the extent to which the efficiency of DNA sequence alteration can be modulated. If beta protein is introduced directly into cells, the dose can be controlled by varying the amount of beta protein. The amount of beta protein produced from a vector contained in a host cell can also be varied according to methods known to the skilled artisan. Such methods include varying the number of beta protein coding sequences present on each vector molecule; varying the average number of vector molecules contained in each cell; varying the strength of transcriptional and translational control elements present on the vector; varying the stability of mRNA produced from vectors; varying the strength or extent of the environmental variable that is capable of inducing beta protein expression via one or more inducible transcriptional control elements. Other methods for controlling the amount of beta protein introduced directly or indirectly into a cell are within the knowledge of the skilled artisan.

The average amount of beta protein introduced per cell can vary from $1\times10^{-19}$ grams, $1\times10^{-18}$ grams, $1\times10^{-17}$ grams, $1\times10^{-16}$ grams, $1\times10^{-15}$ grams, $1\times10^{-14}$ grams, $1\times10^{-13}$ grams, $1\times10^{-12}$ grams, $1\times10^{-11}$ grams, $1\times10^{-10}$ grams, $1\times10^{-9}$ grams, $1\times10^{-8}$ grams, to $1\times10^{-7}$ grams or more. The average amount of beta protein introduced per cell can vary from $1\times10^{-6}$ grams, $1\times10^{-7}$ grams, $1\times10^{-8}$ grams, $1\times10^{-9}$ grams, $1\times10^{-10}$ grams, $1\times10^{-11}$ grams, $1\times10^{-12}$ grams, $1\times10^{-13}$ grams, $1\times10^{-14}$ grams, $1\times10^{-15}$ grams, $1\times10^{-16}$ grams, $1\times10^{-17}$ grams, to $1\times10^{-18}$ grams or less.

The vectors can be used, interalia, for propagating the beta protein coding sequence in host cells (cloning vectors), for shuttling the beta protein coding sequence between host cells derived from disparate organisms (shuttle vectors), for inserting the beta protein coding sequence into host cell chromosomes (insertion vectors), for expressing the beta protein, alone or as fusions to heterologous polypeptides, in vitro or within a host cell. Vectors of the present invention will often be suitable for several such uses.

Vectors are by now well known in the art, and are described, interalia, in Jones et al. (eds.), Vectors: Cloning Applications : Essential Techniques (Essential Techniques Series), John Wiley & Son Ltd 1998 (ISBN: 047196266X); Jones et al. (eds.), Vectors: Expression Systems : Essential Techniques (Essential Techniques Series), John Wiley & Son Ltd, 1998 (ISBN:0471962678); Gacesa et al., Vectors: Essential Data, John Wiley & Sons, 1995 (ISBN: 0471948411); Cid-Arregui (eds.), Viral Vectors: Basic Science and Gene Therapy, Eaton Publishing Co., 2000 (ISBN: 188129935X); Sambrook et al., Molecular Cloning: A Laboratory Manual (3rd ed.), Cold Spring Harbor Laboratory Press, 2001 (ISBN: 0879695773); Ausubel et al. (eds.), Short Protocols in Molecular Biology: A Compendium of Methods from Current Protocols in Molecular Biology (4th ed.), John Wiley & Sons, 1999 (ISBN: 047132938X), the disclosures of which are incorporated herein by reference in their entireties. Furthermore, an enormous variety of vectors are available commercially. Use of existing vectors and modifications thereof being well within the skill in the art, only basic features need be described here.

Typically, vectors are derived from virus, plasmid, prokaryotic or eukaryotic chromosomal elements, or some combination thereof, and include at least one origin of replication, at least one site for insertion of heterologous nucleic acid, typically in the form of a polylinker with multiple, tightly clustered, single cutting restriction sites, and at least one selectable marker, although some integrative vectors will lack an origin that is functional in the host to be chromosomally modified, and some vectors will lack selectable markers. Vectors of the present invention will further include at least one beta protein coding sequence inserted into the vector in at least one location.

Where present, the origin of replication and selectable markers are chosen based upon the desired host cell or host cells; the host cells, in turn, are selected based upon the desired application.

In the case of prokaryotic cells, typically *E. coli*, vector replication is predicated on the replication strategies of coliform-infecting phage—such as phage lambda, Ml 3, T7, T3 and P1—or on the replication origin of autonomously replicating episomes, notably the ColE1 plasmid and later derivatives, including pBR322 and the pUC series plasmids. Where *E. coli* is used as host, selectable markers are, analogously, chosen for selectivity in Gram negative bacteria: e.g., typical markers confer resistance to antibiotics, such as ampicillin, tetracycline, chloramphenicol, kanamycin, streptomycin, zeocin; auxotrophic markers can also be used.

In the case of yeast cells, typically *S. cerevisiae*, vectors of the present invention for use in yeast will typically, but not invariably, contain an origin of replication suitable for use in yeast and a selectable marker that is functional in yeast.

Integrative Ylp vectors do not replicate autonomously, but integrate, typically in single copy, into the yeast genome at low frequencies and thus replicate as part of the host cell chromosome; these vectors lack an origin of replication that is functional in yeast, although they typically have at least one origin of replication suitable for propagation of the vector in bacterial cells. YEp vectors, in contrast, replicate episomally and autonomously due to presence of the yeast 2 micron plasmid origin (2 pm ori). The YCp yeast centromere plasmid vectors are autonomously replicating vectors containing centromere sequences, CEN, and autonomously replicating sequences, ARS; the ARS sequences are believed to correspond to the natural replication origins of yeast chromosomes. YACs are based on yeast linear plasmids, denoted YLp, containing homologous or heterologous DNA sequences that function as telomeres (TEL) in vivo, as well as containing yeast ARS (origins of replication) and CEN (centromeres) segments.

Selectable markers in yeast vectors include a variety of auxotrophic markers, the most common of which are (in Saccharomyces cerevisiae) URA3, HIS3, LEU2, TRP1 and LYS2, which complement specific auxotrophic mutations, such as ura3-52, his3-D1, leu2-D1, trpl-Dl and lys2-201. The URA3 and LYS2 yeast genes further permit negative selection based on specific inhibitors, 5-fluoro-orotic acid (FOA) and α-aminoadipic acid (αAA), respectively, that prevent growth of the prototrophic strains but allows growth of the ura3 and lys2 mutants, respectively. Other selectable markers confer resistance to, e.g., zeocin.

In the case of insect cells where the host cells are from *Spodoptera frugiperda*—e.g., Sf9 and Sf21 cell lines, and expresSF™ cells (Protein Sciences Corp., Meriden, Conn., USA)—the vector replicative strategy is typically based upon the baculovirus life cycle. Typically, baculovirus transfer vectors are used to replace the wild-type AcMNPV polyhedrin gene with a beta protein coding sequence. Sequences that flank the polyhedrin gene in the wild-type genome are positioned 5' and 3' of the expression cassette on the transfer vectors. Following cotransfection with AcMNPV DNA, a homologous recombination event occurs between these sequences resulting in a recombinant virus carrying the beta protein coding sequence and the polyhedrin or p10 promoter. Selection can be based upon visual screening for lacZ fusion activity.

In the case of mammalian cells, vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy.

Selectable markers for use in mammalian cells include resistance to neomycin (G418), blasticidin, hygromycin and to zeocin, and selection based upon the purine salvage pathway using HAT medium.

In the case of plant cells, the vector replicon is typically derived from a plant virus (e.g., cauliflower mosaic virus, CaMV; tobacco mosaic virus, TMV) and selectable markers chosen for suitability in plants.

The invention further provides artificial chromosomes—BACs, BiBACs, YACs, PACs, and HACs—for use as vectors that comprise beta protein coding sequence.

The BAC system is based on the well-characterized *E. coli* F-factor, a low copy plasmid that exists in a supercoiled circular form in host cells. The structural features of the F-factor allow stable maintenance of individual human DNA clones as well as easy manipulation of the cloned DNA. See Shizuya et al., Keio J. Med. 50(1):26-30 (2001); Shizuya et al., Proc. Natl. Acad. Sci. USA 89(18):8794-7 (1992).

YACs are based on yeast linear plasmids, denoted YLp, containing homologous or heterologous DNA sequences that function as telomeres (TEL) in vivo, as well as containing yeast ARS (origins of replication) and CEN (centromeres) segments.

HACs are human artificial chromosomes. Kuroiwa et al., Nature Biotechnol. 18(10):1086-90 (2000); Henning et al., Proc. Natl. Acad. Sci. USA 96(2):592-7 (1999); Harrington et al., Nature Genet. 15(4):345-55 (1997). In one version, long synthetic arrays of alpha satellite DNA are combined with telomeric DNA and genomic DNA to generate linear microchromosomes that are mitotically and cytogenetically stable in the absence of selection.

PACs are P1-derived artificial chromosomes. Sternberg, Proc. Natl. Acad. Sci. USA 87(1):103-7 (1990); Sternberg et al., New Biol. 2(2):151-62 (1990); Pierce et al., Proc. Natl Acad. Sci. USA 89(6):2056-60 (1992).

Vectors of the present invention will also often include elements that permit in.vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Expression vectors of the present invention—that is, those vectors that will drive expression of the beta protein coding sequence—will often include a variety of other genetic elements operatively linked to the coding sequence, typically genetic elements that drive transcription, such as promoters and enhancer elements, those that facilitate RNA processing, such as transcription termination and/or polyadenylation signals, and those that facilitate translation, such as ribosomal consensus sequences.

For example, vectors for expressing proteins of the present invention in prokaryotic cells, typically E. coli, will include a promoter, often a phage promoter, such as phage lambda pL promoter, the trc promoter, a hybrid derived from the trp and lac promoters, the bacteriophage T7 promoter (in E. coli cells engineered to express the T7 polymerase), or the araBAD operon. Often, such prokaryotic expression vectors will further include transcription terminators, such as the aspA terminator, and elements that facilitate translation, such as a consensus ribosome binding site and translation termination codon, Schomer et al., Proc. Natl. Acad. Sci. USA 83:8506-8510 (1986).

As another example, vectors for expressing proteins of the present invention in yeast cells, typically S. cerevisiae, will include a yeast promoter, such as the CYC1 promoter, the GAL1 promoter, ADH1 promoter, or the GPD promoter, and will typically have elements that facilitate transcription termination, such as the transcription termination signals from the CYC1 or ADH1 gene.

As another example, vectors for expressing beta protein coding sequence in mammalian cells will include a promoter active in mammalian cells. Such promoters are often drawn from mammalian viruses—such as the enhancer-promoter sequences from the immediate early gene of the human cytomegalovirus (CMV), the enhancer-promoter sequences from the Rous sarcoma virus long terminal repeat (RSV LTR), and the enhancer-promoter from SV40. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Vector-driven protein expression can be constitutive or inducible.

Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PLtetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet.repressor protein and induced in response to tetracycline (Tc) and Tc derivatives such as anhydrotetracycline.

As another example of inducible elements, hormone response elements, such as the glucocorticoid response element (GRE) and the estrogen response element (ERE), can confer hormone inducibility where vectors are used for expression in cells having the respective hormone receptors. To reduce background levels of expression, elements responsive to ecdysone, an insect hormone, can be used instead, with coexpression of the ecdysone receptor.

Expression vectors can be designed to fuse the expressed beta protein to small protein tags that facilitate purification and/or visualization.

For example, beta protein can be expressed with a polyhistidine tag that facilitates purification of the fusion protein by immobilized metal affinity chromatography, for example using NiNTA resin (Qiagen® Inc., Valencia, Calif., USA) or TALON® resin (cobalt immobilized affinity chromatography medium, Clontech Labs, Palo Alto, Calif., USA). As another example, the beta fusion protein can include a chitin-binding tag and self-excising intein, permitting chitin-based purification with self-removal of the fused tag (IMPACT™ system, New England Biolabs, Inc., Beverley, Mass., USA). Alternatively, the beta fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, beta protein can be expressed as a fusion to glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione.

Other tags include, for example, the Xpress™ epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed beta protein, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of beta proteins from a variety of mammalian cell lines.

For long-term, high-yield recombinant production of beta protein, beta protein fusions, and beta protein fragments of the present invention, stable expression is particularly useful.

Stable expression is readily achieved by integration into the host cell genome of vectors having selectable markers, followed by selection for integrants.

For example, the pUB6/V5-His A, B, and C vectors (Invitrogen, Carlsbad, Calif., USA) are designed for high-level stable expression of heterologous proteins in a wide range of mammalian tissue types and cell lines. pUB6/V5-His uses the promoter/enhancer sequence from the human ubiquitin C gene to drive expression of recombinant proteins: expression levels in 293, CHO, and NIH3T3 cells are comparable to levels from the CMV and human EF-1a promoters. The bsd gene permits rapid selection of stably transfected mammalian cells with the potent antibiotic blasticidin.

Replication incompetent retroviral vectors, typically derived from Moloney murine leukemia virus, prove particularly useful for creating stable transfectants having integrated provirus. The highly efficient transduction machinery of retroviruses, coupled with the availability of a variety of packaging cell lines—such as RetroPack™ PT 67, EcoPack2™-293, AmphoPack™-293, GP2-293 cell lines (all available from Clontech Laboratories, Palo Alto, Calif., USA)—allow a wide host range to be infected with high efficiency; varying the multiplicity of infection readily adjusts the copy number of the integrated provirus. Retroviral vectors are available with a variety of selectable markers, such as resistance to neomycin, hygromycin, and puromycin, permitting ready selection of stable integrants.

The present invention further includes host cells comprising the beta expression vectors of the present invention, either present episomally within the cell or integrated, in whole or in part, into the host cell chromosome.

Among other considerations, some of which are described above, a host cell strain may be chosen for its ability to process the expressed beta protein in the desired fashion. Such post-translational modifications of the polypeptide include, but are not limited to, acetylation, carboxylation, glycosylation, phosphorylation, lipidation, and acylation, and it is an aspect of the present invention to provide beta proteins with such post-translational modifications.

As noted earlier, host cells can be prokaryotic or eukaryotic. Representative examples of appropriate host cells include, but are not limited to, bacterial cells, such as *E. coli, Caulobacter crescentus*, Streptomyces species, and *Salmonella typhimurium*; yeast cells, such as *Saccharomyces cerevisiae, Schizosaccharomyces pombe, Pichia pastoris, Pichia methanolical*; insect cell lines, such as those from *Spodoptera frugiperda*—e.g., Sf9 and Sf21 cell lines, and expresSF™ cells (Protein Sciences Corp., Meriden, Conn., USA)—Drosophila S2 cells, and Trichoplusia ni High Five® Cells (Invitrogen, Carlsbad, Calif., USA); and mammalian cells. Typical mammalian cells include COS1 and COS7 cells, Chinese hamster ovary (CHO) cells, NIH 3T3 cells, 293 cells, HEPG2 cells, HeLa cells, L cells, murine ES cell lines (e.g., from strains 129/SV, C57/BL6, DBA-1, 129/SVJ), K562, Jurkat cells, and BW5147. Other mammalian cell lines are well known and readily available from the American Type Culture Collection (ATCC) (Manassas, Va., USA) and the National Institute of General medical Sciences (NIGMS) Human Genetic Cell Repository at the Coriell Cell Repositories (Camden, N.J., USA).

Methods for introducing the vectors and nucleic acids of the present invention into the host cells are well known in the art; the choice of technique will depend primarily upon the specific vector to be introduced and the host cell chosen.

For example, phage lambda vectors will typically be packaged using a packaging extract (e.g., Gigapack® packaging extract, Stratagene, La Jolla, Calif., USA), and the packaged virus used to infect *E. coli*. Plasmid vectors will typically be introduced into chemically competent or electrocompetent bacterial cells.

*E. coli* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, J. Mol. Biol. 166(4):557-80 (1983), and vectors introduced by heat shock. A wide variety of chemically competent strains are also available commercially (e.g., Epicurian Coli® XL10-Gold® Ultracompetent Cells (Stratagene, La Jolla, Calif., USA); DH5α competent cells (Clontech Laboratories, Palo Alto, Calif., USA); TOP10 Chemically Competent *E coli* Kit (Invitrogen, Carlsbad, Calif., USA)).

Bacterial cells can be rendered electrocompetent—that is, competent to take up exogenous DNA by electroporation—by various pre-pulse treatments; vectors are introduced by electroporation followed by subsequent outgrowth in selected media. An extensive series of protocols is provided online in "Electroprotocols Online: Collection of Protocols for Gene Transfer" (BioRad, Richmond, Calif., USA) (available at the BioRad web site).

Vectors can be introduced into yeast cells by spheroplasting, treatment with lithium salts, electroporation, or protoplast fusion.

Spheroplasts are prepared by the action of hydrolytic enzymes—a snail-gut extract, usually denoted Glusulase, or Zymolyase, an enzyme from *Arthrobacter luteus*—to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol. For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., Curr. Genet. 16(5-6):339-46 (1989). For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., Methods Enzymol. 194:182-7 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means.

For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPOFECTAMINE Reagent, CELLFECTIN® Reagent, and LIPOFECTIN® Reagent (Invitrogen, Carlsbad, Calif., USA), DOTAP Liposomal Transfection Reagent, FUGENE™ 6, X-tremeGENE Q2, DOSPER, (Roche Molecular Biochemicals, Indianapolis, Ind. USA), Effectene™, PolyFect®, Superfect® (Qiagen, Inc., Valencia, Calif., USA). Protocols for electroporating mammalian cells can be found online in "Electroprotocols Online: Collection of Protocols for Gene Transfer" (Bio-Rad, Richmond, Calif., USA) (available at the BioRad web site).

See also, Norton et al. (eds.), Gene Transfer Methods: Introducing DNA into Living Cells and Organisms, BioTechniques Books, Eaton Publishing Co. (2000) (ISBN 1-881299-34-1), incorporated herein by reference in its entirety.

Other transfection techniques include transfection by particle embardment. See, e.g., Cheng et al., Proc. Natl. Acad. Sci. USA 90(10):4455-9 (1993); Yang et al., Proc. Natl. Acad. Sci. USA 87(24):9568-72 (1990).

Beta protein can be produced according to a variety of techniques well known in the art. Examples include but are not limited to in vitro translation from an appropriate gene construct, as well as production from in vivo host cell expression systems, including bacterial cells (e.g., E. coli, etc.), yeast cells (e.g., S. cerevisiae, etc.), insect cells (e.g., Sf9, etc.), or mammalian cells (e.g., HeLa, COS, CV1; L929, NIH3T3, CHO, etc.) where the bacterial, yeast, insect or mammalian cells contain a suitable beta protein expression vector. Typically, the beta protein produced from the expression systems is purified, using techniques familiar to the skilled artisan.

Beta protein and sequence-altering oligonucleotides of the present invention may be introduced into cells together or separately, according to the needs of the skilled artisan. For example, beta protein and vectors may mixed together in ratios determined by the skilled artisan and then introduced simultaneously into cells, e.g., with a transfection reagent or by electroporation, etc. In other embodiments of the methods of the present invention, beta protein is introduced into cells first, followed at some interval determined by the skilled artisan by the sequence altering oligonucleotides. Alternatively, the sequence-altering oligonucleotides may be introduced before the beta protein. If the beta protein is introduced into the cells by expression from an inducible beta protein gene expression construct residing in the cells, then beta protein expression can be induced before or after introduction of the oligonucleotides. Typically, beta protein expression is induced before introducing sequence altering oligonucleotides.

When it is desirable to express beta protein from a gene, the gene may reside as an episomal element within a cell, or may be integrated into a cell's chromosome. One or multiple copies of a gene for expressing beta protein may be present in either case. Techniques for constructing a beta protein expression construct suitable for purposes of the present invention are within the knowledge of the skilled artisan, as are techniques for preserving the episomal construct within growing cells, and causing a construct to be integrated into a cellular chromosome. Constructs will often contain a promoter, either constitutive or inducible, as well as enhancer elements to stimulate transcription of the beta protein into mRNA. Promoter and enhancer elements can be derived from the same or a different organism as the cell into which the construct is intended to be placed. As an alternative, the construct can lack transcription control elements, in which case the construct is often inserted, according to the knowledge of the skilled artisan, in proximity to native cellular transcription control elements which stimulate transcription of the beta protein gene. Episomal constructs will often additionally contain an origin of replication, allowing the construct to be replicated when the cell divides. Episomal constructs and constructs for which insertion into the chromosome is intended often additionally contain one or more selection markers such that cells containing the construct can be selected for particular growth characteristics, according to the knowledge of the skilled artisan. The expression construct can additionally include translation control regions that increase the efficiency of ribosomal translation (e.g., Kozak sequence), and stabilize the beta protein mRNA. For expression in eukaryotic cells, the beta protein gene can include a nuclear localization signal, such that the protein can be actively imported into the nucleus of the cell.

The examples herein below further demonstrate compositions, assay systems, and methods to optimize the concentration of beta protein to use to achieve enhanced nucleic acid sequence alteration efficiency for an oligonucleotide that introduces a desired target nucleic acid sequence alteration, including, for example, an insertion, deletion, or replacement alteration as described herein as well as oligonucleotides that introduce multiple nucleic acid sequence alterations. One of skill in the art could readily modify one of these systems to assay correction of any target to optimize the concentration of beta protein for introduction of desired nucleic acid sequence alterations using the teachings of this application.

In a second aspect, the present invention provides compositions to enhance the efficiency of oligonucleotide-mediated nucleic acid sequence alteration.

In one embodiment, the composition comprises at least one sequence-altering oligonucleotide—such as a chimeric oligonucleotide, a bifunctional oligonucleotide, or a single-stranded, chemically modified oligonucleotide—and an HDAC inhibitor, such as trichostatin A. In another embodiment, the composition comprises at least one sequence-altering oligonucleotide and beta protein.

The compositions of the present invention may be formulated as pharmaceutical compositions adapted for ex vivo or in vivo use, such as for bathing cells in culture, for microinjection into cells in culture, or for intravenous administration to human beings or animals. Typically, compositions for cellular administration or for intravenous administration into animals, including humans, are solutions in sterile isotonic aqueous buffer. Where necessary, the composition may also include a solubilizing agent and a local anesthetic such as lignocaine to ease pain at the site of the injection. Generally, the ingredients will be supplied either separately or mixed together in unit dosage form, for example, as a dry, lyophilized powder or water-free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection" or saline. Where the composition is to be administered by injection, an ampule of sterile water for injection or saline may be provided so that the ingredients may be mixed prior to administration. Pharmaceutical compositions of this invention comprise a sequence-altering oligonucleotide, any one or more of an HDAC inhibitor, beta protein, or HU and pharmaceutically acceptable salts thereof, and any pharmaceutically acceptable ingredient, excipient, carrier, adjuvant or vehicle.

The pharmaceutical compositions of the present invention adapted for in vivo use are preferably administered to the subject in the form of an injectable composition. The composition is preferably administered parenterally, meaning intravenously, intraarterially, intrathecally, interstitially or intracavitarilly. Pharmaceutical compositions of this invention can be administered to mammals including humans in a manner similar to other diagnostic or therapeutic agents. The dosage to be administered, and the mode of administration will depend on a variety of factors including age, weight, sex, condition of the subject and genetic factors, and will ultimately be decided by medical personnel subsequent to experimental determinations of varying dosage as described herein. In general, dosage required for correction and therapeutic efficacy will range from about 0.001 to 50,000 µg/kg, preferably between 1 to 250 µg/kg of host cell or body mass, and most preferably at a concentration of between 30 and 60 micromolar.

When administering an HDAC inhibitor or HU to animals, the dosage to be administered and the mode of administration will depend on a variety of factors including age, weight, sex, condition of the animal and genetic factors, and will ultimately be decided by veterinary personnel subsequent to experimental determinations of varying dosage as described herein. In general, dosage required for correction and therapeutic efficacy will range from about 0.001 to 1000 mg/kg of body mass, preferably between 10 and 200 mg/kg, and most preferably 50 to 100 mg/kg. When administering an HDAC inhibitor in vitro, dosage can be in the nanomolar to micromolar concentrations, often about 100-200 µM.

In a further embodiment, the compositions of the present invention (and in a further aspect, kits of the present invention), comprise a cell or cell-free extract and an HDAC inhibitor, beta protein, or HU.

Cells for use in the compositions (or kits) of the invention, either intact or in the form of cell extracts that include cellular repair proteins, include cells from any organism including bacteria, fungi, plants, and animals, including humans or other mammals. Cells for use in the kits of the invention include, for example, cultured cells of human liver, lung, colon, cervix, kidney, epithelium, COS-1 and COS-7 cells (African green monkey), CHO-K1 cells (Chinese hamster ovary), H 1299 cells (human epithelial carcinoma, non-small cell lung cancer), C127I (immortal murine mammary epithelial cells), MEF (mouse embryonic fibroblasts), HEC-1-A (human uterine carcinoma), HCT15 (human colon cancer), HCT116 (human colon carcinoma), LoVo (human colon adenocarcinoma), and HeLa (human cervical carcinoma) cancer cells as well as PC12 cells (rat pheochromocytoma) and mammalian ES cells (including human embryonic stem cells).

Cells for use in compositions and kits of the present invention—intact or as extracts that include cellular repair proteins—can also include mammalian embryonic stem (ES) cells. Given current prohibitions in certain jurisdictions, the compositions may include a nonhuman ES cell, such as a nonhuman mammalian ES cell. In other jurisdictions, the compositions may include human ES cells. For example, the compositions may include a human stem cell line that meets U.S. federal funding criteria. The National Institutes of Health is currently compiling a list of these existing stem cell lines (http://escr.nih.gov) which includes those held by the following: BresaGen, Inc., Athens, Ga. (4 lines); CyThera, Inc., San Diego, Calif. (9 lines); Karolinska Institute, Stockholm, Sweden (5 lines); Monash University, Melbourne, Australia (6 lines); National Center for Biological Sciences, Bangalore, India (3 lines); Reliance Life Sciences, Mumbai, India (7 lines); Technion-Israel Institute of Technology, Haifa, Israel (4 lines); University of California, San Francisco, Calif. (2 lines); Goteborg University, Goteborg, Sweden (19 lines); Wisconsin Alumni Research Foundation, Madison, Wis. (5 lines).

In other embodiments, the cells for use in the compositions and kits of the invention can be yeast or other fungal cells, or cells from a plant, including, for example, maize, rice, wheat, barley, soybean, cotton, and potato. Other exemplary plants include those described elsewhere herein.

In yet another aspect, the invention provides kits for targeted sequence alteration.

In one embodiment, the kit comprises at least one sequence-altering oligonucleotide—such as a chimeric oligonucleotide, a bifunctional oligonucleotide, or a single-stranded, chemically modified oligonucleotide—and one or more separately packaged reagents selected from the group consisting of an HDAC inhibitor, such as trichostatin A, HU, and beta protein. The kit optionally further includes instructions for use.

In one embodiment, the kit includes a nucleic acid encoding beta protein. The nucleic acid may be DNA or RNA, such as a beta protein expression vector. The expression vector can be one that resides as an episome within a cell, or alternatively one that integrates into a cell's chromosome or chromosomes. The expression vector can be controlled by an inducible promoter or alternatively by a constitutively active promoter.

In another embodiment, a kit according to the present invention includes a sequence-altering oligonucleotide and a host cell containing a beta protein expression vector.

Kits of the present invention may further advantageously include: means for introducing into a cell the sequence-altering oligonucleotide; means for introducing into a cell beta protein; means for introducing into a cell a nucleic acid encoding beta protein; means for introducing into a cell a beta protein expression construct; cells into which it is desired to introduce a sequence altering oligonucleotide and beta protein; and/or instructions sufficient to direct a skilled artisan how to practice the methods of the present invention. Additional kit components may be provided according to the knowledge and needs of the skilled artisan.

In a further series of embodiments, the kits of the present invention may additionally include reagents for appending LNAs to either or both of the 5' and 3' termini of oligonucleotides, which oligonucleotides are then suitable for use in the gene repair methods of the present invention.

The kits can include the oligonucleotide to be terminally modified. In such embodiments, the sequence of the oligonucleotide will typically have been chosen to effect a nucleic acid sequence alteration that is frequently desired. More typically, however, the kits will not include such an oligonucleotide. In these latter embodiments, the user will provide an oligonucleotide the sequence of which is designed to effect a user-desired nucleic acid sequence alteration. In both series of embodiments, the kit can optionally include one or more oligonucleotides to serve as controls for the terminal modification reactions and/or, optionally, for the subsequent nucleic acid sequence alteration process.

The terminal modification kits of the present invention will include reagents sufficient to append at least one monomeric LNA, often sufficient to append two, three, or more monomeric LNAs, to either or both of the 3' termini of an oligonucleotide or the 5' terminus of an oligonucleotide.

Typically, the reagents will include, as separately packaged compositions, LNA monomers having nucleobases that are separately complementary to each of A, G, T, and C, permitting the user to extend the oligonucleotide at one or both termini without introducing bases noncomplementary to the target, ensuring that the resulting oligonucleotide is complementary to the target nucleic acid at all positions except those desired to be modified by the gene repair process. In kits that permit modification of both 5' and 3' termini, the LNA monomers intended for the 5' terminus may differ in chemistry from those intended for the 3' terminus; in such cases, the monomers respectively intended for 5' and 3' modification will typically be separately packaged from one another.

Kit embodiments that permit 3' terminal modification will typically include a template-independent single-strand polymerase, such as calf thymus terminal deoxynucleotidyl transferase, and LNA monomers that have 5'-triphosphates. Calf thymus terminal deoxynucleotidyl transferase catalyzes the non-specific, template-independent polymerization of nucleoside triphosphates to the 3' terminus of single-stranded DNA. Sambrook, J. and Russell, D. W. (2001) Molecular Cloning: A Laboratory Manual 3rd Edition, Cold Spring Harbor Laboratory Press, Cold Spring Harbor, NY, pp. 9.60-9.61. If 2', 3'-dideoxynucleoside triphosphates are used in the polymerization reaction, a single nucleotide is added to the 3' terminus of the oligonucleotide. Thus, the kit can usefully include such dideoxy LNA monomers, either to the exclusion of, or typically in addition to, LNA monomers that permit further polymerization.

The kits of these embodiments can optionally include a reaction buffer and instructions for performing the enzymatic reaction. Optionally, the kits can include means for terminating the reaction, such as a stop buffer composition, and means for removing reactants to prepare the oligonucleotide for further modification or for use in the nucleic acid sequence alteration methods of the present invention, such as a size-selecting spin column.

5' modification is readily performed on an oligonucleotide that presents a 5' phosphate. Thus, kits intended for 5' modification can usefully include a kinase, such as bacteriophage T4 polynucleotide kinase, and adenosine triphosphate, thus permitting an oligonucleotide that presents a 5' hydroxyl group to be phosphorylated. Sambrook, J. and Russell, D. W. (2001) Molecular Cloning: A Laboratory Manual 3rd Edition, Cold Spring Harbor Laboratory Press, Cold Spring Harbor, N.Y., pp. 9.66-9.69.

Because such reagents are commonly found in molecular biology laboratories, and because oligonucleotides can be ordered from commercial vendors or core facilities already possessing a 5' phosphate, in other embodiments the kits of the present invention will not include a kinase and ATP.

The 5'-phosphorylated oligonucleotide is then activated using a water-soluble carbodiimide in the presence of imidazole to form the 5'-phosphorimidazolide. Chu et al. (1983) Nucleic Acids. Res. 11(18) 6513-6529. The kit will thus typically include, as two separate compositions, a water soluble carbodiimide, such as 1-ethyl-3,3-dimethylaminopropylcarbodiimide, and an imidazole, to be combined with the 5'-phosphorylated oligonucleotide at the time of reaction.

The 5'-phosphorimidazolide oligonucleotide can then further be reacted with an LNA monomer having a nucleophilic group, such as an amine, causing extension of the oligonucleotide with the LNA monomer at its 5' terminus. Kits employing this chemistry for 5' modification will thus typically further include such nucleophilic LNA monomer, such as amino-LNA monomers.

In an alternative approach, a terminally unmodified oligonucleotide can be modified directly at the 5' terminus using an LNA that is activated for reaction with a 5'-hydroxyl group. In such embodiments, activated LNA monomers are provided in the kit.

An example of such an activated form of an LNA monomer is an LNA phosphoramidite. LNA phosphoramidites can be reacted with the 5' terminus of an oligonucleotide that is "protected" at all the nucleobases. Such oligonucleotides can be obtained using standard solid phase synthesis techniques, by cleaving the oligonucleotide from the synthesis support without deprotecting the nucleobases. Such oligonucleotides can readily be so ordered from commercial vendors or core facilities.

Following the reaction of the oligonucleotide with the activated, such as phosphoramidite, LNA monomer, the extended oligonucleotide is oxidized and deprotected prior to use in the gene repair methods of the present invention.

In yet other embodiments of the kits of this aspect of the invention, LNA monomers are provided that have protecting groups to prevent undesirable side reactions, permitting additional chemistries to be used. Appropriate protecting groups for these purposes are well known in the art. See, for example, Protocols for Oligonucleotides and Analogs: Synthesis and Properties, vol 20, (Agrawal, ed.), Humana Press, 1993; Totowa et al. (1993) Tetrahedron 49, 6123; Beaucage and Iyer (1992) Tetrahedron 48, 2223; and Uhlmann and Peyman (1990) Chem. Rev. 90, 543. Removal of these protecting groups prior to further modification of the LNA-modified oligonucleotide or use of the LNA-modified oligonucleotide in gene repair may be a necessary additional step as well, and reagents for effecting such removal can be included in such kits or provided by the user.

In another series of embodiments, the kits of the present invention further comprise a cell or cell-free extract, one or more reagents selected from the group consisting of HDAC inhibitor, beta protein, and HU, and optionally a sequence-altering oligonucleotide and/or instructions for use.

The cell or cell-free extract for the kit of the invention may be derived from any organism and may be directly supplemented with a protein or preparation from the same organism or from a different organism. Such a protein may, for example, be from the RAD52 epistasis group, the mismatch repair group, or the nucleotide excision repair group. In a particularly useful embodiment, the cell or cell-free extract is or is derived from a eukaryotic cell or tissue, in particular, a yeast cell. In alternative embodiments, the kits include, packaged from the cell or cell-free extract, at least one protein from the RAD52 epistasis group, the mismatch repair group, or the nucleotide excision repair group and an HDAC inhibitor, beta protein, or HU.

In another aspect, the invention provides an assay to identify additional chemical compounds that increase the efficiency of oligonucleotide-mediated nucleic acid sequence alteration. Such assay methods comprise contacting a sample with a chemical compound and a sequence altering oligonucleotide in a system known to provide for nucleic acid sequence alteration, and measuring whether the amount of nucleic acid sequence alteration is less, more, or the same as in the absence of the chemical compound. Many suitable assay systems will be apparent to one of skill in the art, including antibiotic resistance (e.g. tetracycline, kanamycin or hygromycin), GFP and FlAsH™ systems disclosed herein and in International Patent Application published as WO 01/73002.

The methods, compositions, and kits of the present invention may be used to alter the genomic sequence of a nonhuman cell, from which nonhuman cell an entire nonhuman animal or plant is then regenerated. A further aspect of the present invention are the non-human animals and the plants produced thereby.

The non-limiting examples set forth herein below further demonstrate methods, compositions, kits, and assay systems, to identify other compounds that enhance nucleic acid sequence alteration efficiency and to select and optimize the concentration required to achieve enhanced nucleic acid sequence alteration efficiency by an oligonucleotide that introduces one or more desired target nucleic acid sequence alterations. One of skill in the art could readily modify one of these systems to assay correction of any desired target to optimize the conditions for introduction of desired nucleic acid sequence alterations using the teachings set forth herein.

EXAMPLE 1

DNA Repair Genes Influence The Ability To Direct Nucleic Acid Sequence Alteration In Vitro In this example, we use chemically modified, nonhairpin, internally unduplexed single-stranded oligonucleotides or chimeric double-hairpin oligonucleotides to measure nucleic acid sequence alteration of episomal target sequences in cell-free extracts from cells with increased or decreased expression of DNA repair genes. These target sequences encode, for example, a kanamycin resistance gene (pKan$^S$m4021), a tetracycline resistance gene, and a fusion between a hygromycin resistance gene and eGFP. In each case, the target gene is non-functional due to at least one point mutation in the coding region.

Preparation and use of cell-free extracts for nucleic acid sequence alteration experiments. We grow yeast cells, for example, into log phase ($OD_{600}$=0.5-0.8) in 2L YPD medium at 30° C. We then centrifuge the cultures at 5000 xg, resuspend the pellets in a 10% sucrose, 50 mM Tris, 1 mM EDTA lysis solution and freeze them on dry ice. After thawing, we add KCl, spermidine and lyticase to final concentrations of 0.25 mM, 5 mM and 0.1 mg/ml, respectively. We incubate the suspension on ice for 60 minutes, add PMSF and Triton X100 to final concentrations of 0.1 mM and 0.1%, respectively, and continue to incubate on ice for 20 minutes. We centrifuge the lysate at 3000 xg for 10 minutes to remove larger debris. We then remove the supernatant and clarify it by centrifuging at 30000 xg for 15 minutes. We then add glycerol to the clarified extract to a concentration of 10% (v/v) and freeze aliquots at −80° C. We determine the protein concentration of the extract by the Bradford assay.

To assay nucleic acid sequence alteration activity, we use 50 μl reaction mixtures comprising 10-30 μg protein of cell-free extract from either a wild-type yeast strain or a yeast strain having a mutation in a gene from the RAD52 epistasis group, the mismatch repair group, or the nucleotide excision repair group; about 1.5 μg chimeric double-hairpin oligonucleotide (KanGG, see FIG. 1) or 0.55 μg single-stranded molecule (3S/25G or 6S/25G, 25-mer oligonucleotides directing the same alteration as KanGG and having 3 or 6 phosphorothioate linkages at each end, respectively); and about 1 μg of plasmid DNA (see FIG. 1) in a reaction buffer comprising 20 mM Tris pH 7.4, 15 mM $MgCl_2$, 0.4 mM DTT, and 1.0 mM ATP. We initiate the reactions by adding cell-free extract and incubating at 30° C. for 45 min. We stop the reaction by placing the tubes on ice and then immediately deproteinize them with two phenol/chloroform (1:1) extractions. We then ethanol precipitate the samples and pellet the nucleic acid at 15,000 r.p.m. at 4° C. for 30 min; wash the pellet with 70% ethanol; resuspend the nucleic acid in 50 μl $H_2O$; and store it at −20° C.

We measure the effect of oligonucleotide concentration on nucleic acid sequence alteration in cell-free extract as follows. We use about 1 μg of plasmid pKsm4021 and varying amounts of oligonucleotide in a 100 μl reaction mixtures comprising 20 mM Tris pH 7.6; 15 mM $MgCl_2$; 1 mM DTT; 0.2 mM spermidine; 2.5 mM ATP; 0.1 mM each CTP, GTP, UTP; 0.01 mM each dATP, dCTP, dGTP and dTTP; 0.1 mM NAD; and 10 μg/ml BSA. We start the reactions by adding 10-80 μg of cell-free extract and incubate the reactions at 30° C for 30 min. We stop the reactions on ice and isolate the plasmid DNA with two phenol and one chloroform extraction followed by ethanol precipitation on dry ice for 1 hr and centrifugation at 4° for 30 min. We then wash the pellet with 70% ethanol, resuspend in 50 μl $H_2O$ and store at −20° C.

Quantification of nucleic acid sequence alteration. We then electroporate 5 μl of plasmid from the resuspension (~100 ng) into 20 μl of DH10B cells in a Cell-Porator apparatus with settings of 400 V, 300 pF, 4 kΩ (Life Technologies). After electroporation, we transfer cells to a 14 ml Falcon snap-cap tube with 1 or 2 ml SOC and shake at 37° C. for 1 h. To enhance the final kanamycin resistant colony counts, we amplify plasmids with altered sequence by adding kanamycin (50 μg/ml) or 3 ml SOC with 10 μg/ml kanamycin and shake the cell suspension for 2 or 3 h more at 37° C. We then directly plate 100 μl aliquots of undiluted cultures on LB agar plates with 50 μg/ml kanamycin and 100 μl aliquots of a 104 dilution on LB agar plates with 100 μg/ml ampicillin. Alternatively, we first centrifuge the cells at 3750 xg and resuspend the pellet in 500 μl SOC. We add 200 μl of the resuspension (undiluted) to kanamycin (50 μg/ml) agar plates and 200 μl of a $10^5$ dilution to ampicillin (100 μg/ml) plates. After overnight 37° C. incubation, we count bacterial colonies using an AccuCount™ 1000 (BioLogics). We measure nucleic acid sequence alteration efficiency as the ratio of the kanamycin resistant colonies to the ampicillin resistant colonies corrected for the dilution.

Alternatively, we use the following procedure. We transform 5 μl of resuspended reaction mixtures (total volume 50 μl) into 20 μl aliquots of electro-competent DH10B bacteria using a Cell-Porator apparatus (Life Technologies). We allow the mixtures to recover in 1 ml SOC at 37° C. for 1 hour at which time we add 50 μg/ml kanamycin or 12 μg/ml tetracycline (for kanamycin or tetracycline plasmids, respectively) and incubate for an additional 3 hours. Prior to plating, we pellet the bacteria and resuspend in 200 μl of SOC. We plate 100 μl aliquots on kanamycin or tetracycline agar plates and 100 μl of a $10^{-4}$ dilution of the cultures on agar plates containing 100 μg/ml of ampicillin. We determine colony counts using an AccuCount™ 1000 plate reader (BioLogics).

For both plating procedures we generally plate in duplicate or triplicate. Each plate contains 200-500 ampicillin resistant colonies or 0-500 tetracycline or kanamycin resistant colonies. We then select resistant colonies for plasmid isolation and DNA sequencing using an ABI Prism kit on an ABI 310 capillary sequencer (PE Biosystems).

Nucleic acid sequence alteration in cell-free extracts from yeast. We use the kanamycin plasmid assay system to test cell-free extracts from the yeast strain LSY678. As shown in Table 1, we observe that the reaction depends on all reaction components. We also generally observe that increasing the amount of oligonucleotide or the amount of extract in the reaction increases the relative correction efficiency. We then analyze the efficiency of nucleic acid sequence alteration in yeast strains deficient for at least one protein from the RAD52 epistasis group, the mismatch repair group, or the nucleotide excision repair group. We find that extracts produced from an msh2 mutant yeast strain (LSY814) show a significant reduction in repair activity similar to the lower gene repair that we see in mammalian cells deficient in MSH2p (Table 2). We observe that cell-free extracts from rad57 or rad59 mutant strains show little change in nucleic acid sequence alteration activity and that cell-free extracts from rad23 or rad54 mutant strains show a slight increase in nucleic acid sequence alteration activity relative to a strain with functional copies of these genes. However, we observe elevated nucleic acid sequence alteration frequencies using cell-free extracts from rad51 or rad52 mutant strains. In particular, we observe that the Δrad52 (LSY386) strain exhibits about 5-fold to about 25-fold higher repair frequency. In all samples, the range of ampicillin resistance colonies is 500-600 per plate with kanamycin colonies between 10 and 300.

Gene repair depends on the dose of repair proteins. We examine the activity of an extract lacking RAD52 in more detail. First, we observe that repair of pK$^S$m4021 depends on the addition of all three components: plasmid, oligonucleotide and extract (Table 3). We also observe that the repair is dose-dependent and proportional to the amount of LSY386 (Δrad52) extract present in a reaction where two extracts are mixed (Table 3). We confirm that RAD52 is present in these extracts by western blot analyses. We observe a similar effect on repair in cell-free extract when a rad52 mutant strain lacking RAD52 is mixed with a rad23 mutant strain (YELO37C) instead of LSY678.

Finally, we analyze nucleic acid sequence alteration efficiency of cell-free extracts from LSY386 or LSY678 containing a plasmid expressing RAD52. We observe that the expression of RAD52 reduces the level of nucleic acid sequence alteration activity in extracts made from either LSY386 or LSY678. In LSY386, the level of repair drops to near wild-type levels while the level in LSY678 is reduced to 4-fold below wild-type levels (Table 3). We perform western blot analysis on these strains and the level of RAD52 protein expression in these strains is approximately equal. These results indicate that expression of the RAD52 gene suppresses oligonucleotide-directed nucleic acid sequence alteration. We also analyze the DNA sequence of the target plasmid from three colonies and observe that the targeted base is precisely changed even in samples in which the extract came from Δrad51 or Δrad23. Hence, target specificity is maintained despite the mutations and the differences in nucleic acid sequence alteration frequency.

TABLE 1

Gene repair using Saccharomyces cerevisiae extracts

| Plasmid (1 μg) | Chimeric Oligonucleotide (μg) | Extract (μg) | Relative Frequency kan$^r$/amp$^r$(×10$^{-5}$) |
|---|---|---|---|
| pK$^S$m4021 | 1 (Kan GG) | — | 0.002 |
| pK$^S$m4021 | — | 20 | 0.0 |
| — | 1 (Kan GG) | 20 | 0.0 |
| — | — | — | 0.0 |
| pK$^S$m4021 | 1 (Kan GG) | 1 | 0.32 |
| pK$^S$m4021 | 1 (Kan GG) | 10 | 3.66 |
| pK$^S$m4021 | 1 (Kan GG) | 20 | 7.601 |
| pK$^S$m4021 | 0.5 (Kan GG) | 10 | 1.89 |
| pK$^S$m4021 | 1.0 (Kan GG) | 10 | 2.78 |
| pK$^S$m4021 | 2.0 (Kan GG) | 10 | 4.005 |
| pK$^S$m4021 | 1 (Kan CG) | — | 0.0 |
| pK$^S$m4021 | 1 (Kan CG) | 20 | 0.003 |

Chimeric oligonucleotides at varying levels are incubated with plasmid pK$^S$m4021 and the indicated amounts of cell-free extracts from Saccharomyces cerevisiae (LSY678) for 45 minutes at 30° C. We isolate, purify and electroporate the plasmids into E. coli (DH10B) and quantify resistant colonies using an automatic plate reader. Relative frequency is presented as kanamycin resistant colonies divided by ampicillin resistant colonies (×10$^{-5}$). Oligonucleotide KanCG has the same sequence as KanGG except there is no mismatch and KanCG does not correct the mutation. Each data point is presented as the average of 5 independent experiments.

TABLE 2

Gene repair using mutant strains of Saccharomyces cerevisiae

| Plasmid | Oligonucleotide | Source of Extract | Relative Correction Efficiency |
|---|---|---|---|
| pK$^S$m4021 | KanGG | — | 0.0 |
| pK$^S$m4021 | — | LSY678 | 0.002 |
| pK$^S$m4021 | KanGG | LSY678 (wild type) | 1.17 |
| pK$^S$m4021 | KanGG | LSY814 (Δmsh2) | 0.79 |
| pK$^S$m4021 | KanGG | LSY402 (Δrad51) | 5.15 |
| pK$^S$m4021 | KanGG | LSY386 (Δrad52) | 25.7 |
| pK$^S$m4021 | KanGG | XS827-18C (Δrad54) | 1.36 |
| pK$^S$m4021 | KanGG | YDR076W (Δrad55) | 1.27 |
| pK$^S$m4021 | KanGG | LSY407 (Δrad57) | 2.13 |
| pK$^S$m4021 | KanGG | LSY837 (Δrad59) | 0.35 |
| pK$^S$m4021 | KanGG | YELO37C (Δrad23) | 1.04 |

Reaction mixtures (20 μl) containing 1 μg plasmid pK$^S$m4021 and 1 μg oligonucleotide KanGG are mixed with 10 μg of a cell-free extract from the indicated yeast strains. After a 45 minute incubation at 30° C., we isolate the plasmid DNA and electroporate into E. coli (DH10B). We count kanamycin resistant colonies on agar plates containing 50 μg/ml kanamycin. Plasmids from duplicate reaction mixtures are also electroporated into E. coli (DH10B) and plated on ampicillin containing plates. We determine relative activity by dividing Kanr by Ampr colony numbers. These numbers reflect an average of five reactions.

TABLE 3

Extracts from LSY386 (Δrad52) exhibit higher levels of gene repair.

| Plasmid | Oligonucleotide | Source of First Extract | Source of Second Extract | Relative Correction Efficiency |
|---|---|---|---|---|
| pK$^S$m4021 | — | — | — | 0.0 |
| — | KanGG | — | — | 0.0 |
| pK$^S$m4021 | KanGG | — | — | 0.003 |
| pK$^S$m4021 | KanGG | LSY678 (wild type) | — | 1.08 |
| pK$^S$m4021 | KanGG | LSY386 (Δrad52) | — | 26.7 |
| pK$^S$m4021 | KanGG | LSY386 (2 μg) | LSY678 (8 μg) | 2.91 |
| pK$^S$m4021 | KanGG | LSY386 (4 μg) | LSY678 (6 μg) | 5.45 |
| pK$^S$m4021 | KanGG | LSY386 (6 μg) | LSY678 (4 μg) | 10.47 |
| pK$^S$m4021 | KanGG | LSY386 (8 μg) | LSY678 (2 μg) | 14.36 |
| pK$^S$m4021 | KanGG | LSY386 (2 μg) | YELO37C (8 μg) | 1.85 |
| pK$^S$m4021 | KanGG | LSY386 (4 μg) | YELO37C (6 μg) | 3.71 |
| pK$^S$m4021 | KanGG | LSY386 (6 μg) | YELO37C (4 μg) | 9.22 |
| pK$^S$m4021 | KanGG | LSY386 (8 μg) | YELO37C (2 μg) | 16.95 |
| pK$^S$m4021 | KanGG | LSY386 | — | 19.9 |
| pK$^S$m4021 | KanGG | LSY386·p52 | — | 2.31 |
| pK$^S$m4021 | KanGG | LSY678 | — | 1.63 |
| pK$^S$m4021 | KanGG | LSY678·p52 | — | 0.41 |

Reaction mixtures and processing for colonies are as described in the legend to Table 1 with the following exceptions. We use cell-free extracts from yeast strains containing mutations as follows: LSY678 (wild type), LSY386 (Δrad52), and YELO37C (Δrad23). We use either 10 μg of extract or the amounts indicated. The reactions identified as LSY386·p52 contain a cell-free extract from a Δrad52 strain (LSY386) harboring a plasmid which expresses RAD52 protein. The reactions identified as LSY678·p52 contain a cell-free extract from wild-type strain (LSY678) harboring a plasmid which expresses RAD52 protein.

EXAMPLE 2

DNA Repair Genes Influence the Ability to Direct Nucleic Acid Sequence Alteration in Vivo In this example, we use chemically modified, internally unduplexed, single-stranded oligonucleotides or double-hairpin chimeric oligonucleotides and measure nucleic acid sequence alteration of target nucleic acid sequences in cells with increased or decreased expression of DNA repair genes. These target nucleic acid sequences encode, for example, a fusion between a hygromycin resistance gene and eGFP which is non-functional due to at least one point mutation in the coding region. The target sequences may be either episomal or chromosomal (including, e.g., nuclear, mitochondrial or plastidic). Nucleic acid sequence alteration of episomal targets is generally slightly more efficient (less than two-fold) than nucleic acid sequence alteration of chromosomal targets. Modifications to the oligonucleotides and construction of target vectors are disclosed in the copending International Patent Application WO 01/73002 of Kmiec et al. entitled "Targeted Chromosomal Genomic Alterations with Modified Single Stranded Oligonucleotides," filed Mar. 27, 2001, the disclosure of which is hereby incorporated by reference.

In vivo assay systems. To monitor nucleic acid sequence alteration of episomal targets, we employ a yeast system using the plasmids pAURHYG(rep)eGFP, which contains a point mutation in the hygromycin resistance gene, pAURHYG(ins)eGFP, which contains a single-base insertion in the hygromycin resistance gene and pAURHYG(Δ)eGFP which has a single base deletion (shown in FIG. 2). We also use the same plasmid containing a functional copy of the hygromycin-eGFP fusion gene, designated pAURHYG(wt)eGFP, as a control. These plasmids are collectively designated pAURHYG(x)eGFP. These plasmids also contain an aureobasidinA resistance gene. In pAURHYG(rep)eGFP, hygromycin resistance gene function and green fluorescence from the eGFP protein are restored when a G at position 137, in codon 46 of the hygromycin B coding sequence, is converted to a C thus removing a premature stop codon in the hygromycin resistance gene coding region. In pAURHYG(ins)eGFP, hygromycin resistance gene function and green fluorescence from the eGFP protein are restored when an A inserted between nucleotide positions 136 and 137, in codon 46 of the hygromycin B coding sequence, is deleted and a C is substituted for the T at position 137, thus correcting a frameshift mutation and restoring the reading frame of the hygromycin-eGFP fusion gene. In pAURHYG(Δ)eGFP, hygromycin resistance gene function and green fluorescence from eGFP are restored when a C is inserted at the site of the single nucleotide deletion.

We synthesize the set of three yeast expression constructs pAURHYG(rep)eGFP, pAURHYG(Δ)eGFP, pAURHYG(ins)eGFP, that contain a point mutation at nucleotide 137 of the hygromycin-B coding sequence as follows: (rep) indicates a T137→G replacement, (Δ) represents a deletion of G137 and (ins) represents an A insertion between nucleotides 136 and 137. We construct this set of plasmids by excising the respective expression cassettes by restriction digest from pHyg(x)eGFP and ligation into pAUR123 (PanVera®, CA). We digest 10 μg pAUR123 vector DNA as well as 10 μg of each pHyg(x)eGFP construct with KpnI and SalI (NEB). We gel purify each of the DNA fragments and prepare them for enzymatic ligation. We ligate each mutated insert into pAUR123 vector at a 3:1 molar ratio using T4 DNA ligase (Roche). We screen clones by restriction digest, confirm by Sanger dideoxy chain termination sequencing and purify plasmid DNA using a Qiagen® maxiprep kit.

To monitor nucleic acid sequence alteration of chromosomal targets, we typically employ a yeast system in which we monitor chromosomal genes such as CYC1 or we use integrational plasmids such as those designated pAUR101-HYG(x)eGFP. These plasmids do not replicate in yeast. These plasmids comprise the HYG(x)eGFP fusion proteins used in the pAURHYG(x)eGFP episomal plasmid system (shown in FIG. 2) and an aureobasidinA resistance gene. Therefore, like pAURHYG(x)eGFP, these constructs can also be used to monitor all types of nucleic acid sequence alterations, i.e. replacements, insertions and deletions. In addition to this construct, we monitor nucleic acid sequence alteration of specific yeast genes including, for example, CYC1.

Figure 8A:
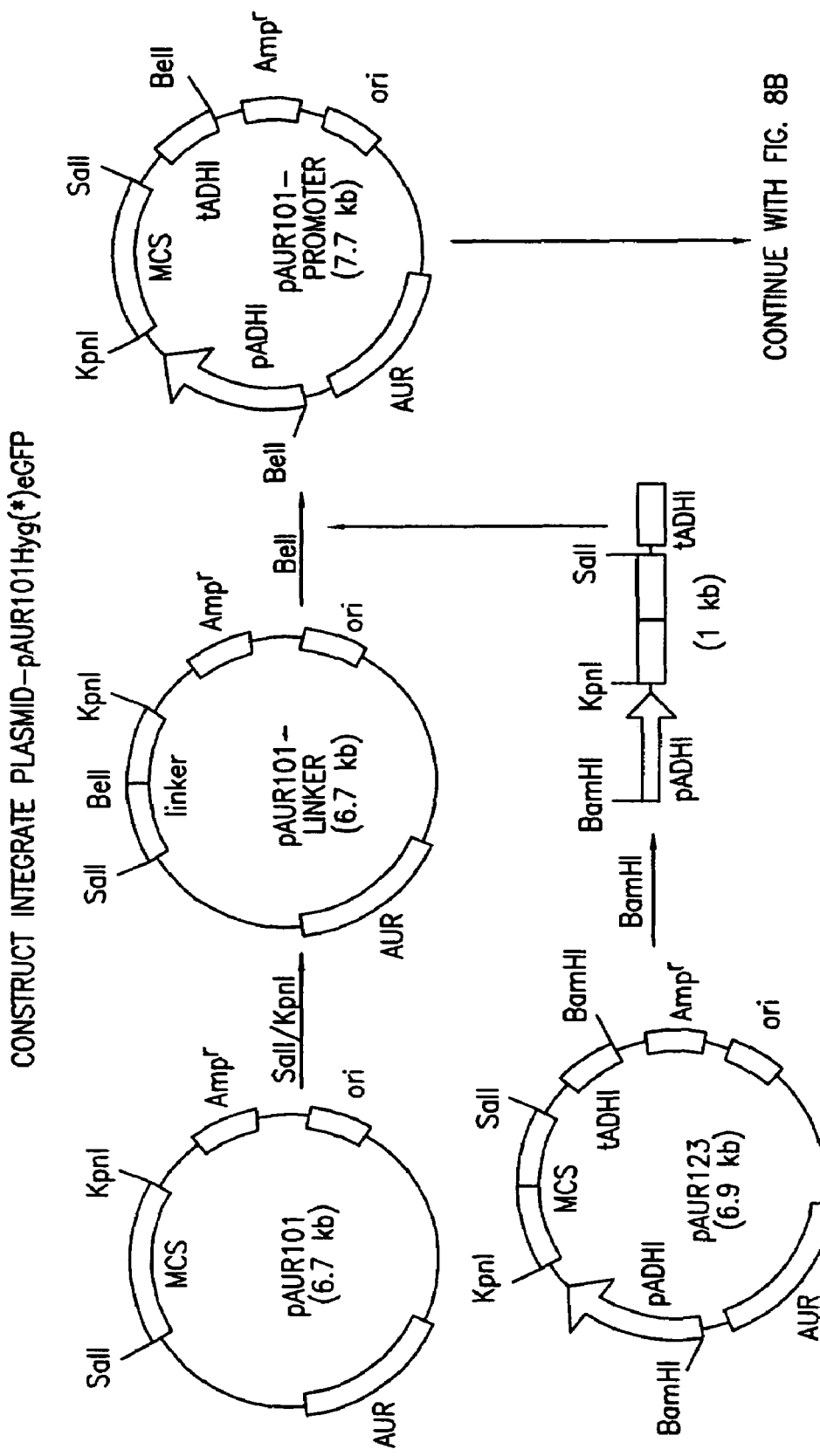
FIGS. 8A and 8B. Construction ofpAUR101-HYG(x)eG-FPplasmid.
Figure 8B:
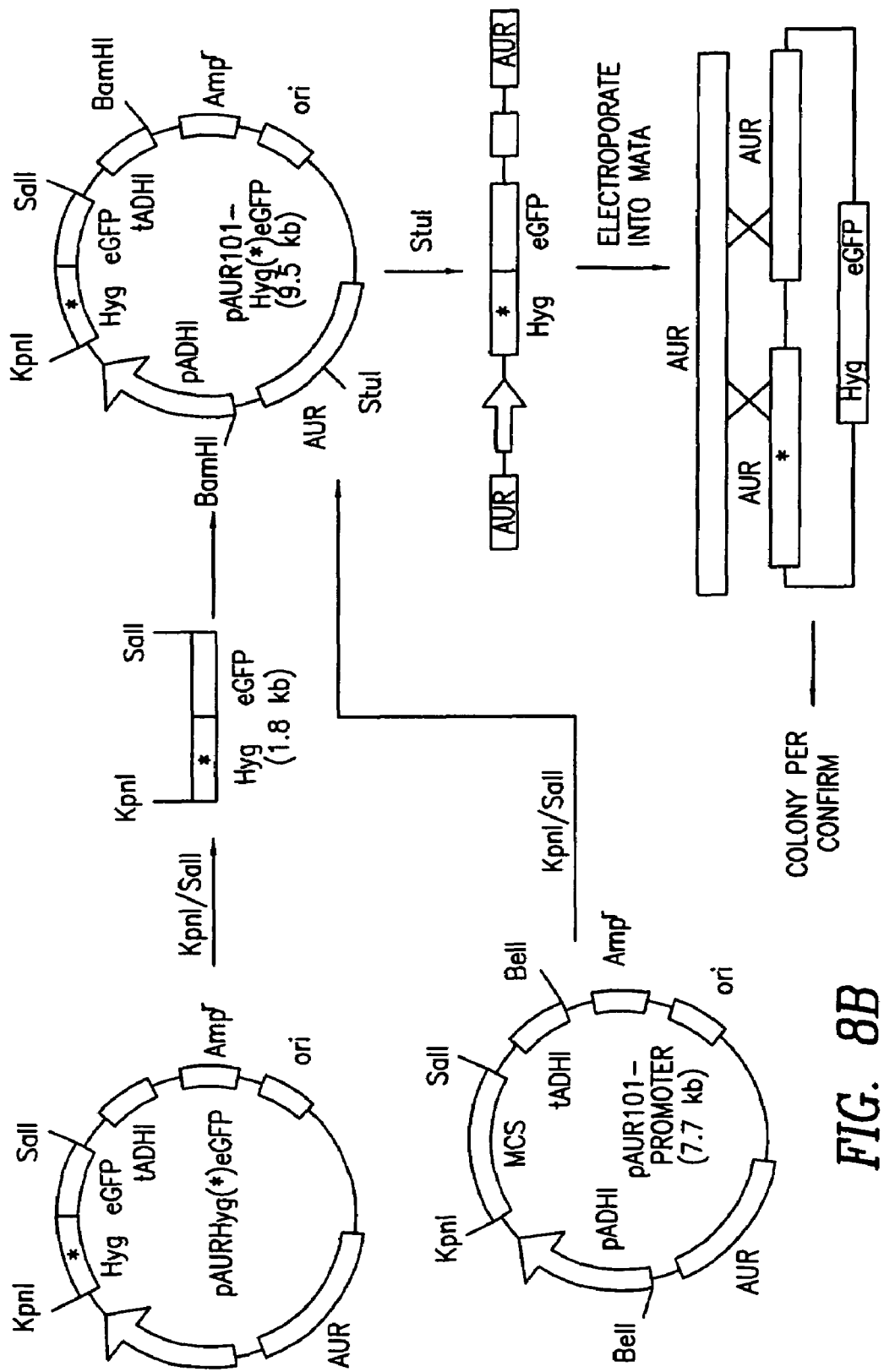

We construct the pAUR101-HYG(x)eGFP plasmids as diagrammed in FIG. 8. Briefly, we digest 10 μg pAUR101 (PanVera® Corp.) with SalI and KpnI and ligate a linker comprising a unique BclI restriction site. We then digest 10 μg of the resulting plasmid ("pAUR101-linker") with BclI and ligate in a 1 kb BamHI fragment from pAUR123. The BamHI fragment from pAUR123 comprises a multiple-cloning site as well as the ADH1 promoter and terminator regions. We then digest 10 μg of this plasmid ("pAUR101-promoter") with SalI and KpnI and ligate in a 1.8kb SalI|KpnI fragment from pAURHYG(x)eGFP which contains the HYG(x)eGFP fusion protein. The resulting plasmid is pAUR101-HYG(x)eGFP. All DNA fragments are gel purified after restriction enzyme digestion to prepare them for enzymatic ligation. All ligations are performed using T4 DNA ligase (Roche). Clones are screened by restriction digest and confirmed by Sanger dideoxy chain termination sequencing.

We integrate the plasmids into the genome of wild-type yeast cells as well as yeast strains with mutations in a variety of genes, including, for example, genes of the RAD52 epistasis group, the mismatch repair group, and the nucleotide excision repair group. We integrate the plasmids into the yeast genome by linearizing 10 μg of the plasmid by digestion with StuI and electroporating the linearized plasmid into the yeast cells. The plasmid integrates by homologous recombination at the wild-type AUR-C (aureobasidinA) locus. We then select on aureobasidinA to identify clones in which the plasmid has integrated. We confirm that the plasmid has integrated by PCR analysis and by performing Southern blots. We obtain yeast strains with single as well as multiple integrated copies of the plasmid.

We also synthesize a set of yeast expression plasmids to express genes from the RAD52 epistasis group, the mismatch repair group, and the nucleotide excision repair group. We use the plasmid pYN132 which has the promoter from the TPL1 gene, which directs high-level constitutive expression of genes cloned downstream (Alber et al. J. Mol. Appl. Genet. 1: 419-34 (1982)). We construct the expression plasmids by digesting 10 μg pYN132 DNA as well as 10 μg of a PCR product containing one of the DNA repair protein with NdeI and XhoI (NEB). We gel purify each of the DNA fragments and prepare them for ligation. We ligate the PCR product into the pYN132 vector at a 3:1 molar ratio using T4 DNA ligase (Roche). We screen clones by restriction digest, confirm the clone by Sanger dideoxy chain termination sequencing and purify plasmid DNA using a Qiagen® maxiprep kit.

We use this system to assay the ability of modified oligonucleotides (shown in FIG. 3) to support nucleic acid sequence alteration in a variety of host cell backgrounds including wild-type, mutants and cells expressing additional gene(s). These oligonucleotides direct correction of the mutation in pAURHYG(rep)eGFP as well as the mutation in pAURHYG(ins)eGFP or pAURHYG(Δ)eGFP. The first of these oligonucleotides, HygE3T/74, is a 74-base oligonucleotide with the sequence directing nucleic acid sequence alteration centrally positioned. The second oligonucleotide, designated HygE3T/74NT, is the complement of HygE3T/74. The third oligonucleotide, designated Kan70T, is a non-specific, control oligonucleotide which is not complementary to the target sequence. Alternatively, an oligonucleotide of identical sequence but lacking a mismatch to the target or a completely phosphorothioate-modified oligonucleotide or a completely 2-O-methylated modified oligonucleotide or a completely LNA-modified oligonucleotide may be used as a control. We also use this system with chimeric RNA-DNA double-hairpin oligonucleotides.

Oligonucleotide synthesis and cells. We synthesize and purify the oligonucleotides using available phosphoramidites on controlled pore glass supports. After deprotection and detachment from the solid support, each oligonucleotide is gel-purified using, for example, procedures such as those described in Gamper et al., *Biochem.* 39: 5808-5816 (2000). We determine the concentration of the oligonucleotides spectrophotometrically (33 or 40 μg/ml per $A_{260}$ unit of single-stranded or hairpin oligomer, respectively). Plasmids used for assay are maintained stably at low copy number under aureobasidin selection in yeast (*Saccharomyces cerevisiae*) strain LSY678 (wild type) which optionally may contain additional gene mutations or may be engineered to express additional protein(s).

Plasmids and oligonucleotides are introduced into yeast cells by electroporation as follows: to prepare electrocompetent yeast cells, we inoculate 10 ml of YPD media from a single colony and grow the cultures overnight with shaking at 300 rpm at 30° C. We then add 30 ml of fresh YPD media to the overnight cultures and continue shaking at 30° C. until the $OD_{600}$ is between 0.5 and 1.0 (3-5 hours). We then wash the cells by centrifuging at 4° C. at 3000 rpm for 5 minutes and twice resuspending the cells in 25 ml ice-cold distilled water. We then centrifuge at 4° C. at 3000 rpm for 5 minutes and resuspend in 1 ml ice-cold 1 M sorbitol and then finally centrifuge the cells at 4° C. at 5000 rpm for 5 minutes and resuspend the cells in 120 μl 1 M sorbitol. To transform electrocompetent cells with plasmids or oligonucleotides, we mix 40 μl of cells with 5 μg of nucleic acid, unless otherwise stated, and incubate on ice for 5 minutes. We then transfer the mixture to a 0.2 cm electroporation cuvette and electroporate with a BIO-RAD Gene Pulser apparatus set at 1.5 kV, 25 μF, 200 Ω for one five-second pulse. We then immediately resuspend the cells in 1 ml YPD supplemented with 1M sorbitol and incubate the cultures at 30° C. with shaking at 300 rpm for 6 hours. We then spread 200 μl of this culture on selective plates containing 300 μg/ml hygromycin and spread 200 μl of a $10^5$ dilution of this culture on selective plates containing 500 ng/ml aureobasidinA and/or hygromycin and incubate at 30° C. for 3 days to allow individual yeast colonies to grow. We then count the colonies on the plates and calculate the nucleic acid sequence alteration efficiency by determining the number of hygromycin resistance colonies per $10^5$ aureobasidinA resistant colonies.

Nucleic acid sequence alteration to repair different mutations in wild-type *Saccharomyces cerevisiae*. We test the ability of oligonucleotides shown in FIG. 3 to alter all three target plasmids in vivo using wild-type yeast strain LSY678. These target plasmids contain a point mutation (pAURHYG(rep)eGFP), a deletion mutation (pAURHYG(Δ)eGFP) or an insertion mutation (pAURHYG(ins)eGFP). We also test oligonucleotides targeting opposite strands of the target DNA to identify any strand-specific effects and we test the oligonucleotide at a range of concentration to determine the optimum concentration for gene repair.

As shown in Table 4 (set forth below at the end of this Example), we observe that oligonucleotides targeting either strand direct correction of all three types of mutations. The data indicate that the point mutation in pAURHYG(rep)eGFP is corrected more efficiently than the insertion mutation in pAURHYG(ins)eGFP, which in turn is corrected more efficiently than the deletion mutation in pAURHYG(Δ)eGFP. In addition, with all three assay plasmids we observe that the optimal oligonucleotide concentration for nucleic acid sequence alteration in this system is 5 μg. We note, however, that the oligonucleotides are capable of effecting repair over a wide range of concentrations. Finally, we observe that the oligonucleotide with sequence complementary to the sense strand of the target DNA, HygE3T/74NT, repairs all three types of target mutations more effectively than the complementary oligonucleotide, HygE3T/74. The fold difference in repair efficiency using HygE3T/74NT relative to using HygE3T/74 is indicated in the final column of Table 4.

We also test the ability of oligonucleotides shown in FIG. 3 to alter all three target mutations in strains comprising the integrated pAUR101-HYG(x)eGFP plasmids. We test multiple concentrations of oligonucleotides targeting either strand of the DNA duplex target. The results of these types of experiments with the replacement mutation in pAUR101-HYG(rep)eGFP are shown in Table 14 including data on how to determine an optimized oligonucleotide concentration. We observe that oligonucleotides targeting either strand direct correction of the point mutation in the integrated pAUR101-HYG(rep)eGFP plasmid and that the optimal oligonucleotide concentration for nucleic acid sequence alteration with this chromosomal target is 7.5 μg. We note again, however, that the oligonucleotides are capable of effecting repair over a wide range of concentrations. We observe that the oligonucleotide with sequence complementary to the sense strand of the target DNA, HygE3T/74NT, repairs the chromosomal target mutation more effectively than the complementary oligonucleotide, HygE3T/74, at all concentrations tested. The fold difference in correction efficiency using HygE3T/74NT relative to using HygE3T/74 is indicated in the final column of Table 14.

Nucleic acid sequence alteration in strains with mutation(s) in gene(s) of the RAD52 epistasis group. We test the ability of oligonucleotides shown in FIG. 3 to alter a nucleic acid sequence in vivo using yeast strains with additional mutation(s) in gene(s) of the RAD52 epistasis group. In these experiments we use derivatives of LSY678 (wild type) with a mutation in one or more of the genes of the RAD52 epistasis group and containing the target plasmid pAURHYG(rep)eGFP, pAURHYG(ins)eGFP or pAUR HYG(Δ)eGFP. We electroporate these cells with 5 μg of HygE3T/74 and plate on hygromycin and aureobasidinA to obtain the efficiency of nucleic acid sequence alteration. The results of these experiments for plasmid pAURHYG(rep)eGFP, pAURHYG(ins)eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that the efficiency of nucleic acid sequence alteration is reduced or unchanged in a yeast strain with a mutation in RAD51, RAD52, RAD54, RAD55, RAD59, RAD50, MRE11 or XRS2. The efficiency of nucleic acid sequence alteration that we observe in these experiments in strains with mutations in either RAD57 or a double mutant in rad51/52 is reduced when using pAURHYG(ins)eGFP or pAUR HYG(Δ)eGFP as the target plasmid, but, surprisingly, we observe an increase in the efficiency of nucleic acid sequence alteration in these strains when using pAURHYG (rep)eGFP as the target. We observe that nucleic acid sequence alteration using pAURHYG(rep)eGFP as the target is reduced in yeast strains with mutations in RAD54 or RAD55. We also perform control experiments with LSY678 yeast cells containing the plasmid pAURHYG(wt)eGFP. With this strain we observe that even without added oligonucleotides, there are too many hygromycin resistant colonies to count. We test yeast strains with mutations in both single genes in the RAD52 epistasis group as well as yeast strains with mutations in two or more of the genes. We test the ability of these yeast strains to correct all of the pAURHYG (x)eGFP mutations.

Nucleic acid sequence alteration in strains with mutation(s) in mismatch repair gene(s). We test the ability of oligonucleotides shown in FIG. 3 to alter a nucleic acid sequence in vivo using yeast strains with additional mutation(s) in mismatch repair gene(s) containing the plasmid pAURHYG(x)eGFP. We electroporate these cells with 5 μg of HygE3T/74 and plate on hygromycin and aureobasidinA to obtain the efficiency of nucleic acid sequence alteration. For example, the results of these experiments for plasmid pAURHYG(rep)eGFP, pAURHYG(ins)eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that nucleic acid sequence alteration occurs at a reduced efficiency in strains with mutations in MSH2, MSH3 or MSH6 and at an increased efficiency in strains with a mutation in PMS1. We observe the same general effects, although at different relative efficiencies, in experiments using either plasmid pAURHYG(rep)eGFP, plasmid pAURHYG(ins)eGFP or pAUR HYG(Δ)eGFP as the target. In control experiments with LSY678 yeast cells containing the plasmid pAURHYG(wt)eGFP, we again observe that, even without added oligonucleotides, there are too many hygromycin resistant colonies to count. We test yeast strains with mutations in both single mismatch repair genes as well as yeast strains with mutations in two or more of the genes. We test the ability of these yeast strains to correct all of the pAURHYG(x)eGFP mutations.

Nucleic acid sequence alteration in strains with mutation(s) in nucleotide excision repair gene(s). We test the ability of oligonucleotides shown in FIG. 3 to alter a nucleic acid sequence in vivo using yeast strains with additional mutation(s) in nucleotide excision repair gene(s) containing the plasmid pAURHYG(x)eGFP. We electroporate these cells with 5 μg of HygE3T/74 and plate on hygromycin and aureobasidinA to obtain the efficiency of nucleic acid sequence alteration. For example, the results of these experiments for plasmid pAURHYG(rep)eGFP, pAURHYG(ins)eGFP and pAUR HYG(Δ)eGFP are shown in Table 5, Table 6 and Table 7, respectively. We also monitor nucleic acid sequence alteration efficiency on chromosomal targets in yeast strains with mutation(s) in gene(s) of the RAD52 epistasis group.

These data indicate that nucleic acid sequence alteration occurs at a reduced efficiency in strains with mutations in RAD10, RAD2, or RAD23. The efficiency of nucleic acid sequence alteration observed in these experiments in a strain with a mutation in RAD1 is reduced when using either pAURHYG(ins)eGFP or pAUR HYG(Δ)eGFP as the target plasmid, but increased when using pAURHYG(rep)eGFP as the target. We observe that nucleic acid sequence alteration is reduced in a yeast strain with a mutation in EXO1 using pAURHYG(rep)eGFP or pAURHYG(ins)eGFP as the target. We also perform control experiments with LSY678 yeast cells containing the plasmid pAURHYG(wt)eGFP which yield too many hygromycin resistant colonies to count. We test yeast strains with mutations in both single nucleotide excision repair genes as well as yeast strains with mutations in two or more of the genes. We test the ability of these yeast strains to correct all of the pAURHYG(x)eGFP mutations.

Figure 6:
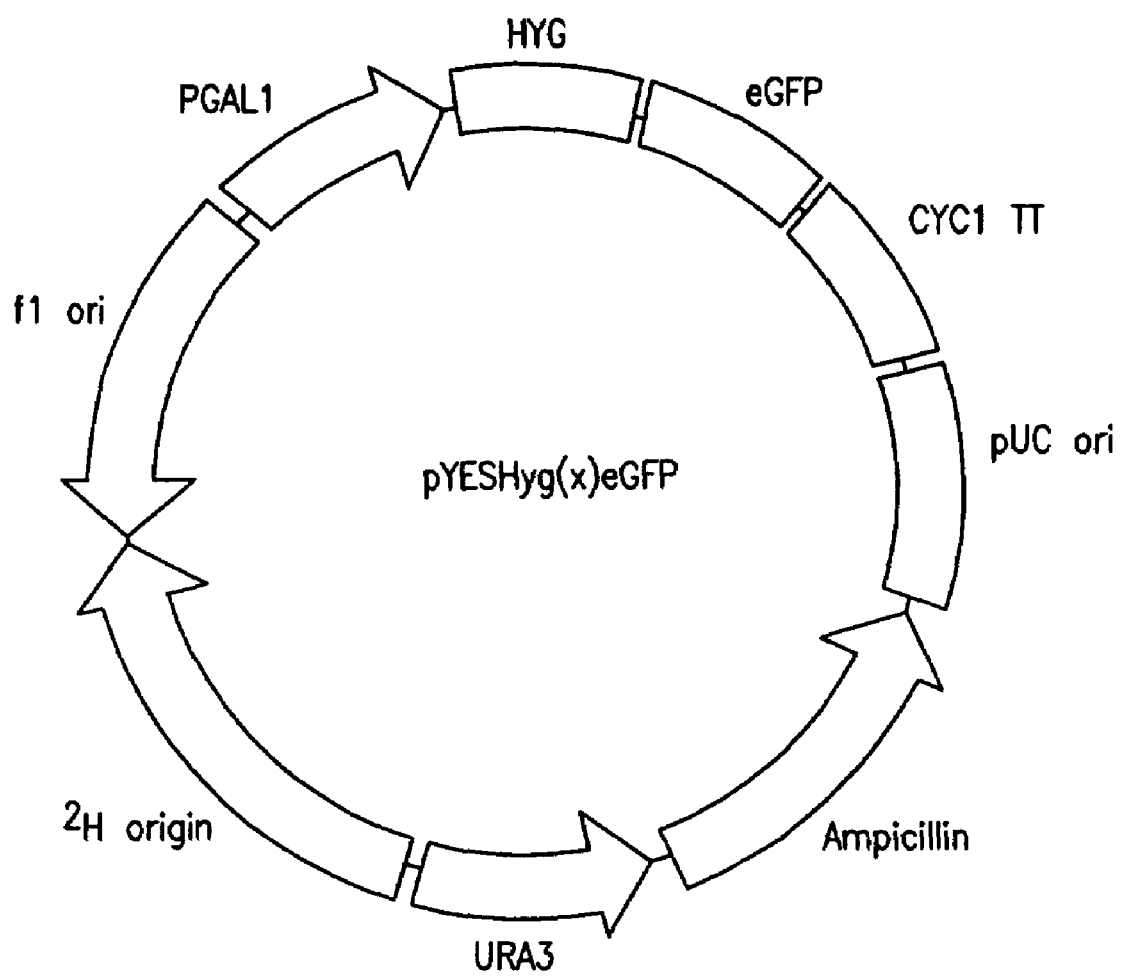
FIG. 6. pYESHyg(x)eGFP plasmid. This plasmid is a construct similar to the pAURHyg(x)eGFP construct shown in FIG. 7, except the promoter is the inducible GAL1 promoter. This promoter is inducible with galactose, leaky in the presence of raffinose, and repressed in the presence of dextrose.
Figure 7:
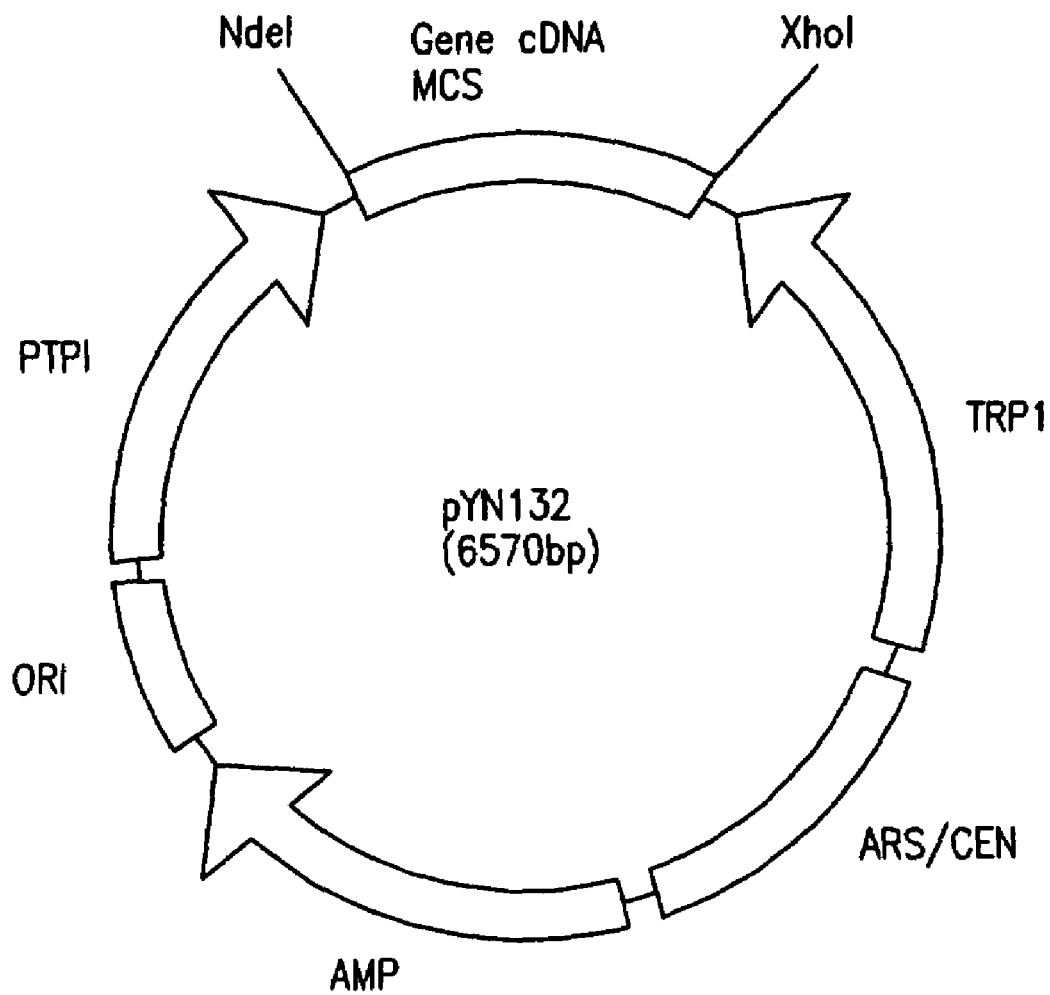
FIG. 7. pYN132 plasmid. This figure shows the plasmid structure including the constitutive promoter from the TPL1 gene, which directs expression of the cDNA cloned downstream.

Nucleic acid sequence alteration in yeast strains expressing DNA repair gene(s) from plasmids. We test the effect on nucleic acid sequence alteration efficiency of increasing expression of DNA repair genes, including genes in the RAD52 epistasis group, mismatch repair genes and nucleotide excision repair genes. We test the effect of expression of these genes both individually and in groups of two or more. We employ plasmids with inducible promoters, for example, the plasmid described in FIG. 6, directing expression of DNA repair genes. Alternatively, we use plasmids with constitutive promoters to direct expression of DNA repair genes, for example, the plasmids described in FIGS. 1, 2 and 4.

We test the ability of oligonucleotides shown in FIG. 3 to alter a nucleic acid sequence in vivo using yeast strains with additional copies of gene(s) of the RAD52 epistasis group, the mismatch repair group, or the nucleotide excision repair group. In these experiments we use derivatives of LSY678 wild type containing the plasmid pYN132 or the derivatives of pYN132 comprising a cloned copy of a gene from the RAD52 epistasis group, the mismatch repair group, or the nucleotide excision repair group. These strains also contain one of the plasmids pAURHYG(rep)eGFP, pAURHYG(ins) eGFP or pAURHYG(del)eGFP as a reporter for monitoring nucleic acid sequence alteration. Alternatively, these strains comprise the one or more copies of the integrational plasmid pAUR101-HYG(x)eGFP as a reporter for monitoring nucleic acid sequence alteration. We confirm expression of the cloned DNA repair gene in these strains by northern blot and/or western blot analysis.

We introduce, for example, plasmids expressing RAD10, RAD51, RAD52, RAD54RAD55, MRE11, PMS1, REC2 or XRS2 into LSY678 (wild type) and monitor the ability of the single-stranded oligonucleotide vector, Hyg3S/74NT, to direct nucleic acid sequence alteration in the pAURHYG(ins) eGFP plasmid. As shown in Table 9 and Table 12, results from these experiments indicate that additional expression of any one of the RAD10, RAD51, RAD52, RAD54, MRE11, PMS1 or XRS2 genes results in an increase in nucleic acid sequence alteration efficiency ranging from 1.2-fold (RAD10) to 7.5-fold (RAD51). These data clearly indicate that additional copies of particular DNA repair proteins results in increased nucleic acid sequence alteration efficiency. We also introduce plasmids expressing multiple proteins into LSY678 (wild type) and monitor the efficiency of nucleic acid sequence alteration as shown in Table 10. We also test other genes from the RAD52 epistasis group, the mismatch repair group, or the nucleotide excision repair group for enhancement of nucleic acid sequence alteration efficiency.

We test nucleic acid sequence alteration efficiency as described above using yeast strains further comprising mutation(s) in the RAD52 epistasis group, the mismatch repair group, or the nucleotide excision repair group. For example, we introduce pYN132-derived plasmids expressing RAD10, RAD51, RAD52, RAD54, RAD55, MRE11, PMS1, REC2 or XRS2 into LSY678 strains with mutations in RAD51, RAD52, MRE1 1 or PMS1. We then monitor the ability of the single-stranded oligonucleotide vector, Hyg3S/74NT, to direct nucleic acid sequence alteration in the pAURHYG(x) eGFP plasmid. As shown in Table 11, Table 13 and Table 15, we observe that strains with mutations in RAD51, RAD52, MRE1 1 or PMS1 containing pYN132 exhibit reduced correction efficiency relative to the wild type containing pYN132 shown in Table 9. These data are consistent with results from mutant strains shown in Table 6. In general, we observe that expressing RAD10, RAD51, RAD52, RAD54, MRE11 or PMS1 in these yeast strains results in increased nucleic acid sequence alteration efficiency relative to the mutant with the empty pYN132 vector. These data indicate that additional expression of these genes results in enhancement of nucleic acid sequence alteration efficiency in the mutants as it does in the wild type. We observe that a RAD52 mutant expressing RAD51 from a plasmid gives very high correction efficiency. We observe that a PMS1 mutant expressing RAD51 from a plasmid gives the highest correction efficiency of any strain tested. We also test the effect of expressing multiple proteins in mutant yeast stains and monitor the efficiency of nucleic acid sequence alteration.

We also monitor nucleic acid sequence alteration efficiency on chromosomal targets in yeast strains with additional copies of gene(s) of the RAD52 epistasis group, the mismatch repair group, or the nucleotide excision repair group. For example, we introduce pYN132-derived plasmids expressing RAD51, RAD52, RAD54, RAD51 +RAD54, RAD51+ RAD52, MRE11, XRS2 or MRE11 +XRS2 into yeast strains containing integrated copies of the pAUR101-HYG(x)eGFP plasmids. The results from an experiment using a strain with integrated pAUR101-HYG(rep)eGFP are shown in Table 16. These results are consistent with results observed with episomal target experiments.

We also determine nucleic acid sequence alteration efficiency on chromosomal target sequences as described above using yeast strains comprising mutation(s) in the RAD52 epistasis group, the mismatch repair group or the nucleotide excision repair group. For example, we introduce pYN132-derived plasmid(s) expressing RAD51, RAD52, RAD54, MRE11, PMS1, REC2 or XRS2 into LSY678 strains with an integrated copy of pAUR101-HYG(x)eGFP and mutation(s) in one or more of the RAD51, RAD52, MRE11 and PMS1 genes. We then monitor the ability of the single-stranded oligonucleotide vector, Hyg3S/74NT, to direct nucleic acid sequence alteration in the integrated pAUR101-HYG(x) eGFP plasmid.

We also test the effect of heterologous expression of DNA repair genes from other organisms, including, for example, other fungi, animals, plants and bacteria.

We also use additional oligonucleotides to assay the ability of individual oligonucleotides to correct multiple mutations in the pAURHYG(x)eGFP plasmid contained in yeast strains with altered expression or activity of gene(s) in the RAD52 epistasis group, the mismatch repair group and/or the nucleotide excision repair group. These include, for example, one that alters two basepairs that are 3 nucleotides apart is a 74-mer with the sequence 5'-CTCGTGCTTTCAGCTTC-GATGTAGGAGGGCGTGGGTACGTCCT-GCGGGTAAATAGCT GCGCCGATGGTTTCTAC-3'(SEQ ID NO: 17); a 74-mer that alters two basepairs that are nucleotides apart with the sequence 5'-CTCGTGCTTTCAGCT-TCGATGTAGGAGGGCGTGGATACGTCCT-GCGGGTAAA<u>C</u>AGCT GCGCCGATGGTTTCTAC-3' (SEQ ID NO: 18); and a 74-mer that alters two basepairs that are 27 nucleotides apart with the sequence 5'-CTCGT-GCTTTCAGCTTCGATGTAGGAGGGCGTG-GATACGTCCTGCGGGTAAATAGCTG CGCCGA <u>C</u>GGTTTCTAC (SEQ ID NO: 19). The nucleotides in these oligonucleotides that direct alteration of the target sequence are underlined and in boldface. These oligonucleotides are modified in the same ways as the previously described oligonucleotides.

We also test the ability of oligonucleotides shown in FIG. 1 to alter a nucleic acid sequence in vivo using yeast strains containing the plasmid pAURNeo(x)FlAsH™ (FIG. 4) and which also have altered expression or activity of gene(s) in the RAD52 epistasis group, the mismatch repair group and/or the nucleotide excision repair group. This plasmid is constructed by inserting a synthetic expression cassette containing a neomycin phosphotransferase (kanamycin resistance) gene and an extended reading frame that encodes a receptor for the FlAsH™ ligand into the pAUR123 shuttle vector (PanVera® Corp., Madison, Wis.). We make constructs with the same mutation as in pK$^S$m4021. The resulting construct replicates in S. cerevisiae at low copy number, confers resistance to aureobasidinA and constitutively expresses the Neo(x) FlAsH™ fusion product from the ADH1 promoter. By extending the reading frame of this gene to code for a unique peptide sequence capable of binding a small ligand to form a fluorescent complex, restoration of expression by correction of the stop codon can be detected in real time using confocal microscopy. Upon correction of the truncated Neo(-)Fl-AsHTM product to generate the Neo(+)FlAsH™ fusion product the translated fusion protein binds a ligand (FlAsH™-EDT2) imparting a green fluorescence onto the cells. Additional constructs using any target gene fused to the FlAsHTM peptide may be made using this model system to test additional nucleic acid sequence alteration events.

To detect the presence of the Neo(+)FlAsH™ fusion product in yeast cells, we prepare loading buffer by mixing FlAsH™ ligand into YPD containing 1 M sorbitol and 20 μM Disperse 3. The ligand molecules are mixed into the YPD at 1 μM FlAsHTm-EDT2 and 10 μM 1,2 ethanedithiol (EDT) (Sigma). We then mix 100 μl of cells with an equal volume of wash buffer comprising HBS, 1 mM sodium pyruvate, 10 μM EDT, 1 M sorbitol and 20 μM Disperse 3. We then image the cells with a Zeiss LSM510 laser scanning microscope on a Zeiss Axiovert 100 m using the 488/568 nm excitation line of an Omnichrome Ar-Kr laser with appropriate emission filters (505-550 nm bandpass for FlAsH™-EDT2 binding). We simultaneously acquire laser scanning transmitted or differential interference contrast images with all fluorescent images using 488 nm excitatory. We load samples into a Lab-Tek II chambered #1.5 Coverglass system (Nalge Nunc International, Ill.) and image them using a Zeiss 63× C-Apochromet water immersion lens (NA 1.2). All samples, including positive and negative controls, are integrated under identical conditions (laser power, pinhole, PMT gap offset, etc.) for a given set of experiments.

We observe correction of a mutation in the neomycin phosphotransferase gene (Neo) harbored in yeast strain LSY678 using a FlAsH-EDT2 model system. We electroporate KanGG or another oligonucleotide directing nucleic acid sequence alteration into either LSY386 or LSY678 containing stable copies of the pAURNeo(-)FlAsH™ plasmid. We measure uptake of oligonucleotide using Texas Red conjugated oligonucleotide and optimize electroporation conditions so that over 80% of the surviving cells receive the oligonucleotide. In the absence of KanGG, or another oligonucleotide directing nucleic acid sequence alteration, we observe only a low level of auto-fluorescence after addition of FlAsH™-EDT2 in both LSY678 (FIG. 5A) and LSY386

Figure 5:
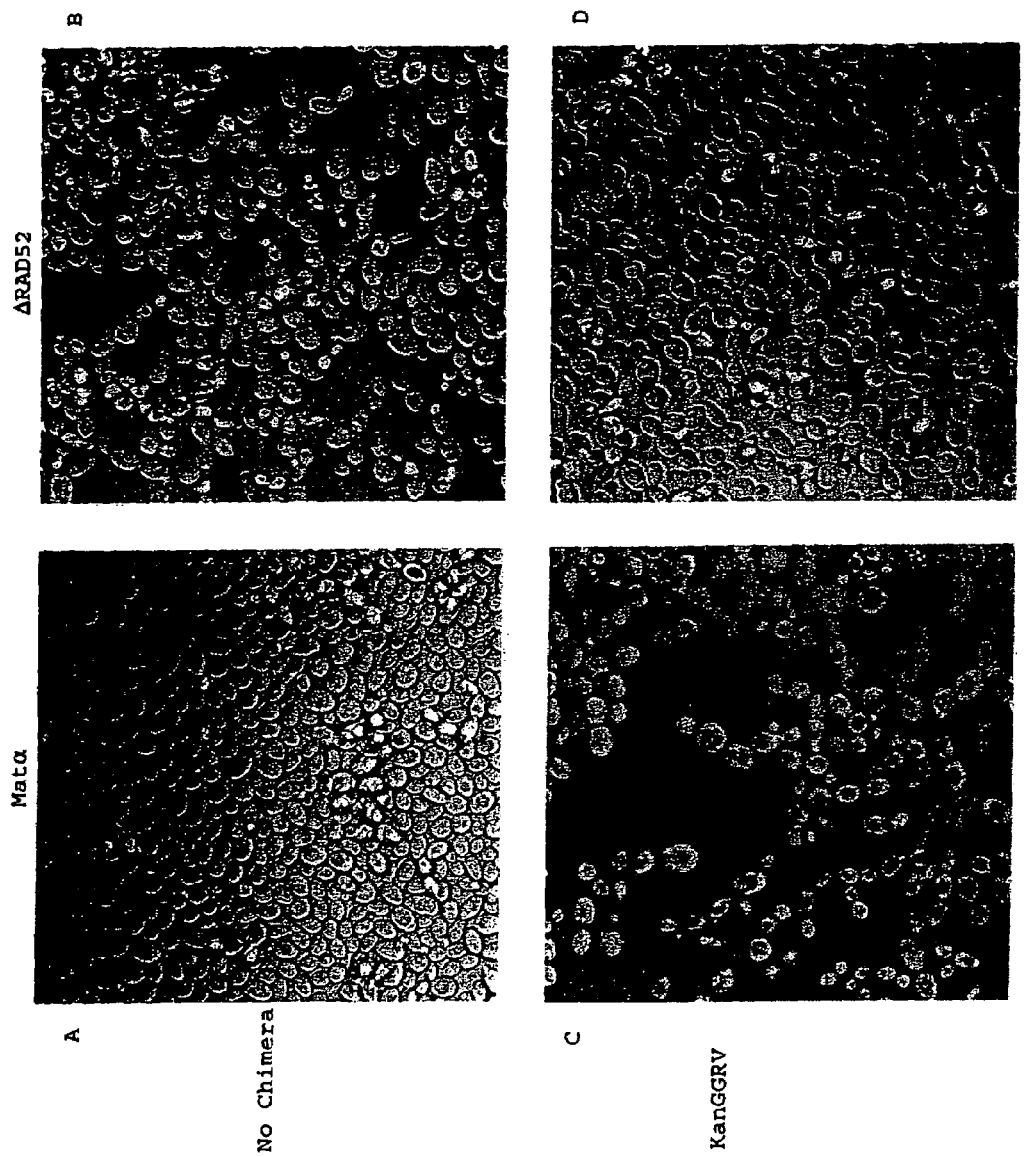
FIG. 5. Fluorescent microscopy of targeting in the FlAsH™ system. This figure shows confocal microscopy of yeast strains before and after transfection by DNA/RNA chimeric oligonucleotide kanGGrv. Converted yeast cells are indicated by bright green fluorescence. (A) Upper left: wild type, nontargeted. Upper right: Δrad52, nontargeted. (C) Lower left: wild type, targeted. (D) Lower right: Δrad52, targeted.

(FIG. 5B) by confocal microscopy. However, when we introduce KanGG into the cells, we observe many corrected cells in both LSY678 and LSY378 as seen in FIG. 5C and FIG. 5D, respectively. We see a significant increase in the number of cells exhibiting green fluorescence in the LSY378 strain lacking RAD52 (FIG. 5D) relative to the LSY678 strain (FIG. 5C). This result reflects a higher degree of gene repair in the strain lacking RAD52 gene function. Correction of pAUR-Neo(−)FlASH™ also confers resistance to G418 selection in yeast cells. Therefore we grow representative samples exhibiting green fluorescence on agar plates containing G418. We then determine the DNA sequence of the plasmid in these cells. The sequence analysis illustrates that the targeted base is changed from a G to a C as designed in plasmids isolated after G418 selection. We perform similar experiments in yeast strains with altered levels of expression or activity of other proteins in the RAD52 epistasis group, the mismatch repair group and the nucleotide excision repair group.

Oligonucleotides targeting the sense strand direct nucleic acid sequence alteration more efficiently in yeast mutants. We compare the ability of single-stranded oligonucleotides to target each of the two strands of the target sequence of pAURHYG(ins)eGFP, pAURHYG(rep)eGFP or pAURHYG(Δ)eGFP present in LSY678 mutant strains with increased or decreased expression of DNA repair genes. For example, the results of an experiment performed with yeast strains having mutations in RAD1 and RAD10 are presented in Table 8. The data from this experiment indicate that an oligonucleotide, HygE3T/74NT, with sequence complementary to the sense strand (i.e. the strand of the target sequence that is identical to the mRNA) of the target sequence facilitates gene correction approximately ten-fold more efficiently than an oligonucleotide, HygE3T/74, with sequence complementary to the strand that serves as the template for the synthesis of RNA. However, regardless of the reduced efficiency observed in yeast strains with mutations in DNA repair genes, the oligonucleotides are clearly still able to target either strand of the target sequence. In addition, the role of transcription of the target gene is investigated using plasmids with inducible promoters such as that described in FIG. 6.

Influence of DNA repair genes in other cells. In addition to testing the effect of DNA repair genes in the above-described yeast assay system, we test the effect of altering the expression or the activity of DNA repair genes in other cells, including, for example, other fungi, animal, plant and bacterial cells. We use other cells with normal DNA repair genes as well as cells that have altered levels or activity of DNA repair genes, including, for example, human and bacterial cells with mutations in the homologous genes or expressing additional copies of the homologous genes. For example, we use cells that are transiently or stably transformed with vectors that express either native or heterologous DNA repair genes. To monitor nucleic acid sequence alteration in these cells, we employ a reporter-gene assay system, for example, kanamycin resistance, hygromycin resistance or GFP expression. Alternatively, we assay the ability of an oligonucleotide to direct nucleic acid sequence alteration of a target present in the genome of the target cell, for example, we monitor conversion of the sickle T (βS) mutation in the β-globin gene to the normal A (βA) allele or vice-versa.

TABLE 4

Gene repair of different mutations in wild-type *Saccharomyces cerevisiae*

| Amount of Oligonucleotide (μg) | Correcting Oligonucleotide Tested | | |
|---|---|---|---|
| | HygE3T/74 | HygE3T/74NT | Fold |
| Repair of pAURHYG(rep)eGFP | | | |
| 0 | 0* | 0 | 0x |
| 1.0 | 5 (0.03) | 238 (1.47) | 47.6x |
| 2.5 | 99 (0.61) | 704 (4.37) | 7.1x |
| 5.0 | 204 (1.26) | 1,406 (8.73) | 6.8x |
| 7.5 | 69 (0.42) | 998 (6.20) | 14.5x |
| 10.0 | 19 (0.12) | 261 (1.62) | 13.7x |
| Repair of pAURHYG(Δ)eGFP | | | |
| 0 | 0 | 0 | 0x |
| 1.0 | 1 (0.01) | 1 (0.01) | 1.0x |
| 2.5 | 18 (0.11) | 68 (0.42) | 3.8x |
| 5.0 | 70 (0.43) | 308 (1.91) | 4.4x |
| 7.5 | 47 (0.29) | 276 (1.71) | 5.9x |
| 10.0 | 11 (0.07) | 137 (0.85) | 12.5x |
| Repair of pAURHYG(ins)eGFP | | | |
| 0 | 0 | 0 | 0x |
| 1.0 | 5 (0.03) | 45 (0.28) | 9.0x |
| 2.5 | 47 (0.29) | 387 (2.4) | 8.2x |
| 5.0 | 199 (1.24) | 623 (3.87) | 3.1x |
| 7.5 | 54 (0.34) | 398 (2.47) | 7.4x |
| 10.0 | 17 (1.10) | 271 (1.68) | 15.9x |

*Average colony count on hygromycin plates from four experiments is shown. Numbers in parentheses indicate the number of hygromycin-resistant colonies per aureobasidin-resistant colony.

TABLE 5

Nucleic acid sequence alteration directing correction of the mutation in pAURHYG(rep)eGFP

| Yeast Strain* | Colonies on Hygromycin | Colonies on Aureobasidin (/10⁵) | Correction Efficiency | Fold |
|---|---|---|---|---|
| wild type | 1,218 | 286 | 4.26 | 1x |
| RAD52 Epistasis Group Mutants | | | | |
| rad51 | 104 | 168 | 0.62 | 0.14x |
| rad52 | 266 | 81 | 3.29 | 0.77x |
| rad51/52 | 212 | 39 | 5.45 | 1.28x |
| rad54 | 2 | 103 | 0.02 | 0x |
| rad55 | 0 | 1,230 | 0 | 0x |
| rad57 | 984 | 57 | 17.26 | 4.05x |
| rad59 | 1,198 | 392 | 3.06 | 0.71x |
| mre11 | 12 | 18 | 0.63 | 0.15x |
| rad50 | 336 | 58 | 2.09 | 0.49x |
| xrs2 | 29 | 44 | 0.66 | 0.15x |
| Mismatch Repair Group Mutants | | | | |
| Msh2 | 0 | 976 | 0 | 0x |
| Msh3 | 0 | 1,035 | 0 | 0x |
| Msh6 | 1,270 | 541 | 2.35 | 0.55x |
| Pms1 | 2,280 | 20 | 114 | 26.76x |
| Nucleotide Excision Repair Mutants | | | | |
| Rad1 | 1,380 | 391 | 8.52 | 2.00x |
| rad10 | 54 | 361 | 0.15 | 0.04x |

TABLE 5-continued

Nucleic acid sequence alteration directing correction of the mutation in pAURHYG(rep)eGFP

| Yeast Strain* | Colonies on Hygromycin | Colonies on Aureobasidin (/10⁵) | Correction Efficiency | Fold |
|---|---|---|---|---|
| Rad2 | 919 | 243 | 3.78 | 0.89x |
| rad23 | 66 | 151 | 0.44 | 0.10x |
| exo1 | 486 | 124 | 3.92 | 0.92x |

*Each strain is wild type except for the indicated mutation(s). The mutations used in these experiments are generally knockout mutations.

TABLE 6

Nucleic acid sequence alteration directing correction of the mutation in pAURHYG(ins)eGFP

| Yeast Strain* | Colonies on Hygromycin | Colonies on Aureobasidin (/10⁵) | Correction Efficiency | Fold |
|---|---|---|---|---|
| wild type | 256 | 74 | 3.46 | 1x |
| RAD52 Epistasis Group Mutants | | | | |
| rad51 | 19 | 32 | 0.59 | 0.17x |
| rad52 | 31 | 36 | 0.86 | 0.24x |
| rad51/52 | 3 | 86 | 0.3 | 0.01x |
| rad54 | 0 | 170 | 0 | 0x |
| rad55 | 0 | 32 | 0 | 0X |
| rad57 | 34 | 103 | 0.33 | 0.10x |
| rad59 | 116 | 47 | 2.47 | 0.71x |
| mre11 | 3 | 34 | 0.09 | 0.03x |
| rad50 | 1 | 17 | 0.06 | 0.02x |
| xrs2 | 6 | 168 | 0.04 | 0.01x |
| Mismatch Repair Group Mutants | | | | |
| msh2 | 0 | 51 | 0 | 0x |
| msh3 | 1 | 18 | 0.05 | 0.02x |
| msh6 | 0 | 49 | 0 | 0x |
| pms1 | 111 | 6 | 18.5 | 5.35x |
| Nucleotide Excision Repair Mutants | | | | |
| rad1 | 52 | 88 | 0.59 | 0.17x |
| rad10 | 14 | 101 | 0.14 | 0.04x |
| rad2 | 113 | 63 | 1.79 | 0.52x |
| rad23 | 1 | 144 | 0.01 | 0x |
| Exo1 | 2 | 197 | 0.01 | 0x |

*Each strain is wild type except for the indicated mutation(s). The mutations used in these experiments are generally knockout mutations.

TABLE 7

NUCLEIC ACID SEQUENCE ALTERATION DIRECTING CORRECTION OF THE MUTATION IN PAURHYG(Δ)EGFP

| Yeast Strain* | Fold Alteration in Correction Efficiency |
|---|---|
| wild type | 1x |
| RAD52 Epistasis Group Mutants | |
| rad51 | 0.47x |
| rad52 | 0.05x |
| rad51/52 | 0.13x |
| mre11 | 1.10x |
| Mismatch Repair Group Mutants | |
| msh2 | 0x |
| msh3 | 0.02x |
| msh6 | 0x |
| Nucleotide Excision Repair Mutants | |
| rad1 | 0x |
| rad10 | 0.04x |

*Each strain is wild type except for the indicated mutation(s). The mutations used in these experiments are generally knockout mutations.

TABLE 8

ALTERATION WITH AN OLIGONUCLEOTIDE TARGETING THE SENSE STRAND IS MORE EFFICIENT

| | Colonies on Hygromycin | | |
|---|---|---|---|
| Yeast Strain** | Kan70T | HygE3T/74 | HygE3T/74NT |
| rad1 | 0 | 3 | 53 (15x)* |
| rad10 | 0 | 2 | 14 (6x)* |

*The numbers in parentheses represent the fold increase in efficiency for targeting the non-transcribed strand as compared to the other strand of a DNA duplex that encodes a protein.
**Each strain is wild type except for the indicated mutation(s). The mutations used in these experiments are generally knockout mutations.

TABLE 9

NUCLEIC ACID SEQUENCE ALTERATION IN YEAST STRAINS WITH INCREASED LEVELS OF DNA REPAIR PROTEINS

| Yeast Strain* | Hyg3S/74NT (μg) | Hyg$^r$ | Aur$^r$ (10⁴) | Correction efficiency (1/10⁵) | Fold |
|---|---|---|---|---|---|
| Wild type/pYN132 | 0 | 0 | 931 | 0 | N/A |
| Wild type/pYN132 | 5 | 249 | 801 | 3.1 | 1 |
| Wild type/pYNRAD51 | 5 | 2,700 | 1,152 | 23.4 | 7.5 |
| wild type/pYNRAD52 | 5 | 1,512 | 748 | 20.3 | 6.5 |
| wild type/pYNRAD55 | 5 | 283 | 1,016 | 2.8 | 0.9 |
| wild type/pYNMRE11 | 5 | 920 | 728 | 12.6 | 4.1 |
| wild type/pYNPMS1 | 5 | 406 | 804 | 5.0 | 1.6 |

*All strains also contain pAURHyg(ins)eGFP as the target for correction. All yeast strains are wild type for all DNA repair proteins and contain plasmids expressing DNA repair proteins as indicated.

TABLE 10

NUCLEIC ACID SEQUENCE ALTERATION IN YEAST STRAINS WITH INCREASED LEVELS OF MULTIPLE DNA REPAIR PROTEINS

| Yeast Strain* | Hyg3S/74NT (μg) | Hyg$^r$ | Aur$^r$ (10⁴) | Correction efficiency (1/10⁵) | Fold |
|---|---|---|---|---|---|
| wild type/pYN132 | 5 | 330 | 141 | 23.4 | 1 |
| wild type/pYNRAD51 | 5 | 1,360 | 109 | 124.77 | 5.33x |
| wild type/pYNRAD54 | 5 | 886 | 70 | 126.57 | 5.41x |
| wild type/pYNMRE11 | 5 | 456 | 74 | 61.62 | 2.63x |
| wild type/pYNRAD51 + pYNRAD54 | 5 | 978 | 78 | 125.38 | 5.36x |
| wild type/pYNRAD51 + pYNMRE11 | 5 | 236 | 69 | 34.2 | 1.46x |

TABLE 10-continued

NUCLEIC ACID SEQUENCE ALTERATION IN YEAST STRAINS WITH INCREASED LEVELS OF MULTIPLE DNA REPAIR PROTEINS

| Yeast Strain* | Hyg3S/74NT (μg) | Hyg$^r$ | Aur$^r$ ($10^4$) | Correction efficiency ($1/10^5$) | Fold |
|---|---|---|---|---|---|
| wild type/pYNRAD54 + pYNMRE11 | 5 | 412 | 159 | 25.91 | 1.11x |
| wild type/pYNRAD51 + pYNRAD54 + pYNMRE11 | 5 | 1,120 | 71 | 157.75 | 6.74x |

*All strains also contain pAURHyg(ins)eGFP as the target for correction. All yeast strains are wild type for all DNA repair proteins and contain plasmids expressing DNA repair proteins as indicated.

TABLE 11

NUCLEIC ACID SEQUENCE ALTERATION IN YEAST STRAINS WITH INCREASED LEVELS OF DNA REPAIR PROTEINS

| Yeast Strain* | Hyg3S/74NT (μg) | Hyg$^r$ | Aur$^r$ ($10^4$) | Correction efficiency ($1/10^5$) | Fold |
|---|---|---|---|---|---|
| rad51/pYN132 | 0 | 0 | 1,012 | 0 | N/A |
| rad51/pYN132 | 5 | 18 | 708 | 0.25 | 1 |
| rad51/pYNRAD51 | 5 | 159 | 1,392 | 1.14 | 4.6 |
| rad51/pYNRAD52 | 5 | 39 | 1,586 | 0.24 | 1 |
| rad51/pYNRAD55 | 5 | 26 | 1,372 | 0.19 | 0.8 |
| rad51/pYNMRE11 | 5 | 8 | 426 | 0.18 | 0.7 |
| rad51/pYNPMS1 | 5 | 33 | 984 | 0.33 | 1.3 |
| rad52/pYN132 | 0 | 0 | 518 | 0 | N/A |
| rad52/pYN132 | 5 | 140 | 644 | 2.17 | 1 |
| rad52/pYNRAD51 | 5 | 3,532 | 832 | 42.4 | 19.3 |
| rad52/pYNRAD52 | 5 | 195 | 684 | 2.85 | 1.3 |
| rad52/pYNRAD55 | 5 | 69 | 308 | 2.24 | 1.0 |
| rad52/pYNMRE11 | 5 | 63 | 122 | 5.16 | 2.4 |
| rad52/pYNPMS1 | 5 | 67 | 145 | 4.62 | 2.1 |
| mre11/pYN132 | 0 | 0 | 302 | 0 | N/A |
| mre11/pYN132 | 5 | 2 | 260 | 0.077 | 1 |
| mre11/pYNRAD51 | 5 | 1 | 235 | 0.042 | 0.6 |
| mre11/pYNRAD52 | 5 | 3 | 135 | 0.022 | 2.8 |
| mre11/pYNRAD55 | 5 | 20 | 217 | 0.922 | 11.9 |
| mre11/pYNMRE11 | 5 | 57 | 588 | 0.969 | 12.6 |
| mre11/pYNPMS1 | 5 | 1 | 147 | 0.067 | 0.9 |

*All strains also contain pAURHyg(ins)eGFP as the target for correction. All yeast strains are wild type except for a single mutation in the indicated DNA repair protein and contain plasmids expressing wildtype DNA repair proteins as indicated. The mutations used in these experiments are generally knock-out mutations.

TABLE 12

NUCLEIC ACID SEQUENCE ALTERATION IN YEAST STRAINS WITH INCREASED LEVELS OF DNA REPAIR PROTEINS

| Yeast Strain* | Hyg3S/74 NT (μg) | Hyg$^r$ | Aur$^r$ ($10^4$) | Correction efficiency ($1/10^5$) | Fold |
|---|---|---|---|---|---|
| wild type/pYN132 | 0 | 0 | 931 | 0 | N/A |
| wild type/pYN132 | 5 | 827 | 740 | 11.17 | 1 |
| wild type/pYNRAD10 | 5 | 1,112 | 812 | 13.69 | 1.2 |
| wild type/pYNRAD54 | 5 | 4,320 | 970 | 44.54 | 4.0 |
| wild type/pYNREC2 | 5 | 152 | 686 | 2.22 | 0.20 |
| wild type/pYNXRS2 | 5 | 937 | 670 | 13.98 | 1.25 |
| wild type/pYNPRAD51 + RAD52 | 5 | 1,042 | 908 | 11.48 | 1.02 |

*All strains also contain pAURHyg(ins)eGFP as the target for correction. All yeast strains are wild type for all DNA repair proteins and contain plasmids expressing DNA repair proteins as indicated

TABLE 13

NUCLEIC ACID SEQUENCE ALTERATION IN YEAST STRAINS WITH INCREASED LEVELS OF DNA REPAIR PROTEINS

| Yeast Strain* | Hyg3S/74NT (μg) | Hyg$^r$ | Aur$^r$ ($10^4$) | Correction efficiency ($1/10^5$) | Ford |
|---|---|---|---|---|---|
| Δrad51/pYN132 | 0 | 0 | 1,012 | 0 | N/A |
| Δrad51/pYN132 | 5 | 50 | 576 | 0.87 | 1 |
| Δrad51/pYNRAD10 | 5 | 21 | 548 | 0.38 | 0.44 |
| Δrad51/pYNRAD54 | 5 | 10 | 683 | 0.15 | 0.17 |
| Δrad51/pYNREC2 | 5 | 28 | 456 | 0.61 | 0.77 |
| Δrad51/pYNXRS2 | 5 | 15 | 890 | 0.17 | 0.19 |
| Δrad52/pYN132 | 0 | 0 | 518 | 0 | N/A |
| Δrad52/pYN132 | 5 | 57 | 700 | 0.81 | 1 |
| Δrad52/pYNRAD10 | 5 | 97 | 777 | 1.25 | 1.54 |
| Δrad52/pYNRAD54 | 5 | 388 | 792 | 4.89 | 6.04 |
| Δrad52/pYNREC2 | 5 | 12 | 678 | 0.18 | 0.22 |
| Δrad52/pYNXRS2 | 5 | 56 | 609 | 0.92 | 1.06 |
| wild type/pYN132 | 5 | 465 | 129 | 3.6 | 1 |
| Δmre11/pYN132 | 0 | 0 | 302 | 0 | N/A |
| Δmre11/pYN132 | 5 | | | | |
| Δmre11/pYNRAD10 | 5 | 184 | 41 | 4.49 | 1.25 |
| Δmre11/pYNRAD54 | 5 | 12 | 17 | 0.71 | 0.20 |
| Δmre11/pYNREC2 | 5 | 83 | 30 | 2.77 | 0.77 |
| Δmre11/pYNXRS2 | 5 | 9 | 14 | 0.64 | 0.18 |

*All strains also contain pAURHyg(ins)eGFP as the target for correction. All yeast strains are wild type except for a single mutation in the indicated DNA repair protein and contain plasmids expressing wildtype DNA repair proteins as indicated. The mutations used in these experiments are generally knock-out mutations.

TABLE 14

GENE REPAIR OF CHROMOSOMAL MUTATIONS IN WILD-TYPE *SACCHAROMYCES CEREVISIAE*

| Amount of Oligonucleotide (μg) | Correcting Oligonucleotide Tested | | Fold Difference in Correction Efficiency |
|---|---|---|---|
| | HygE3T/74 | HygE3T/74NT | |
| Repair of integrated pAUR101-HYG(rep)GFP | | | |
| 0 | 0* | 0 | 0x |
| 2.5 | 652 (140) | 3,108 (180) | 3.7x |
| 5.0 | 1,060 (120) | 4,203 (139) | 3.4x |
| 7.5 | 2,052 (112) | 6,120 (116) | 2.8x |
| 10.0 | 2,012 (121) | 3,932 (155) | 1.5x |

*Average colony count on hygromycin plates from three experiments is shown. Numbers in parentheses indicate the number of aureobasidin-resistant colonies (/$10^5$).

TABLE 15

NUCLEIC ACID SEQUENCE ALTERATION IN YEAST STRAINS WITH INCREASED LEVELS OF DNA REPAIR PROTEINS

| Yeast Strain* | Hyg3S/ 74NT (μg) | Hyg$^r$ | Aur$^r$ (10$^4$) | Correction efficiency (1/10$^5$) | Fold |
|---|---|---|---|---|---|
| Δpms1/pYN132 | 5 | 11 | 120 | 9.17 | 1x |
| Δpms1/pYNRAD51 | 5 | 11,890 | 578 | 2057 | 224x |
| Δpms1/pYNRAD52 | 5 | 53 | 241 | 22 | 2.4x |
| Δpms1/pYNRAD54 | 5 | 252 | 740 | 34 | 3.7x |
| Δpms1/pYNRAD55 | 5 | 255 | 593 | 43 | 4.7x |
| Δpms1/pYNMRE11 | 5 | 126 | 247 | 51 | 5.6x |
| Δpms1/pYNPMS1 | 5 | 64 | 256 | 25 | 2.7x |
| Δpms1/pYNXRS2 | 5 | 141 | 359 | 39 | 4.3x |
| Δpms1/pYNRAD10 | 5 | 17 | 809 | 2.1 | 0.23x |
| Δpms1/pYNRAD51 + pYNRAD54 | 5 | 641 | 774 | 83 | 9.1x |

*All strains also contain pAURHyg(rep)eGFP as the target for correction. All yeast strains are wild type except for a single mutation in the indicated DNA repair protein and contain plasmids expressing wild-type DNA repair proteins as indicated. The mutations used in these experiments are generally knockout mutations.

TABLE 16

CHROMOSOMAL NUCLEIC ACID SEQUENCE ALTERATION IN YEAST STRAINS WITH INCREASED LEVELS OF DNA REPAIR PROTEINS

| Plasmid in Yeast Strain* | Hyg3S/ 74NT (μg) | Hyg$^r$ | Aur$^r$ (10$^4$) | Correction efficiency (1/10$^5$) | Fold |
|---|---|---|---|---|---|
| pYN132 | 5 | 2,743 | 519 | 5.28 | 1x |
| pYNRAD51 | 5 | 14,412 | 389 | 37.04 | 7.01x |
| pYNRAD52 | 5 | 2,579 | 531 | 4.86 | 0.92x |
| pYNRAD54 | 5 | 15,028 | 402 | 37.38 | 7.08x |
| pYNRAD51 + pYNRAD54 | 5 | 2,961 | 326 | 9.08 | 1.72x |
| pYNRAD51 + pYNRAD52 | 5 | 2,578 | 359 | 7.18 | 1.36x |
| pYNMRE11 | 5 | 9,451 | 452 | 20.91 | 3.96x |
| pYNXRS2 | 5 | 7,120 | 290 | 24.55 | 4.65x |
| pYNMRE11 + pYNXRS2 | 5 | 23,669 | 409 | 57.87 | 10.96x |

*All strains contain an integrated pAUR101-HYG(rep)eGFP as the target for correction. All yeast strains are wild type except for the integrated plasmid and contain plasmids expressing wild-type DNA repair proteins as indicated.

EXAMPLE 3

Cultured Cell Manipulation

Mononuclear cells are isolated from human umbilical cord blood, bone marrow or peripheral blood of normal donors using Ficoll Paque Plus (Amersham Biosciences, Piscataway, N.J.) density centrifugation. CD34$^+$ cells are immunomagnetically purified from mononuclear cells using either the progenitor or Multisort Kits (Miltenyi Biotec, Auburn, Calif.). Lin-CD38$^+$ cells are purified from the mononuclear cells using negative selection with StemSep system according to the manufacturer's protocol (Stem Cell Technologies, Vancouver, Calif.). Cells used for microinjection are either freshly isolated or cryopreserved and cultured in Stem Medium (S Medium) for 2 to 5 days prior to microinjection. S Medium contains Iscoves' Modified Dulbecco's Medium without phenol red (IMDM) with 100 μg/ml glutamine/penicillin/streptomycin, 50 mg/ml bovine serum albumin, 50 μg/ml bovine pancreatic insulin, 1 mg/ml human transferrin, and IMDM; Stem Cell Technologies), 40 μg/ml low-density lipoprotein (LDL; Sigma, St. Louis, Mo.), 50 mM HEPEs buffer and 50 μM 2-mercaptoethanol, 20 ng/ml each of thrombopoietin, flt-3 ligand, stem cell factor and human IL-6 (Pepro Tech Inc., Rocky Hill, N.J.). After microinjection, cells are detached and transferred in bulk into wells of 48 well plates for culturing.

35 mm dishes are coated overnight at 4° C. with 50 μg/ml Fibronectin (FN) fragment CH-296 (Retronectin; TaKaRa Biomedicals, PanVera®, Madison, Wis.) in phosphate buffered saline and washed with IMDM containing glutamine/penicillin/streptomycin. 300 to 2000 cells are added to cloning rings and attached to the plates for 45 minutes at 37° C. prior to microinjection. After incubation, cloning rings are removed and 2 ml of S Medium are added to each dish for microinjection. Pulled injection needles with a range of 0.22 μ to 0.3 μ outer tip diameter are used. Cells are visualized with a microscope equipped with a temperature controlled stage set at 37° C. and injected using an electronically interfaced Eppendorf Micromanipulator and Transjector. Successfully injected cells are intact, alive and remain attached to the plate post injection. Molecules that are fluorescently labeled allow determination of the amount of oligonucleotide delivered to the cells.

For in vitro erythropoiesis from Lin$^-$CD38$^-$ cells, the procedure of Malik can be used (Malik et al., Blood 91:2664-71 (1998)). Cells are cultured in ME Medium for 4 days and then cultured in E Medium for 3 weeks. Erythropoiesis is evident by glycophorin A expression as well as the presence of red color representing the presence of hemoglobin in the cultured cells. The injected cells are able to retain their proliferative capacity and the ability to generate myeloid and erythoid progeny. CD34$^+$ cells can convert a normal A (PA) to sickle T (β$^S$) mutation in the β-globin gene or can be altered using any of the oligonucleotides of the invention herein for correction or alteration of a normal gene to a mutant gene. Alternatively, stem cells can be isolated from blood of humans having genetic disease mutations and the oligonucleotides of the invention can be used to correct a defect or to modify genomes within those cells.

Alternatively, non-stem cell populations of cultured cells can be manipulated using any method known to those of skill in the art including, for example, the use of polycations, cationic lipids, liposomes, polyethylenimine (PEI), electroporation, biolistics, calcium phosphate precipitation, or any other method known in the art.

EXAMPLE 4

Treatment Of Blood Disorders

The kits and methods of the invention can be used, for example, in therapeutic approaches when the target cell is a stem cell. These approaches can be used with a variety of pluripotent stem cells, including, for example, any of the stem cell lines in the National Institutes of Health list which are described elsewhere herein, embryonic stem cells, and hematopoietic stem cells. Such an approach with any of these cell types is particularly advantageous because the target cell can be manipulated ex vivo allowing for correction of the mutation and selection of a clone with the desired alteration. The cells are then reintroduced into the patient resulting in repopulation in whole or in part with progeny from the genetically corrected stem cell. For hematopoietic stem cells, the cells may be reintroduced after the patient's bone marrow has been ablated, although complete eradication of host hematopoiesis is not required to achieve therapeutic effects (see, e.g., Blau, *Baillieres Clin. Haematol* 11:257-275 (1998)). Many diseases of blood, such as sickle cell anemia, thallassemias, immunological and clotting disorders, can be treated using the compositions and methods of the invention to correct mutations into the chromosomal DNA of hematopoietic stem cells and transplanting these cells into a patient.

Most therapeutic approaches on stem cells use viral vectors, e.g. retroviral vectors, portions of adenovirus (Ad) or adeno-associated virus (AAV), to deliver nucleic acid sequences encoding partial or complete portions of a particular protein. The protein is expressed in the cell which results in the desired phenotype. See, for example, U.S. Pat. Nos. 5,700,470 and 5,139,941. The use of such transgene vectors in any eukaryotic organism adds one or more exogenous copies of a gene, which.gene may be foreign to the host, in a usually random fashion at one or more integration sites of the organism's genome at some frequency. The gene which was originally present in the genome, which may be a normal allelic variant, mutated, defective, and/or functional, is retained in the genome of the host. In contrast, the methods of the inventions described herein produce a legacy-free, precise nucleic acid sequence alteration of the target DNA and lack the immune response produced in viral vector gene therapy.

Treatment of sickle cell disease. As a model for the correction of mutations in stem cells using the kits and methods of the invention, we test their ability to correct the hemoglobin sickle mutation in human cells obtained from blood, bone marrow, umbilical cord blood or other sources of human hematopoietic stem cells. Alternatively, we test the ability to correct the hemoglobin sickle mutation in cultured cells or in mouse models. Numerous transgenic mouse strains have been developed which exclusively express human globins, including the sickle allele. Mice that exclusively express human sickle hemoglobin exhibit significant sickle pathology which is sufficiently faithful to test antisickling treatments regimens. See, for example, Blouin et al., Blood 94:1451-1459 (1999) and Fabry et al., Blood 97:410-418 (2001). In addition, methods for purifying and culturing hematopoietic stem cells are well known to one of ordinary skill in the art. See, for example, Spangrude et al., Science 214:58-62 (1988) and United States Patent 6,261,841.

We purify hematopoietic stem cells from mice, correct the sickle allele, reintroduce into mice and monitor sickling phenotype.

Treatment of AIDS. Entry of HIV-1 into target cells is known to require cell surface CD4 as well as additional host cell cofactors. The principal cofactor for entry mediated by the envelope glycoproteins of primary macrophage-tropic strains of HIV-1 is CC-CKR5. See, for example, U.S. Pat. No. 6,057,102. Individuals who are homozygous for a mutation of the CKR-5 receptor which results in complete suppression of CKR-5 expression are resistant to HIV infection. An individual who is heterozygous for a CKR-5 mutation may be more resistant to HIV infection and an individual who is homozygous for a CKR-5 mutation may be more resistant than heterozygous individuals.

The sequence of the human CKR-5 gene is known and there are no apparent adverse effects resulting from a mutation in CKR-5. Accordingly, individuals infected with HIV-1 can be treated by removing hematopoietic stem cells and introducing a mutation in the CKR-5.

EXAMPLE 5

Treatment of Human Blood Cells with HDAC Inhibitors Increases Nucleic Acid Sequence Alteration Efficiency Mononuclear cells are isolated from human umbilical cord blood of normal donors using Ficoll Paque Plus (Amersham Biosciences, Piscataway, N.J.) density centrifugation. $CD34^+$ cells are immunomagnetically purified from mononuclear cells using either the progenitor or Multisort Kits (Miltenyi Biotec, Auburn, Calif.). $Lin^-CD38^-$ cells are purified from the mononuclear cells using negative selection with StemSep system according to the manufacturer's protocol (Stem Cell Technologies, Vancouver, Calif.). Cells used for microinjection or electroporation or liposomal transfection with the oligonucleotides of the invention are either freshly isolated or cryopreserved and cultured in Stem Medium (S Medium) for 2 to 5 days prior to treatment. S Medium contains Iscoves' Modified Dulbecco's Medium without phenol red (IMDM) with 100 µg/ml glutamine/penicillin/streptomycin, 50 µg/ml bovine pancreatic insulin, 1 mg/ml human transferrin, and IMDM, 40 µg/ml low-density lipoprotein (LDL; Sigma, St. Louis, Mo.), 50 mM HEPEs buffer and 50 µM 2-mercaptoethanol, 20 ng/ml each of thrombopoietin, flt-3 ligand, kit ligand, and may contain 50 mg/ml fetal bovine serum albumin, stem cell factor and human IL-6 (Pepro Tech Inc., Rocky Hill, N.J.). One source of serum-free medium is QBSF60 from Quality Biological in Gaithersburg, Md. Cells are cultured in medium containing 170 µM trichostatin A for the 16 hours immediately prior to treatment with the oligonucleotide of the invention. After treatment, cells are detached and transferred in bulk into wells of 48 well plates for culturing.

For microinjection, 35 mm dishes are coated overnight at 4° C. with 50 µg/ml Fibronectin (FN) fragment CH-296 (Retronectin; TaKaRa Biomedicals, PanVera®, Madison, Wis.) in phosphate buffered saline and washed with IMDM containing glutamine/penicillin/streptomycin. 300 to 2000 cells are added to cloning rings and attached to the plates for 45 minutes at 37° C. prior to microinjection. After incubation, cloning rings are removed and 2 ml of S Medium are added to each dish for microinjection. Pulled injection needles with a range of 0.22 µ to 0.3 µ outer tip diameter are used. Cells are visualized with a microscope equipped with a temperature controlled stage set at 37° C. and injected using an electronically interfaced Eppendorf Micromanipulator and Transjector. Successfully injected cells are intact, alive and remain attached to the plate post injection. Molecules that are fluorescently labeled allow determination of the amount of oligonucleotide delivered to the cells.

For electroporation, approximately $2-4 \times 10^6$ cells in 250 µl of serum-free medium containing TPO (50 ng/ml), Kit Ligand and FLT3 ligand (100 ng/ml) that have been cultured for 72 hours in the presence of the same cytokines are electroporated in an electroporation apparatus such as the Square Wave apparatus by VTX. Cells are electroporated with about 25-30 µg of oligonucleotide at 220 mV and 960 µF for one pulse. After electroporation, cells are diluted to 2.5 x 105 cells/ml in Iscove's medium containing 10% FCS and TPO (50 ng/ml), Kit Ligand and FLT3 ligand (100 ng/ml) and analyzed by flow cytome try. Cells are allowed to recover for about 12 hours following treatment and dead cells are removed. Cells are then maintained in culture. Frequencies of nucleic acid sequence alteration are determined on cell samples at various times using, e.g., sequencing of PCR samples of cellular DNA, to determine nucleic acid sequence alteration efficiencies. Nucleic acid sequence alteration of hematopoietic stem cells is indicated by nucleic acid sequence alteration in cell populations maintained for at least four weeks after electroporation. It is expected that mature cells will die over time leaving a population of immature cells capable of differentiation.

For in vitro erythropoiesis from Lin⁻CD38⁻ cells, the procedure of Malik, 1998 can be used. Cells are cultured in ME Medium for 4 days and then cultured in E Medium for 3 weeks. Erythropoiesis is evident by glycophorin A expression as well as the presence of red color representing the presence of hemoglobin in the cultured cells. The injected cells are able to retain their proliferative capacity and the ability to generate myeloid and erythoid progeny. CD34⁺ cells can convert a normal A ($\beta^A$) to sickle T ($\beta^S$) mutation in the β-globin gene or can be altered using any of the oligonucleotides of the invention herein for correction or alteration of a normal gene to a mutant gene. Alternatively, stem cells can be isolated from blood of humans having genetic disease mutations and the oligonucleotides of the invention can be used to correct a defect or to modify genomes within those cells.

Alternatively, non-stem cell populations of cultured cells can be manipulated using any method known to those of skill in the art including, for example, the use of polycations, cationic lipids, liposomes, polyethylenimine (PEI), electroporation, biolistics, calcium phosphate precipitation, or any other method known in the art.

EXAMPLE 6

Treatment with Trichostatin a Influences the Ability to Direct Nucleic Acid Sequence Alteration in Yeast Cells In this example, trichostatin A is used to enhance the efficiency of oligonucleotide-mediated nucleic acid sequence alteration in a system employing single-stranded oligonucleotides with modified backbones. We perform these experiments using an episomal target, such as pAURHYG(x)eGFP (FIG. 2), or an integrated copy of the same target to monitor chromosomal gene alteration. These assay systems are described in Example 2.

As described in Example 2, both the episomal and integrational plasmids also contain an aureobasidinA resistance gene. For example, in pAURHYG(rep)GFP, hygromycin resistance gene function and green fluorescence from the eGFP protein are restored when a G at position 137, at codon 46 of the hygromycin B coding sequence, is converted to a C thus removing a premature stop codon in the hygromycin resistance gene coding region.

We use this system to assay the ability of three oligonucleotides (shown in FIG. 3) to support correction under a variety of conditions both with and without an HDAC inhibitor, such as trichostatin A. Oligonucleotide Hyg74T (HygE3T/74T) is a 74-base oligonucleotide with the base targeted for alteration centrally positioned. The second oligonucleotide, designated Hyg74NT (HygE3T/74NT), is the complement of Hyg74T. The third oligonucleotide, designated Hyg10, is a 24 base oligonucleotide with the base targeted for alteration centrally positioned. The sequences of the oligonucleotides are shown in FIG. 3. Hyg74T and Hyg74NT are single-stranded DNA oligonucleotides with three phosphorothioate linkages at each end. Hyg10 has one LNA on each end. A non-specific, control oligonucleotide that is not complementary to the target sequence may be used as a control. Alternatively, an oligonucleotide of identical sequence but lacking a mismatch to the target or a completely thioate modified oligonucleotide or a completely 2'-O-methylated modified oligonucleotide may be used as a control.

Oligonucleotide synthesis and cells. We synthesize and purify single-stranded oligonucleotides (including those with the indicated modifications) as described in Example 2. Plasmids used for assay are maintained stably in yeast (Saccharomyces cerevisiae) strain LSY678 MATa at low copy number under aureobasidin selection. Plasmids and oligonucleotides are introduced into yeast cells by electroporation as follows: to prepare electrocompetent yeast cells, we inoculate 10 ml of YPD media from a single colony and grow the cultures overnight with shaking at 300 rpm at 30° C. We then add 30 ml of fresh YPD media, with or without 50 µg/mL trichostatin A, to the overnight cultures and continue shaking at 30° C. until the OD600 is approximately 0.5 (4 hours). We then wash the cells by centrifuging at 4° C. at 3000 rpm for 5 minutes and twice resuspending the cells in 25 ml ice-cold distilled water. We then centrifuge at 4° C. at 3000 rpm for 5 minutes and resuspend in 1 ml ice-cold 1 M sorbitol and then finally centrifuge the cells at 4° C at 5000 rpm for 5 minutes and resuspend the cells in 120 µl M sorbitol.

To transform electrocompetent cells with plasmids or oligonucleotides, we mix 40 µl of cells with 5 µg of nucleic acid, unless otherwise stated, and incubate on ice for 5 minutes. We then transfer the mixture to a 0.2 cm electroporation cuvette and electroporate with a BIO-RAD Gene Pulser apparatus at 1.5 kV, 25 µF, 200 Ω for one five-second pulse. We then immediately resuspend the cells in 1 ml YPD supplemented with 1M sorbitol and with or without 50 µg/mL a trichostatin, such as trichostatin A, and incubate the cultures at 30° C. with shaking at 300 rpm for 6 hr. We then spread 200 µl of this culture on selective plates containing 300 µg/ml hygromycin and spread 200 µl of a $10^5$ dilution of this culture on selective plates containing 500 ng/ml aureobasidinA and incubate at 30° C. for 3 days to allow individual yeast colonies to grow. We then count the colonies on the plates and calculate the gene conversion efficiency by determining the number of hygromycin resistance colonies per $10^5$ aureobasidinA resistant colonies. We also test other HDAC inhibitors using this assay system.

Trichostatin A increases the efficiency of oligonucleotide-mediated gene alteration. We compare the efficiency of oligonucleotide-mediated gene alteration in cells pre-treated with 50 µg/mL trichostatin A with the efficiency of oligonucleotide-mediated gene alteration in cells without pre-treatment. See, for example, Table 17. These experiments indicate that growth of cells in 50 µg/mL trichostatin A for four hours prior to electroporation increases the efficiency of gene alteration up to several-fold and that treatment of cells with 50 µg/mL trichostatin A during the recovery period can also increase the efficiency of gene alteration up to 3 or more fold.

TABLE 17

EFFECT OF TRICHOSTATIN TREATMENT DURING RECOVERY ON CELL CONVERSION

| Treatment | Oligonucleotide | Hyg$^r$ | Aur$^r$ ($10^4$) | Correction efficiency ($1/10^5$) |
|---|---|---|---|---|
| No treatment | 5 µg Hyg74NT | | | 1.08 |
| | 5 µg Hyg74T | | | 0.16 |
| Cells pre-treated with 50 µg/mL trichostatin A | 5 µg Hyg74NT | 42 | 466 | 0.9 |
| | 5 µg Hyg74T | 278 | 844 | 3.3 |

TABLE 17-continued

EFFECT OF TRICHOSTATIN TREATMENT DURING RECOVERY ON CELL CONVERSION

| Treatment | Oligonucleotide | Hyg$^r$ | Aur$^r$ ($10^4$) | Correction efficiency ($1/10^5$) |
|---|---|---|---|---|
| Cells treated during recovery with 50 μg/mL trichostatin A | 5 μg Hyg74NT | | | 2.31 |
| | 5 μg Hyg74T | | | 0.34 |
| Cells both pre-treated and treated during recovery with 50 μg/mL trichostatin A | 5 μg Hyg74NT | 235 | 734 | 3.2 |
| | 5 μg Hyg74T | 230 | 1120 | 2.05 |

Time and temperature dependence of trichostatin A treatment on targeting with Hyg10. We compare the effect of time during the recovery period and temperature of the centrifugation step on the efficiency of oligonucleotide-mediated gene alteration in cells pre-treated with 50 μg/mL trichostatin A. See, for example, Table 18. An overnight culture of yeast cells is diluted into 200 mL YPD with or without 50 μg/mL trichostatin A and grown with shaking at 30° C. until the OD600 is approximately 0.5 (4 hours) as above. We then wash the cells by centrifuging at either 4° C. or room temperature at 3000 rpm for 5 minutes and resuspending the cells in 100 mls prewarmed, fresh YPD media. The cells are then allowed to grow for 20 or 40 minutes and prepared and electroporated with 1.62 μg of the Hyg10 oligonucleotide, as described above. The cells are allowed to recover and plated as described above and we determine the conversion per $10^5$ cells.

TABLE 18

EFFECT OF TIME OF RECOVERY, TEMPERATURE OF CENTRIFUGATION, AND PRETREATMENT WITH TRICHOSTATIN ON CELL CONVERSION

| | Conversion per $10^5$ cells | | | |
|---|---|---|---|---|
| Oligonucleotide and trichostatin A pre-treatment | centrifugation at 4° C., 20 minutes growth after resuspending | centrifugation at 4° C., 40 minutes growth after resuspending | centrifugation at room temperature, 20 minutes growth after resuspending | centrifugation at room temperature, 40 minutes growth after resuspending |
| 1.62 μg Hyg10 + 50 μg/mL trichostatin A | 8.1 | 14.8 | 6.6 | 13.5 |
| 1.62 μg Hyg10 | 3.8 | 8.6 | 3.8 | 7.6 |

EXAMPLE 7

Lambda Phage Beta Protein Increases the Efficiency of Targeted Sequence Alteration in Yeast The effect of expression of beta protein on the efficiency of gene correction by modified single-stranded gene repair targeting vectors in Saccharomyces cerevisiae is studied.

The CYC1 gene in yeast is chosen as an experimental system in which to study gene repair and the effect of beta protein on gene repair efficiency. The diploid yeast strain YMH51 contains a wild-type copy of CYC1 and diploid yeast strains YMH52, YMH53, YMH54 and YMH55 contain a mutated version of the CYC1 gene in hemizygous state. These strains are derived from the yeast strain MATα cyc1-706::CYH2 cyc7-67 ura3-52 leu2-3 112 cyh2. In YMH51, codon 22 of CYC1 is the wild-type TGC (Cys) sequence; in YMH52, codon 22 is CGC (Arg); in YMH53, codon 22 is AGC (Ser); in YMH54, codon 22 is GGC (Gly); and in YMH55, codon 22 is TCC (Ser). In each case, the gene product of the mutated gene possesses a different amino acid in place of a cysteine residue at position 22 of the primary sequence. The phenotype associated with this mutation is inability to grow using glycerol as the sole carbon source. Reversion of the CYC1 gene mutation to the wild-type sequence, e.g., as mediated by a sequence altering oligonucleotide, confers upon the yeast the ability to grow on glycerol only.

Cyc1/70T (70T) and Cyc1/70NT (70NT) are modified single-stranded gene repair targeting vectors used in these experiments. The 70T vector is complementary to, and therefore targets, the transcribed strand of the mutant CYC1 gene, whereas the 70NT vector is complementary to, and therefore targets, the nontranscribed strand. The targeting vectors contain wild-type sequence, such that there exists a single base mismatch between the targeting vectors and mutated CYC1 gene sequence. Both 70T and 70NT vectors contain three phosphorothioated linkages at each of their 5' and 3' termini (indicated by the "*" symbols in Table 19, below). The vector called Hyg3S/74T (74T) serves as a negative control and is not complementary to the sequence of either strand of the CYC1 gene. The sequence of these vectors appears as follows in Table 19. All the oligonucleotide vectors are synthesized and purified according to standard techniques in the art, or as discussed elsewhere in this specification.

TABLE 19

Cyc1/70T

SEQ ID NO.:21
5'-A* G*G*T GCT ACA CTT TTC AAG ACT AGA TGT CTA CAA TGC CAC ACC GTG GAA AAG GGT GGC CCA CAT AAG* G*T*T-3'

Cyc1/70NT

SEQ ID NO.:22
5'-A*A*C* CTT ATG TGG GCC ACC CTT TTC CAC GGT GTG GCA TTG TAG ACA TCT AGT CTT GAA AAG TGT AGC A*C*C* T-3'

TABLE 19-continued

Hyg3ST/74T

SEQ ID NO.:8
5'-C*T*C* GTG CTT TCA GCT TCG ATG TAG GAG GGC GTG
GAT ACG TCC TGC GGG TAA ATA GCT GCG CCG ATG GTT TC
*T*A*C-3'

Five micrograms of each CYC1 oligonucleotide are electroporated into a yeast strain with a mutation in the CYC1 gene, such as YMH52, YMH53, YMH54 and YMH55, and the YMH51 diploid wild-type strain according to methods well known to the skilled artisan. Selection for nucleic acid sequence alteration is carried out by spreading 1 ml of yeast cells, without dilution, on YPG plates (1% yeast extract, 2% peptone, 3% glycerol, 2% agar). Growth without selection is analyzed by spreading a separate 0.1 ml of yeast cells, diluted $1\times10^{-4}$, on YPD plates, which contain dextrose rather than glycerol as the carbon source. YPG plates are incubated at 30° C. for 7 days and YPD plates are incubated at 30° C. for 3 days. Colony counts of selected (grown on YPG) and nonselected yeast (grown on YPD) are determined using an Accu-Count™ 1000 (BioLogics, Inc.). Correction efficiency (C.E.) is calculated by dividing the number of YPG colonies by the number of YPD colonies; this value normalizes for variability in transformation frequency and survival. Presence of the wild-type CYC1 gene sequence in YMH52, YMH53, YMH54 or YMH55 yeast selected on YPG plates is confirmed by PCR amplification of the exon of the CYC1 gene containing codon 22 and then sequencing the gene product. Selected colonies are picked at random from a YPG plate and diluted in 50 µl of distilled water. One microliter of yeast cell solution is added to a PCR reaction mixture containing 1×PCR amplification buffer, 300µM dNTP, OJW-24 primer, ORB-27 primer, and Taq polymerase. Sequences for the OJW-24 primer and the ORB-27 primer may be found, for example, in Hampsey, "A tester system for detecting each of the six base-pair substitutions in *Saccharomyces cerevisiae* by selecting for an essential cysteine in iso-1-cytochrome c," Genetics 128: 59-67 (1991). Samples are preheated at 92° C. for 4 min., followed by 35 cycles of 92° C. for 10 sec., 52° C. for 30 sec., 60° C. for 1 min., with a final single elongation step of 68° C for 8 min., followed by incubation at 4° C. PCR products are analyzed by gel electrophoresis through a 1% agarose gel to confirm the presence of the 422 basepair CYC1 exon band. The sequence of PCR products is confirmed by automated sequencing using an ABI 373 Sequencer.

Results from these types of experiments are presented below in Table 20. The wild-type strain YMH51 grows well on YPG plates because the-wild type CYC1 gene is capable of metabolizing glycerol. In contrast, the mutant strains, containing a hemizygous mutated CYC1 gene, are unable to grow on YPG plates when electroporated with the negative control 74T vector which does not target the CYC1 gene. Electroporation of the mutant strains with either oligonucleotide, 70T or 70NT, results in reversion of the mutated version of the CYC1 gene to the wild-type sequence, as evidenced by the ability of treated cells to grow into colonies on YPG plates. The frequency of gene repair is much higher for 70NT, the vector that binds to and targets the non-template strand of the CYC1 gene, as compared to 70T.

TABLE 20

| Yeast Strain | Oligonucleotide | No. of YPD Plate Colonies × $10^{-4}$ | No. of YPG Plate Colonies | C.E. (×$10^{-4}$) | Mismatch |
|---|---|---|---|---|---|
| YMH51 | Cyc1/70NT | 1339 | lawn | — | none |
| YMH51 | Cyc1/70T | 1085 | lawn | — | none |
| YMH52 | Cyc1/70NT | 836 | 186 | 0.47 | G/T |
| YMH52 | Cyc1/70T | 845 | 57 | 0.17 | C/A |
| YMH53 | Cyc1/70NT | 722 | 73 | 0.21 | T/T |
| YMH53 | Cyc1/70T | 771 | 281 | 0.74 | A/A |
| YMH54 | Cyc1/70NT | 702 | 80 | 0.28 | C/T |
| YMH54 | Cyc1/70T | 715 | 43 | 0.14 | G/A |
| YMH55 | Cyc1/70NT | 616 | 895 | 2.99 | G/G |
| YMH55 | Cyc1/70T | 629 | 116 | 0.38 | C/C |
| YMH55 | Hyg3S/74T | 739 | 0 | 0 | nonspecific |

The expression of beta protein and other proteins in the RAD52 epistasis group, the mismatch repair group, or the nucleotide excision repair group are then tested for their effect on efficiency of gene repair of the CYC1 gene in yeast. We construct vectors overexpressing genes in the RAD52 epistasis group, the mismatch repair group, or the nucleotide excision repair group as described elsewhere herein. We construct a yeast beta expression vector as follows. Coding sequence for the beta protein is amplified by PCR from a plasmid containing the gene, after which the PCR product is digested with HindIII and XhoI restriction enzymes, and ligated into the yeast expression vector pYN132, which contains the constitutively active yeast promoter TPI. A sample of the ligation reaction is used to transform DH10B cells after which transformed cells are selected and positive colonies are analyzed for the presence of the expression construct, called pYNTβ, using standard techniques familiar to the skilled artisan. YMH51, YMH52, YMH53, YMH54 and YMH55 cells are electroporated with 5 µg of the pYNTβ construct or a plasmid overexpressing a gene from the RAD52 epistasis group, the mismatch repair group, or the nucleotide excision repair group, or pYN132 (as a negative control), after which transformed cells are selected by growth on SC URA3⁻ plates (minimal media lacking uracil and supplemented with all amino acids) for 3 days. These yeast strains containing these plasmid constructs are electroporated with 5 µg of the 70NT oligonucleotide and gene repair activity is assessed by testing colony growth on YPG and YPD plates, as described above.

The results from such an experiment with YMH55 are shown below in Table 21. YMH55 yeast grow in the presence of glycerol indicating that gene repair is effected, although the growth of the yeast containing the empty pYN132 vector (negative control) is much diminished compared to YMH55 lacking pYN132 (see Table 20, above), an effect that may be attributable to double selection in glycerol and growth medium lacking uracil. Surprisingly, however, despite the inhibitory effects of double selection, expression in the YMH55 strain of beta protein, or a protein from RAD52 epistasis group, the mismatch repair group, or the nucleotide excision repair group as indicated in Table 21, substantially increases the frequency of targeted gene repair of the mutated CYC1 gene by the 70NT oligonucleotide.

TABLE 21

| Over-expression construct | No. of YPD Plate Colonies | No. of YPG Plate Colonies | Average C.E. (×10$^{-5}$) | Fold | S.D. |
|---|---|---|---|---|---|
| pYN132 | 549 | 19 | 0.04 | 1 | +/−0.25 |
| PYNRAD51 | 500 | 260 | 0.52 | 14.8 | +/−5.13 |
| PYNRAD52 | 484 | 108 | 0.22 | 6.2 | +/−3.61 |
| PYNRAD54 | 482 | 42 | 0.09 | 2.4 | +/−0.80 |
| PYNRAD55 | 519 | 410 | 0.78 | 22.2 | +/−5.70 |
| PYNMRE11 | 627 | 25 | 0.04 | 1.1 | +/−0.69 |
| PYNXRS2 | 447 | 22 | 0.03 | 1.34 | +/−0.53 |
| pYNβ | 517 | 166 | 0.32 | 9.1 | +/−1.70 |

In other experiments examining the effect of beta protein expression on CYC1 gene repair, the correction efficiency per $10^5$ transformants is 0.326, corresponding to a 5 to 18 fold increase in gene repair efficiency.

The results from such an experiment with YMH53 overexpressing multiple proteins are shown below in Table 22. YMH53 yeast grow in the presence of glycerol indicating that gene repair is effected. Expression in the YMH53 strain of both the MRE11 and XRS2 proteins or both the RAD52 and RAD54 proteins, substantially increases the frequency of targeted gene repair of the mutated CYC1 gene by both the 70T and 70NT oligonucleotides.

TABLE 22

| Overexpression construct | No. of YPD Plate Colonies | No. of YPG Plate Colonies | Average C.E. (×10$^{-5}$) | Fold |
|---|---|---|---|---|
| Oligonucleotide cyc1/70T | | | | |
| pYN132 | | | 0.03169 | 1 |
| PYNMRE11 + PYNXRS2 | 590 | 155 | .263 | 8.29 |
| PYNRAD52 + PYNRAD54 | 558 | 103 | .185 | 5.82 |
| Oligonucleotide cyc1/70NT | | | | |
| pYN132 | | | 0.0056 | 1 |
| PYNMRE11 + PYNXRS2 | 553 | 178 | 0.322 | 57.48 |
| PYNRAD52 + PYNRAD54 | 608 | 109 | 0.179 | 32.01 |

EXAMPLE 8

Hydroxyurea Enhances Targeted Sequence Alteration in Yeast Cells

In this example, HU is used to enhance the efficiency of gene repair in a system employing single-stranded oligonucleotides with modified backbones to measure gene repair using plasmid pAURHYG(rep)eGFP, with plasmid pAURHYG(wt)eGFP as a control, as described in Example 2. We use this system to assay the ability of three oligonucleotides (shown in FIG. 3) to support correction under a variety of conditions. Oligonucleotides HygE3T/74 and HygE3T/74NT, and control oligonucleotides, are described in Example 2. The third oligonucleotide, designated Hyg10, is a 24 base oligonucleotide with the base targeted for alteration centrally positioned, with the sequence 5'-ACC CGC AGG ACG TAT CCA CGC CCT-3'(SEQ ID NO: 20). The Hyg10 oligonucleotide has one LNA modification on each end. Oligonucleotides are synthesized as described in Example 2.

Plasmids used for assay are maintained stably in yeast (Saccharomyces cerevisiae) strain LSY678 MATa at low copy number under aureobasidin selection. Plasmids and oligonucleotides are introduced into yeast cells by electroporation as follows: to prepare electrocompetent yeast cells, we inoculate 10 ml of YPD media from a single colony and grow the cultures overnight with shaking at 300 rpm at 30° C. We then add 30 ml of fresh YPD media, with or without 20 mM HU, to the overnight cultures and continue shaking at 30 C until the OD$_{600}$ is approximately 0.5 (4 hours). We then wash the cells by centrifuging at 4° C. at 3000 rpm for 5 minutes and resuspending the cells in fresh YPD media. We then take time points, removing 40 ml of culture at 10, 20, 40, 60, and 90 minutes after resuspension. To transform electrocompetent cells with plasmids or oligonucleotides, we mix 40 µl of cells with 5 µg of nucleic acid, unless otherwise stated, and incubate on ice for 5 minutes. Electroporation and determination of the alteration ("conversion") efficiency are performed as in Example 2.

Hydroxyurea increases the efficiency of oligonucleotide-mediated nucleic acid sequence alteration. We compare the efficiency of oligonucleotide-mediated nucleic acid sequence alteration in cells pre-treated with 20 mM HU with the efficiency of oligonucleotide-mediated nucleic acid sequence alteration in cells without pre-treatment. These experiments, presented in Table 23, indicate that growth of cells in 20 mM HU for four hours prior to electroporation can increase the efficiency of nucleic acid sequence alteration at least 25- to 40-fold. As shown in Table 23, although we observe the greatest increase in efficiency of nucleic acid sequence alteration when the post-HU outgrowth period is 90 minutes, HU treatment enhances the efficiency of nucleic acid sequence alteration at 10, 20, 40 and 60 minutes also. Table 23 shows that HU pre-treatment enhances nucleic acid sequence alteration efficiency for all oligonucleotides tested, whether they target the sense (nontranscribed) strand (HygE3T/74NT; SEQ ID NO: 9) or the transcribed strand (HygE3T/74T; SEQ ID NO: 8), and whether the oligonucleotides are 74 bases long (HygE3T/74NT) or 24 bases long (Hyg10; SEQ ID NO: 20).

TABLE 23

Hydroxyurea increases the efficiency of oligonucleotide-mediated gene repair.

| [Hydroxyurea] | Growth Time (min) | OD$_{600}$ | Correction efficiency HygE3T/74NT | Correction efficiency HygE3T/74 | Correction efficiency Hyg10 |
|---|---|---|---|---|---|
| 0 | 10 | 0.57 | 0.56 | 0.15 | 0.57 |
| 0 | 20 | | 5.16 | 2.9 | 4.8 |
| 0 | 40 | | 8.6 | 3.4 | 8.02 |
| 0 | 60 | 0.73 | 3.5 | 2.32 | 4.2 |
| 0 | 90 | 0.81 | 2.6 | 0.56 | 2.6 |
| 20 mM | 10 | 0.51 | 6.7 | 3.1 | 35 |
| 20 mM | 20 | | 7.5 | 4.9 | 0.24 |
| 20 mM | 40 | | 20.7 | 9.5 | 3.6 |
| 20 mM | 60 | 0.64 | 10.1 | 7.8 | 24.6 |
| 20 mM | 90 | 0.75 | 67.8 | 22.4 | 26.3 |

Yeast cultures are grown for 4 hours in the presence or in the absence of 20 mM HU, as indicated. The cells are then washed, resuspended in fresh YPD medium, and grown for 10, 20, 40, 60 or 90 minutes, to the $OD_{600}$ indicated, prior to electroporation with 5 μg of oligonucleotide HygE3T/74NT or HygE3T/74, or 1.62 μg of Hyg10. The cells are then plated onto selective media containing hygromycin or aureobasidinA. The efficiency of gene correction is reported as "Correction efficiency," which represents the number of hygromycin resistant colonies observed per $10^5$ aureobasidinA resistant colonies.

EXAMPLE 9

Use of HU and TSA in Dual Targeting Experiments

The efficiency of targeted alteration can be increased and the cost decreased by using at least two unrelated oligonucleotides simultaneously in dual targeting experiments. In this approach, alteration by a first oligonucleotide confers a selectable phenotype that is selected for. Alterations directed by a second oligonucleotide are then screened for from within this selected population. See, e.g., commonly owned and copending United States patent application No. 60/416,983 "Methods And Compositions For Reducing Screening In Oligonucleotide-Directed Nucleic Acid Sequence Alteration," filed Oct. 7, 2002, which is hereby incorporated by reference in its entirety. Because the population identified by selective pressure is enriched for cells that bear an edited base at the non-selective site, the approach is useful as a method, termed gene editing, for rapidly and efficiently introducing a single nucleotide polymorphism of choice into virtually any gene at any desired location using modified single-stranded oligonucleotides.

The dual targeting strategy is illustrated in FIG. 9A. The LSY678lntHyg(rep)β strain (Table 24) contains a 240 kb human $β^S$-globin YAC and a cassette containing a chromosomal hygromycin-resistance gene inactivated by a single base mutation and a functional aureobasidin-resistance gene. See Liu et al., Nucleic Acids Res. 31:2742-2750 (2002); Parekh-Olmedo et al., Chem. Biol. 9:1073-1084 (2002); and Liu et al., Mol. Cell Biol. 22:3852-3863 (2002). FIG. 9B shows the oligonucleotide that is used to direct editing of the chromosomal hygromycin mutant gene. Hyg3S/74NT (SEQ ID NO: 9) is a 74-mer that is specific for binding to the nontranscribed strand and contains three terminal phosphorothioate linkages. Id. Also shown is the target sequence of the mutant, which contains a TAG stop codon. FIG. 9C illustrates the structure of the β-globin YAC and nucleotides targeted for editing are specified. The two nonselectable changes are directed by different oligonucleotides, βThal1 (SEQ ID NO: 27) and βThal2 (SEQ ID NO: 28), in separate experiments. The YAC contains approximately 230 kb of genomic DNA from human chromosome 11, indicated by the shaded region. The unshaded regions represent the yeast sequences that are on either end of the YAC (not drawn to scale). Yu et al., Proc. Natl. Acad. Sci. USA 97:5978-5983 (2000). A portion of the β-globin sequence is shown, beginning with the start codon. βThal1 directs a change from a G to an A while βThal2 directs a change from a T to a C. The sequences of the oligonucleotides having nucleic acid sequence alteration activity are shown and are designed to bind to the non-transcribed strand, relative to human transcription of the β-globin locus. Both changes result in single-base substitutions that have been documented to result in β-thalassemia in humans.

For editing experiments, YAC-containing LSY678IntHyg (rep)β cells (Table 24) are grown in the presence of HU, electroporated with the selectable and nonselectable oligonucleotides, and allowed to recover in the presence of TSA (FIG. 9A). Because the human β-globin gene is likely to be transcriptionally inactive in yeast, HU and TSA are especially important in increasing target accessibility. The results of dual targeting experiments are presented in FIG. 10A. Hygromycin-resistant colonies are observed when the oligonucleotide, Hyg3S/74NT, is used. The ratio of hygromycin-resistant colonies to aureobasidin-resistant colonies is referred to as the correction efficiency (C.E.). The presence of HU and TSA leads to an increase in the C.E. of the hygromycin mutation, here about 4- to 6-fold. In this experiment, hygromycin-resistant colonies are found at roughly 1 per 3000 aureobasidin-resistant colonies. Hygromycin-resistant colonies are then analyzed for second-site editing in the YAC β-globin gene. The βThal1 oligonucleotide is designed to direct the replacement of a G in TGG codon 16 of exon 1 with an A, giving the stop codon TGA (FIG. 9C). FIG. 10B shows an ABI SNaPshot (middle panels) and direct DNA sequence (bottom panel) of a region of the β-globin gene in a corrected colony from this experiment; in both, the G to A change is evident. Of those colonies that are corrected in the hygromycin mutation, 1 in 325 also contain the second change in the YAC β-globin sequence. Thus, approximately 10% of the cells with the corrected hygromycin-resistance gene also contain the edited β-globin gene.

Figure 11A:
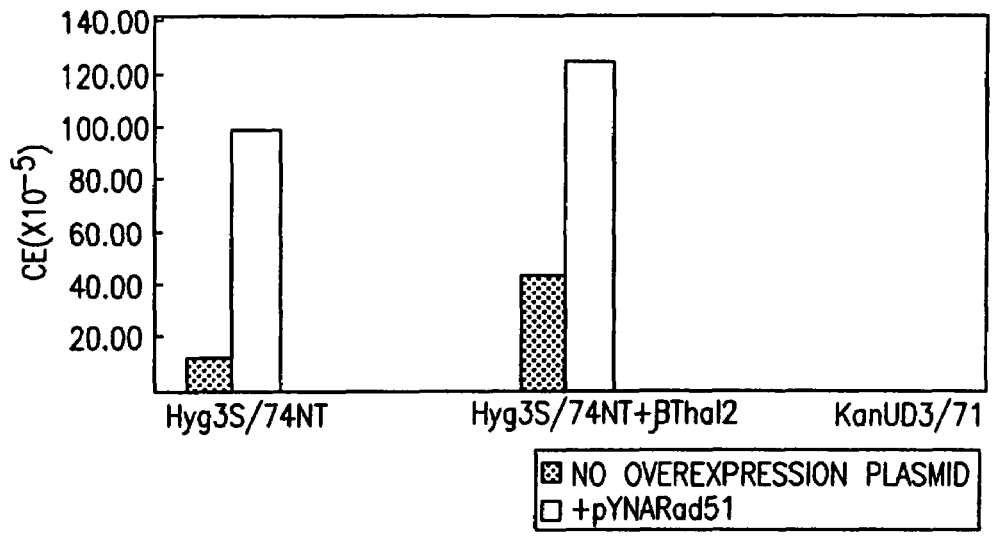
FIG. 11. Dual targeting and Rad51. (A) Efficiency of gene editing of hygromycin mutation using the dual targeting protocol in combination with overexpression of yeast Rad51. For these experiments, YAC-containing LSY678IntHyg(rep)β cells are grown in the presence of HU, electroporated with the selectable and nonselectable oligonucleotides, and allowed to recover in the presence of TSA. (B) Gene editing of the human β-globin gene directed by the βThal2 oligonucleotide, including the sequence of the altered segment before (SEQ ID NO: 31) and after (SEQ ID NO: 32) the conversion.

As shown in various experiments above, overexpression of RAD51 consistently increases the frequency of chromosomal gene editing. Accordingly, we introduce an expression plasmid containing the yeast RAD51 gene into LSY678lntHyg (rep)β cells (Table 24). FIG. 11 shows results of dual targeting in this strain and, as expected, expression of RAD51 increases the hygromycin C.E. of oligonucleotide Hyg3S/74NT (compare with FIG. 10). For these editing experiments, YAC-containing LSY678lntHyg(rep)β cells (Table 24) are grown in the presence of HU, electroporated with the selectable and nonselectable oligonucleotides, and allowed to recover in the presence of TSA (FIG. 9A). Here too, addition of a second oligonucleotide, βThal2, increases the correction efficiency further, to roughly 1 hygromycin-resistant colony per 800 aureobasidin-resistant colonies.

Figure 11B:
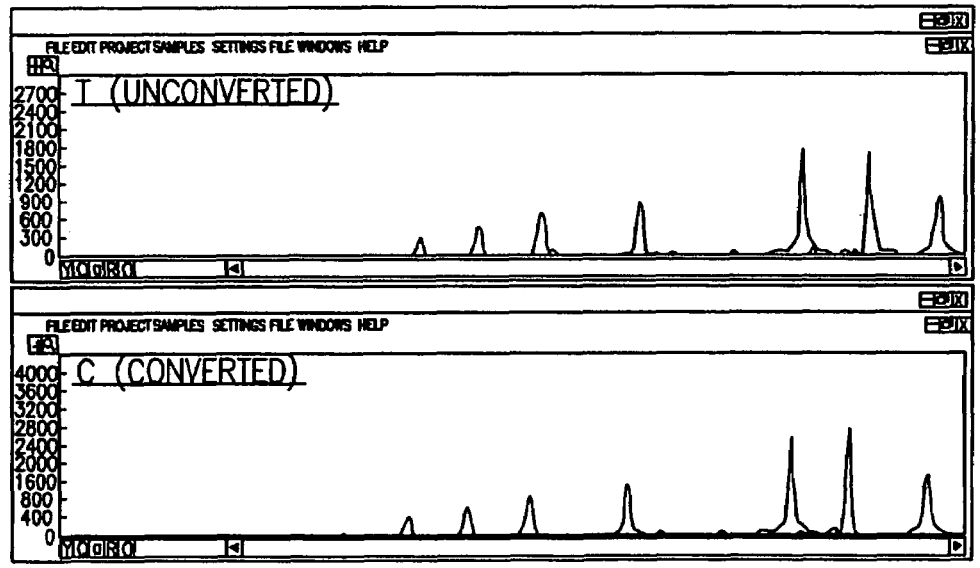

The βThal2 oligonucleotide is designed to direct the replacement of a T in the initiator ATG codon of exon 1 with a C, giving the non-initiator codon ACG (FIG. 9). FIG. 11B shows an ABI SNaPshot (middle panels) and direct DNA sequence (bottom panel) of the β-globin gene from a corrected Hygr colony; the T to C change is evident in both analytical panels. Importantly, of those colonies that are corrected in the hygromycin mutation, 1 in 70 also contain the second single-base change in the YAC β-globin sequence. Thus, the dual targeting approach is again successful; approximately 10% of the cells bearing the corrected hygromycin also contain the edited β-globin gene. In addition, in the presence of high levels of Rad51, gene editing occurs at a higher level, indicating that the presence of HU, TSA, and RAD51 overexpression exhibit synergistic effects on the overall process.

TABLE 24

Genotype of yeast strains

| Strain | Genotype/Description |
| --- | --- |
| AB1380 | MATa ura3 trp1 ade2-1 can1-100 lys2-1 his5 ψ+ |
| LSY678 | MATa ura3 trp1-1 ade2-1 leu2-3, 112 can1 his3-11,15 |
| LSY678IntHyg(rep) | LSY678 with mutant hygromycin gene and functional aureobasidin-resistance gene integrated into the AUR-1 locus on chromosome XI |
| LSY678IntHyg(rep)β | LSY678IntHyg(rep) with 250 kb YAC containing the human β-globin locus |
| LSY678IntHyg(rep)β + pYNARAD51 | The above strain containing an episomal expression plasmid overexpressing RAD51 |

Strains. The genotypes of the yeast strains used in these studies are listed in Table 24. Details of the LSY678IntHyg (rep) strain are published in Liu et al., Mol. Cell Biol. 22:3852-3863 (2002).

YAC Manipulations. The β-globin YAC is isolated from a preparative pulsed-field gel as described in Gnirke et al., Genomics 15:659-667 (1993). Briefly, concentrated chromosomal DNA from the β S-YAC strain (AB1380 background, see Chang et al., Proc. Natl. Acad. Sci. USA 95:14886-14890 (1998)) is prepared and resolved on a 1% low-melt agarose pulsed-field gel at 200V, 14° C., 20-50s, 33 hours. The YAC is isolated, equilibrated with a modified agarase buffer (10 mM BisTris-HCl pH6.5, 1 mM EDTA, 100 mM NaCl), treated with β-agarase I (New England Biolabs), and concentrated to a final volume of ~200 μl. Thirty μl of the purified YAC are introduced into competent LSY678IntHyg(rep) cells by spheroplast transformation and selection on agar/sorbitol plates lacking tryptophan. Transformants are restreaked and confirmed by pulsed-field gel electrophoresis, PCR, and sequence analysis for a fragment of the human β-globin gene.

The pYNARad51 episomal expression plasmid is constructed by replacing the TRP1 gene of pYNRad51 (see Liu et al., Nucleic Acids Res. 31, 2742-2750 (2002)) with the ADE2 gene. pYNARad51 is introduced into LSY678IntHyg(rep)β by electroporation and selection on agar plates lacking adenine.

Oligonucleotides. Hyg3S/74NT (SEQ ID NO: 9), βThal1 (SEQ ID NO: 27), and βThal2 (SEQ ID NO: 28) are ordered from IDT with HPLC purification. Hyg3S/74NT is a 74mer and both βThal1 and βThal2 are 71 mers; all three oligonucleotides have three phosphorothioate linkages at the 5' and 3' ends (FIG. 9).

Dual Targeting. The dual targeting protocol is outlined in FIG. 9A. LSY678IntHyg(rep)β cells are grown overnight in 10 ml YPD media at 30° C. The culture is diluted to $OD_{600}$ ~0.15-0.20 in 40 ml YPD media and grown for one doubling time to $OD_{600}$ ~0.3-0.4. 100 mM HU is added to the culture and the cells are grown for one doubling time to $OD_{600}$ ~0.6-0.8. Cells are harvested and resuspended in 1 ml YPD containing 25 μl 1 M DTT and grown for an additional 20 minutes at 30° C. The cells are washed twice with 25 ml cold $dH_2O$ and once with 25 ml cold 1 M sorbitol. The cells are resuspended gently in 1 ml cold 1 M sorbitol, spun for 5 minutes at 5000 rpm in a microcentrifuge, and resuspended in 120 μl 1M sorbitol. Forty microliters of cells are electroporated with 30 μg of each oligonucleotide in a 2 mm gap cuvette using a Bio-Rad Gene Pulser apparatus (Richmond, Calif.) with 1.5 kV, 25 μF, 200Ω, 1 pulse, 5s/pulsed length.

The cells are immediately resuspended in 3 ml YPD with 0.8 μg/ml aureobasidin A and 50 μg/ml TSA and recovered overnight at 30° C. The cells are spun down and resuspended in 1 ml fresh YPD. Dilutions are plated on YPD agar plates containing either hygromycin (300 μg/ml) or aureobasidin A (0.5 μg/ml). C.E.s are determined based on the number of hygromycin-resistant colonies per aureobasidin-resistant colonies.

Individual colonies are picked from the hygromycin agar plates into 96-well plates (Corning) containing 150 μl YPD and grown overnight at 30° C. with shaking. A 345 bp PCR product specific for the human β-globin locus is amplified from each of the 96 wells using the primers PCO2 (5'-TC-CTAAGCCAGTGCCAGAAG-3' (SEQ ID NO.: 29)) and PCO5 (5'-CTATTGGTCTCCTTAAACCTG-3' (SEQ ID NO.: 30)) in order to screen for the βThal1 or βThal2 conversion. The PCR reactions are performed by adding 8 pmoles of each primer and 2.5 μl yeast cell culture into pre-aliquoted PCR reaction mixes (Marsh/Abgene). The PCR reactions use an annealing temperature of 45.8° C. and an extension time of 1 min for 35 cycles. The PCR reactions are purified using a QiaQuick PCR 96-well purification kit (Qiagen) and eluted in a volume of 80 μl. One microliter of the purified PCR product is used as a template for the ABI SNaPshot reaction. The sequence of the SNaPshot primer used to screen for the βThal1 conversion is: 5'-CCCCCCCCCCCC-CCCCCAAGTCTGCCGTTACTGCCCTGTG-3' (SEQ ID NO.: 31). The sequence of the SNaPshot primer used to screen for the βThal2 conversion is: 5'-TTTTTTTTTTTTTTT-TTTTTTTTTTTTTTTTTTTTTCCACAGGAGTCAGGTG-CACC-3' (SEQ ID NO: 32). The SNaPshot reactions are performed using an ABI Prism SNaPshot Multiplex Kit, as specified by the manufacturer, and analyzed on an ABI 3100 Genetic Analyzer.

Sequence Analysis. Any potential converted clones from the SNaPshot reactions are confirmed by sequence analysis. Both strands of the PCR products are sequenced using primers PCO2 and PCO5 by Sanger dideoxy sequencing using an ABI Prism kit, as specified by the manufacturer, on an automated ABI 3100 Genetic Analyzer.

Although a number of embodiments and features have been described above, it will be understood by those skilled in the art that modification and variations of the described embodiments and features may be made without departing from either the spirit of the invention or the scope of the appended paragraphs. All publications and patents cited herein are incorporated by reference in their entireties.

What is claimed is:

1. A method of oligonucleotide-mediated targeted sequence alteration of a nucleic acid, the method comprising:
   combining a target nucleic acid in the presence of cellular repair proteins with a sequence-altering targeting oligonucleotide; and
   either adding lambda beta protein additionally to said combination or first contacting cells having said cellular repair proteins with an HDAC inhibitor or hydroxyurea;
   wherein said oligonucleotide-mediated targeted sequence alteration is dependent upon a cellular DNA mismatch repair mechanism;
   wherein said oligonucleotide is a single-stranded oligonucleotide 17-121 nucleotides in length, said oligonucleotide having an internally unduplexed domain of at least 8 contiguous deoxyribonucleotides,
   wherein said oligonucleotide is fully complementary in sequence to the sequence of a first strand of the nucleic acid target, but for one or more mismatches as between the sequences of said internally unduplexed deoxyribonucleotide domain and its complement on said target nucleic acid first strand, each of said mismatches positioned at least 8 nucleotides from said oligonucleotide's 5' and 3' terminal, and
   wherein said oligonucleotide has at least one terminal modification selected from the group consisting of: at least one terminal locked nucleic acid (LNA), at least one terminal 2'—O—Me base analog, at least one terminal phosphorothioate linkage, and at least three terminal phosphorothioate linkages.

2. The method of claim 1, wherein lambda beta protein is added additionally to said combination.

3. The method of claim 1, wherein the cells having said cellular repair proteins are first contacted by and HDAC inhibitor.

4. The method of claim 3, wherein said inhibitor is TSA.

5. The method of claim 1, wherein the cells having said cellular repair proteins are first contacted by hydroxyurea.

6. The method of claim 1, wherein said cellular repair proteins are purified, present in a cell-free protein extract, or present within an intact cell.

7. The method of claim 6, wherein said cellular repair proteins are present within an intact cell cultured ex vivo.

8. The method of claim 7, wherein said cell is a fungal cell, plant cell, or animal cell.

9. The method of claim 8, wherein said cell is an animal cell.

10. The method of claim 9, wherein said animal is a mammal.

11. The method of claim 10, wherein said mammal is a human.

12. The method of claim 11, wherein said human cell is a stem cell or progenitor cell.

13. The method of claim 12, wherein said human cell is a CD34+ hematopoietic stem cell or progenitor cell.

14. The method of claim 12, wherein said human cell is an embryonic stem cell.

15. The method of claim 1, wherein said target nucleic acid is in a chromosome.

16. The method of claim 15, wherein said chromosome is an artificial chromosome.

* * * * *

SEQUENCE LISTING

<160> NUMBER OF SEQ ID NOS: 32

<210> SEQ ID NO 1
<211> LENGTH: 70
<212> TYPE: DNA
<213> ORGANISM: Artificial
<220> FEATURE:
<223> OTHER INFORMATION: Combined DNA/RNA oligonucleotide
<220> FEATURE:
<221> NAME/KEY: stem_loop
<222> LOCATION: (1)..(54)
<223> OTHER INFORMATION:
<220> FEATURE:
<221> NAME/KEY: stem_loop
<222> LOCATION: (55)..(70)
<223> OTHER INFORMATION:

<400> SEQUENCE: 1
gcuauucggc uaggacuggg cacaauuuut tgtgcccagt cgtagccgaa tagcctctcc        60
uuuuggagag                                                              70

<210> SEQ ID NO 2
<211> LENGTH: 13
<212> TYPE: DNA
<213> ORGANISM: Escherichia coli

<400> SEQUENCE: 2
gtggatatgt cct                                                          13

<210> SEQ ID NO 3
<211> LENGTH: 13
<212> TYPE: DNA
<213> ORGANISM: Escherichia coli

<400> SEQUENCE: 3
gtggatacgt cct                                                          13

<210> SEQ ID NO 4
<211> LENGTH: 13
<212> TYPE: DNA
<213> ORGANISM: Escherichia coli

<400> SEQUENCE: 4
gtggataggt cct                                                          13

<210> SEQ ID NO 5
<211> LENGTH: 14
<212> TYPE: DNA
<213> ORGANISM: Escherichia coli

<400> SEQUENCE: 5
gtggataatg tcct                                                         14

<210> SEQ ID NO 6
<211> LENGTH: 12
<212> TYPE: DNA
<213> ORGANISM: Escherichia coli

<400> SEQUENCE: 6
gtggatagtc ct                                                           12

<210> SEQ ID NO 7
<211> LENGTH: 25

```
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (22)..(24)
<223> OTHER INFORMATION:

<400> SEQUENCE: 7
agggcgtgga tacgtcctgc gggta                                          25

<210> SEQ ID NO 8
<211> LENGTH: 74
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (71)..(73)
<223> OTHER INFORMATION:

<400> SEQUENCE: 8
ctcgtgcttt cagcttcgat gtaggagggc gtggatacgt cctgcgggta aatagctgcg    60
ccgatggttt ctac                                                      74

<210> SEQ ID NO 9
<211> LENGTH: 74
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (71)..(73)
<223> OTHER INFORMATION:

<400> SEQUENCE: 9
gtagaaacca tcggcgcagc tatttacccg caggacgtat ccacgccctc ctacatcgaa    60
gctgaaagca cgag                                                      74

<210> SEQ ID NO 10
<211> LENGTH: 70
<212> TYPE: DNA
<213> ORGANISM: Artificial
<220> FEATURE:
<223> OTHER INFORMATION: Combined DNA/RNA oligonucleotide
<220> FEATURE:
<221> NAME/KEY: stem_loop
<222> LOCATION: (1)..(54)
<223> OTHER INFORMATION:
<220> FEATURE:
<221> NAME/KEY: stem_loop
<222> LOCATION: (55)..(70)
<223> OTHER INFORMATION:

<400> SEQUENCE: 10
```

-continued agggcgugga taggtccugc ggguattttt acccgcagga cgtatccacg ccctcctaca    60
tttttgtagg    70

<210> SEQ ID NO 11
<211> LENGTH: 69
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (67)..(69)
<223> OTHER INFORMATION:

<400> SEQUENCE: 11
catcagagca gccaattgtc tgttgtgccc agtcgtagcc gaatagcctc tccacccaag    60
cggccggag    69

<210> SEQ ID NO 12
<211> LENGTH: 15
<212> TYPE: DNA
<213> ORGANISM: Escherichia coli

<400> SEQUENCE: 12
ttcggctagg actgg    15

<210> SEQ ID NO 13
<211> LENGTH: 15
<212> TYPE: DNA
<213> ORGANISM: Escherichia coli

<400> SEQUENCE: 13
ccagtcctag ccgaa    15

<210> SEQ ID NO 14
<211> LENGTH: 15
<212> TYPE: DNA
<213> ORGANISM: Escherichia coli

<400> SEQUENCE: 14
ttcggctacg actgg    15

<210> SEQ ID NO 15
<211> LENGTH: 15
<212> TYPE: DNA
<213> ORGANISM: Escherichia coli

<400> SEQUENCE: 15
ccagtcgtag ccgaa    15

<210> SEQ ID NO 16
<211> LENGTH: 19
<212> TYPE: PRT
<213> ORGANISM: Artificial
<220> FEATURE:
<223> OTHER INFORMATION: Ligand-binding peptide

<400> SEQUENCE: 16

Arg Val Asp Ala Ala Ala Arg Glu Ala Cys Cys Arg Glu Cys Cys Ala
1               5                   10                  15

Thr Ala Ile

<210> SEQ ID NO 17
<211> LENGTH: 74
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (71)..(73)
<223> OTHER INFORMATION:

<400> SEQUENCE: 17
ctcgtgcttt cagcttcgat gtaggagggc gtgggtacgt cctgcgggta aatagctgcg    60
ccgatggttt ctac                                                     74

<210> SEQ ID NO 18
<211> LENGTH: 74
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (71)..(73)
<223> OTHER INFORMATION:

<400> SEQUENCE: 18
ctcgtgcttt cagcttcgat gtaggagggc gtggatacgt cctgcgggta aacagctgcg    60
ccgatggttt ctac                                                     74

<210> SEQ ID NO 19
<211> LENGTH: 74
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (71)..(73)
<223> OTHER INFORMATION:

<400> SEQUENCE: 19
ctcgtgcttt cagcttcgat gtaggagggc gtggatacgt cctgcgggta aatagctgcg    60
ccgacggttt ctac                                                     74

<210> SEQ ID NO 20
<211> LENGTH: 24
<212> TYPE: DNA
<213> ORGANISM: Artificial
<220> FEATURE:
<223> OTHER INFORMATION: Oligonucleotide with locked nucleic acids

<400> SEQUENCE: 20
acccgcagga cgtatccacg ccct                                          24

-continued

<210> SEQ ID NO 21
<211> LENGTH: 70
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (67)..(69)
<223> OTHER INFORMATION:

<400> SEQUENCE: 21
aggtgctaca cttttcaaga ctagatgtct acaatgccac accgtggaaa agggtggccc    60
acataaggtt                                                          70

<210> SEQ ID NO 22
<211> LENGTH: 70
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (67)..(69)
<223> OTHER INFORMATION:

<400> SEQUENCE: 22
aaccttatgt gggccaccct tttccacggt gtggcattgt agacatctag tcttgaaaag    60
tgtagcacct                                                          70

<210> SEQ ID NO 23
<211> LENGTH: 42
<212> TYPE: DNA
<213> ORGANISM: Escherichia coli

<400> SEQUENCE: 23
gatgtaggag ggcgtggata tgtcctgcgg gtaaatagct gc                      42

<210> SEQ ID NO 24
<211> LENGTH: 42
<212> TYPE: DNA
<213> ORGANISM: Escherichia coli

<400> SEQUENCE: 24
gatgtaggag ggcgtggata ggtcctgcgg gtaaatagct gc                      42

<210> SEQ ID NO 25
<211> LENGTH: 42
<212> TYPE: DNA
<213> ORGANISM: Escherichia coli

<400> SEQUENCE: 25
gatgtaggag ggcgtggata cgtcctgcgg gtaaatagct gc                      42

<210> SEQ ID NO 26
<211> LENGTH: 54
<212> TYPE: DNA

<213> ORGANISM: Homo sapiens

<400> SEQUENCE: 26
atggtgcacc tgactcctgt ggagaagtct gccgttactg ccctgtgggg caag    54

<210> SEQ ID NO 27
<211> LENGTH: 71
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (68)..(70)
<223> OTHER INFORMATION:

<400> SEQUENCE: 27
gcctcaccac caacttcatc cacgttcacc ttgcctcaca gggcagtaac ggcagacttc    60
tccacaggag t    71

<210> SEQ ID NO 28
<211> LENGTH: 71
<212> TYPE: DNA
<213> ORGANISM: Artificial
<220> FEATURE:
<223> OTHER INFORMATION: Oligonucleotide with phosphorothioate linkages
<220> FEATURE:
<221> NAME/KEY: misc_feature
<222> LOCATION: (1)..(3)
<223> OTHER INFORMATION:
<220> FEATURE:
<221> NAME/KEY: misc_feature
<222> LOCATION: (68)..(70)
<223> OTHER INFORMATION:

<400> SEQUENCE: 28
taacggcaga cttctccaca ggagtcaggt gcaccgtggt gtctgtttga ggttgctagt    60
gaacacagtt g    71

<210> SEQ ID NO 29
<211> LENGTH: 28
<212> TYPE: DNA
<213> ORGANISM: Homo sapiens

<400> SEQUENCE: 29
agtctgccgt tactgccctg tggggcaa    28

<210> SEQ ID NO 30
<211> LENGTH: 28
<212> TYPE: DNA
<213> ORGANISM: Homo sapiens

<400> SEQUENCE: 30
agtctgccgt tactgccctg tgaggcaa    28

<210> SEQ ID NO 31
<211> LENGTH: 33
<212> TYPE: DNA
<213> ORGANISM: Homo sapiens

<400> SEQUENCE: 31
atggtgcacc tgactcctgt ggagaagtct gcc    33

```
<210> SEQ ID NO 32
<211> LENGTH: 33
<212> TYPE: DNA
<213> ORGANISM: Homo sapiens

<400> SEQUENCE: 32
acggtgcacc tgactcctgt ggagaagtct gcc                                    33
```